(12) United States Patent
Madsen et al.

(10) Patent No.: US 10,040,839 B2
(45) Date of Patent: Aug. 7, 2018

(54) INSULIN DERIVATIVES AND THE MEDICAL USES HEREOF

(71) Applicant: Novo Nordisk A/S, Bagsvaerd (DK)

(72) Inventors: Peter Madsen, Bagsvaerd (DK); Susanne Hostrup, Vaerloese (DK); Martin Muenzel, Broenshoej (DK); Thomas Boerglum Kjeldsen, Virum (DK); Claudia Ulrich Hjoerringgaard, Glostrup (DK); Christian Fledelius, Copenhagen OE (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 15/121,206

(22) PCT Filed: Feb. 26, 2015

(86) PCT No.: PCT/EP2015/053989
§ 371 (c)(1),
(2) Date: Aug. 24, 2016

(87) PCT Pub. No.: WO2015/128403
PCT Pub. Date: Sep. 3, 2015

(65) Prior Publication Data
US 2017/0008945 A1 Jan. 12, 2017

(30) Foreign Application Priority Data

Feb. 28, 2014 (EP) .................................... 14157215

(51) Int. Cl.
| | |
|---|---|
| *A61K 38/28* | (2006.01) |
| *C07K 14/62* | (2006.01) |
| *A61K 47/22* | (2006.01) |
| *A61K 38/00* | (2006.01) |

(52) U.S. Cl.
CPC .............. *C07K 14/62* (2013.01); *A61K 38/28* (2013.01); *A61K 47/22* (2013.01); *A61K 38/00* (2013.01)

(58) Field of Classification Search
None
See application file for complete search history.

(56) References Cited

U.S. PATENT DOCUMENTS

| | | |
|---|---|---|
| 3,528,960 A | 9/1970 | Haas |
| 3,864,325 A | 2/1975 | Smyth |
| 3,868,356 A | 2/1975 | Smyth |
| 3,869,437 A | 3/1975 | Lindsay et al. |
| 5,382,574 A * | 1/1995 | Jorgensen .............. A61K 38/28 514/6.4 |
| 5,650,486 A | 7/1997 | De Felippis |
| 5,750,497 A | 5/1998 | Havelund et al. |
| 5,898,067 A | 4/1999 | Balschmidt et al. |
| 5,905,140 A | 5/1999 | Hansen |
| 6,011,007 A | 1/2000 | Havelund et al. |
| 6,174,856 B1 | 1/2001 | Langballe et al. |
| 6,444,641 B1 | 9/2002 | Flora |
| 6,451,762 B1 | 9/2002 | Havelund et al. |
| 6,451,970 B1 | 9/2002 | Schaffer et al. |
| 6,531,448 B1 | 3/2003 | Brader |
| 6,620,780 B2 | 9/2003 | Markussen et al. |
| 6,869,930 B1 | 3/2005 | Havelund et al. |
| 6,960,561 B2 | 11/2005 | Boderke |
| 7,229,964 B2 | 6/2007 | Markussen et al. |
| 7,615,532 B2 | 11/2009 | Jonassen et al. |
| 8,003,605 B2 | 8/2011 | Bayer et al. |
| 8,067,362 B2 | 11/2011 | Kodra et al. |
| 2004/0138099 A1 | 7/2004 | Draeger |
| 2005/0014679 A1 | 1/2005 | Beals et al. |
| 2006/0018874 A1 | 1/2006 | Radhakrishnan et al. |
| 2006/0183667 A1 | 8/2006 | Jonassen et al. |
| 2006/0217290 A1 | 9/2006 | Kohn et al. |
| 2009/0074882 A1 | 3/2009 | Havelund et al. |
| 2009/0105121 A1 | 4/2009 | Jonassen et al. |
| 2009/0239784 A1 | 9/2009 | Jonassen et al. |
| 2009/0239785 A1 | 9/2009 | Hubalek et al. |
| 2010/0009899 A1 | 1/2010 | Jonassen et al. |
| 2010/0167990 A1 | 7/2010 | Poulsen et al. |
| 2010/0279931 A1 | 11/2010 | Garibay et al. |
| 2011/0230402 A1 | 9/2011 | Johansen et al. |
| 2011/0245163 A1 | 10/2011 | Jonassen et al. |

(Continued)

FOREIGN PATENT DOCUMENTS

| | | |
|---|---|---|
| EP | 2178912 A1 | 4/2010 |
| JP | H01254699 A | 10/1989 |

(Continued)

OTHER PUBLICATIONS

Dorte B. Steensgaard et al. "Ligand-Controlled Assembly of Hexamers, Dihexamers, and Linear Multihexamer Structures by the Engineered Acylated Insulin Degludec" Biochemistry. Published online Dec. 2012;Jan. 2013 vol. 52(2) pp. 295-309.
Havelund, S et al., Pharmaceutical Research, "The Mechanism of Protraction of Insulin Determir, A Long-Acting, Acylated Analog of Human Insulin", 2004, vol. 21, No. 8, pp. 1498-1504.
Bhatnagar, S. et al., Progress in Biophysics and Molecular Biology, 2006, pp. 199-228, vol. 91, Part 3.
Hashimoto, M. et al., Pharmaceutical Research, 1989, pp. 171-176, vol. 6 Part 2.
Helle B Olsen et al. "Structural Effects of Protein Lipidation as REvealed by LysB29-myristoyl, des(B30)" Biochemmistry. 2000. vol. 39(39) pp. 11893-11900.
Bernard, B.A, Newton S.A & Olden, K. "Effect of Size and Location of the oligosaccharide chain on protease degradtion of bovine pancreatic ribonuclease." J Biol Chem. vol. 258: 12198-12202 (1983).

(Continued)

*Primary Examiner* — Gyan Chandra
(74) *Attorney, Agent, or Firm* — Rosemarie R. Wilk-Orescan

(57) ABSTRACT

The present invention is in the therapeutic fields of drugs for medical conditions relating to diabetes. More specifically the invention relates to novel acylated derivatives of human insulin analogues. The invention also provides pharmaceutical compositions comprising such insulin derivatives, and relates to the use of such derivatives for the treatment or prevention of medical conditions relating to diabetes.

48 Claims, 13 Drawing Sheets

(56) References Cited

U.S. PATENT DOCUMENTS

| | | |
|---|---|---|
| 2012/0035104 A1 | 2/2012 | Kodra et al. |
| 2013/0190232 A1 | 7/2013 | Tagmose et al. |

FOREIGN PATENT DOCUMENTS

| | | |
|---|---|---|
| JP | 2002-518408 A | 6/2002 |
| JP | 2003-525846 A | 9/2003 |
| JP | 2005-526009 A | 9/2005 |
| RU | 1997110125 | 11/1995 |
| WO | 95/07931 A1 | 3/1995 |
| WO | 96/15803 A1 | 5/1996 |
| WO | 96/29344 | 9/1996 |
| WO | 97/31022 A1 | 8/1997 |
| WO | 98/42749 A1 | 10/1998 |
| WO | 1999/021578 A1 | 5/1999 |
| WO | 1999/022754 A1 | 5/1999 |
| WO | 1999/032116 A1 | 7/1999 |
| WO | 99/65941 A1 | 12/1999 |
| WO | 2001/000675 A1 | 1/2001 |
| WO | 2001/093837 A2 | 12/2001 |
| WO | 03/048195 A2 | 6/2003 |
| WO | 2005/005477 A2 | 1/2005 |
| WO | 2005/012347 A2 | 2/2005 |
| WO | 2005/016312 A1 | 2/2005 |
| WO | 2005/047508 A1 | 5/2005 |
| WO | 2005/054291 A1 | 6/2005 |
| WO | 2006/008238 A1 | 1/2006 |
| WO | 2006/082204 | 8/2006 |
| WO | 2006/082204 A1 | 8/2006 |
| WO | 2006/082205 | 8/2006 |
| WO | 2006/097521 | 9/2006 |
| WO | 2007/074133 A2 | 7/2007 |
| WO | 2007096431 A1 | 8/2007 |
| WO | 2007/128815 A1 | 11/2007 |
| WO | 2007/128817 A2 | 11/2007 |
| WO | 2008/013938 A2 | 1/2008 |
| WO | 2008/015099 A2 | 2/2008 |
| WO | 2008/145721 A2 | 12/2008 |
| WO | 2008/152106 A1 | 12/2008 |
| WO | 09/022013 A1 | 2/2009 |
| WO | 2009/015456 A1 | 2/2009 |
| WO | 2009/022005 A1 | 2/2009 |
| WO | 2009/060071 A1 | 5/2009 |
| WO | 2009/063072 A2 | 5/2009 |
| WO | 2009/067636 A2 | 5/2009 |
| WO | 2009/112583 A2 | 9/2009 |
| WO | 2009/115469 A1 | 9/2009 |
| WO | 2010/029159 A1 | 3/2010 |
| WO | 2010/049488 A1 | 5/2010 |
| WO | 2010/080609 A1 | 7/2010 |
| WO | 2011/000823 A1 | 1/2011 |
| WO | 2011/141407 A1 | 11/2011 |
| WO | 2011161124 A1 | 12/2011 |
| WO | 2012/171994 A1 | 12/2012 |
| WO | 2013/063572 A1 | 5/2013 |

OTHER PUBLICATIONS

Owek, R.A. "biological importance of glycosylation." Dev Biol Stand vol. 96, pp. 43-47 (1998).

Rudd, P.M, Elliott, T., Cresswell, P., Wilson, I.A & Dwek, R.A. "Glycosylation and the immune system." Science vol. 291: 2370-2376 (2001).

Asada H et al., Stability of acyl derivatives of insulin in the small intestine: Relative importance of insulin association characteristics in aqueous solution, Pharmaceutical Research, 1994, vol. 11 (8), 1115-1120.

D. G. Lindsay et al., Acetoacetylation of insulin, The Biochemical Journal, 1969, vol. 115(3), 587-595.

D. G. Lindsay et al., The Acetylation of Insulin, Biochemical Journal, 1971, vol. 121, 737-745.

Ehrat M. et al., Synthesis and Spectroscopic Characterization of Insulin Derivatives Containing One or Two Poly (ethylene oxide) Chains at Specific Positions, Biopolymers, 1983, vol. 22, 569-573.

Friesen Heinz-Jurgen et al., Preparation and Application of Nalpha -B1, N epsilon-B29-bis(tert.-butyloxycarbonyl) insulin, Hoppe-Seyler's Z. Physiological Chemistry, 1978, vol. 359, 103-111.

Hashimoto M et al., Synthesis of palmitoyl derivatives of insulin and their biological activities, Pharmaceutical Research, 1989, vol. 6(2), 171-176.

Hashizume M et al., Improvement of large intestinal absorption of insulin by chemical modification with palmitic acid in rats, The Journal of pharmacy and pharmacology, 1992, vol. 44(7), 555-559.

Lindsay D.G. et al., Carbamyl- and methylthiocarbamylinsulins, Biochimica et Biophysica Acta (BBA)—Protein Structure, 1972, vol. 263 (3), 658-665.

Shozo Muranishi et al., Trials of lipid modification of peptide hormones for intestinal delivery, Journal of Controlled Release, 1992, vol. 19, Issues 1-3, 179-188.

Takashi Uchio et al., Site-specific insulin conjugates with enhanced stability and extended action profile, Advanced Drug Delivery Reviews, 1999, vol. 35, Issues 2-3, 289-306.

Ulla Ribel et al., Equivalent In Vivo Biological Activity of Insulin Analogues and Human Insulin Despite Different In Vitro Potencies, Diabetes, 1990, vol. 39, 1033-1039.

Yogish C Kudva et al., Ultra-long-acting insulins for a lifestyle-related pandemic, The Lancet, 2011, vol. 377(9769), 880-881.

Asada et al. "Absorption Characteristics of Chemically Modified-Insulin Derivatives with Various Fatty Acids in the Small and Large Intestine," Journal of Pharmaceutical Sciences, Jun. 1995, vol. 84, pp. 682-687.

\* cited by examiner

Zucker rat PK - insulin of Example 2

Pig PK - insulin of Example 4

Pig PK - Insulin of Example 2

INSULIN DERIVATIVES AND THE MEDICAL USES HEREOF

CROSS-REFERENCE TO RELATED APPLICATIONS

This application is a 35 U.S.C. § 371 National Stage application of International Application PCT/EP2015/053989 (published as WO 2015/128403), filed Feb. 26, 2015, which claimed priority of European Patent Application 14157215.6, filed Feb. 28, 2014, the contents thereof which are incorporated by reference in their entirety.

SEQUENCE LISTING

The instant application contains a Sequence Listing which has been submitted in ASCII format via EFS-Web and is hereby incorporated by reference in its entirety. Said ASCII copy, created on Aug. 24, 2016, is named 8702US01_SeqList.txt and is 3 kilobytes in size.

TECHNICAL FIELD

The present invention is in the therapeutic fields of drugs for medical conditions relating to diabetes. More specifically the invention relates to novel acylated derivatives of human insulin analogues. The invention also provides pharmaceutical compositions comprising such derivatized insulin analogues, and relates to the use of such derivatives for the treatment or prevention of medical conditions relating to diabetes.

BACKGROUND OF THE INVENTION

Insulin therapy for the treatment of diabetes has been used for decades. Insulin therapy usually involves administering several injections of insulin each day. Such therapy usually involves administration of a long-acting basal injection once or twice daily, and an injection of a fast-acting insulin at mealtime (i.e. prandial use). One of the key improvements in insulin therapy was the introduction of rapid-acting insulin analogues. However, even with the rapid-acting insulin analogues, peak insulin levels typically do not occur until 50 to 70 minutes following the injection.

Therefore insulin injections do not replicate the natural time-action profile of insulin. In particular, the natural spike of the first-phase insulin release in a person without diabetes results in blood insulin levels rising within several minutes of the entry into the blood of glucose from a meal. By contrast, injected insulin enters the blood only slowly, with peak insulin levels occurring within 80 to 100 minutes following the injection of regular human insulin.

Because the rapid-acting insulin analogues do not adequately mimic the first-phase insulin release, diabetics using insulin therapy continue to have inadequate levels of insulin present at the initiation of a meal, and too much insulin present between meals. This lag in insulin delivery can result in hyperglycemia early after meal onset.

Insulin possesses self-association properties, and its concentration represents a major factor of self-association. At high concentrations, especially in pharmaceutical formulations, insulin will self-associate into dimer, hexamer, dodecamer, and crystal. However, the physiologically active form of insulin is the monomer, which binds with the insulin receptor and triggers a biological response.

The rapidity of insulin action is dependent on how quickly the insulin is absorbed from the subcutaneous tissue. When regular human insulin is injected subcutaneously, the formulation is primarily composed of hexamers containing two zinc ions. Due to its size, the hexameric insulin has a lower rate of diffusion and consequently, the absorption rate is slower than for smaller species.

Located within the hexamer are two zinc atoms that stabilize the molecule towards chemical and physical degradation. Post injection, a concentration driven dynamic equilibrium occurs in the subcutaneous tissue, causing the hexamers to dissociate into dimers, and then to monomers. Historically, these regular human insulin formulations require approximately 120 minutes to reach maximum plasma concentration levels. Zinc-insulin preparations, that are more quickly absorbed than regular human insulin, have been commercialised, e.g. insulin aspart and insulin lispro.

Zinc-free insulin formulations would enable faster subcutaneous absorption, but for insulins in general, the chemical and physical stability of zinc-free formulations is a challenge.

Various insulin derivatives have been suggested for different uses.

WO 1998 042749 describes zinc-free insulin crystals for pulmonary administration.

U.S. Pat. No. 6,960,561 describes zinc-free and low-zinc insulin preparations having improved stability.

WO 2007/096431 describes certain human insulin derivatives, including analogues i.a. at position A22 holding an acylated lysine residue, in position B29 holding an arginine residue, and being desB30, which derivatives are soluble at physiological pH values and have a prolonged profile of action, and intended for use as long acting insulins.

WO 2009/022013 describes certain acylated insulin analogues, including analogues i.a. at position A22 holding an acylated lysine residue, in position B29 holding an arginine residue, and being desB30, possessing higher insulin receptor binding affinities, and intended for use as long acting insulins.

WO 2009/112583 describes certain insulin analogues, including analogues at position A22 holding a lysine residue, in position B29 holding an arginine residue, and being desB30, exhibiting improved protease stability.

WO 2011/161124 describes certain acylated insulin analogues containing additional disulfide bonds for improved stability, including analogues i.a. at position A22 holding a lysine residue, in position B29 holding an arginine residue, and being desB30.

WO 2012/171994 describes certain insulin derivative comprising two or more substitutions, including analogues i.a. at position A22 holding an acylated lysine residue, in position B29 holding an arginine residue, and being desB30, for prolonged in vivo activity.

WO 2013 063572 describes ultra-concentrated rapid-acting insulin analogue formulations optionally devoid of zinc.

Moreover, acylation of peptides and proteins with albumin binding moieties have been used to prolong the duration of action of the peptides and proteins.

However, the insulin derivatives according to the present invention have not been reported, and their use as fast acting insulin derivatives for prandial use has never been suggested.

OBJECTS OF THE INVENTION

It is an object of the invention to provide insulin analogues that have a prandial profile following subcutaneous administration.

Another object of the invention is to provide insulin analogues that are chemically stable in formulation.

A third object of the invention is to provide insulin analogues that are chemically stable in formulation without added zinc.

A fourth object of the invention is to provide insulin analogues that are physically stable in formulation.

A fifth object of the invention is to provide insulin analogues that are physically stable in formulation without added zinc.

A sixth object of the invention is to provide insulin analogues that are chemically and physically stable in formulation.

A seventh object of the invention is to provide insulin analogues that are chemically and physically stable in formulation without added zinc.

An eight object of the invention is to provide insulin analogues that are hepatopreferential relative to currently marketed prandial insulins following subcutaneous administration.

A ninth object of the invention is to provide insulin analogues that are hepatoselective relative to currently marketed prandial insulins following subcutaneous administration.

A tenth object of the invention is to provide insulin analogues that are less prone to induce hypoglycaemia relative to currently marketed prandial insulins following prandial subcutaneous administration.

An eleventh object of the invention is to provide insulin analogues that are less prone to induce weight gain relative to currently marketed prandial insulins following prandial subcutaneous administration.

A twelfth object of the invention is to provide insulin analogues that are less prone to induce hypoglycaemia and weight gain relative to currently marketed prandial insulins following prandial subcutaneous administration.

Further objects of this invention are drawn to combinations of one or more of the objects mentioned above, and in particular the provision of insulin analogues that show a prandial profile following subcutaneous administration, while being chemically stable in formulations, and in particular in formulations without added zinc.

SUMMARY OF THE INVENTION

We have discovered that the A22K acylated insulin derivatives of the present invention have significantly improved properties relative to similar insulin derivatives of the prior art. We have in particular discovered that the insulin derivatives of the invention, in formulations containing no added zinc ions, and when compared to similar derivatives of the prior art, are associated with a smaller size of the molecular aggregates. Smaller species are known to diffuse more rapidly than larger species, and faster absorption is consequently to be expected. The size of these molecular aggregates can e.g. be measured as described herein by Small Angle X-ray Scattering (SAXS) and by performing series of dilutions with SEC-HPLC (size exclusion HPLC) as described in the examples section.

We have also discovered that the insulin derivatives of the invention, relative to similar derivatives of the prior art, in formulations containing no added zinc ions, are absorbed more rapidly after subcutaneous administration to pigs, thereby demonstrating a potential clinical utility as insulins for prandial use. We have discovered that the insulin derivatives of the invention, relative to similar derivatives of the prior art, in formulations containing no added zinc ions are associated with less "tailing" following subcutaneous administration to pigs. By less tailing is meant that the subcutaneous depot of injected insulin is absorbed more rapidly than for similar analogues of the prior art, so that the mean residence time (MRT) following subcutaneous administration is shorter for the insulin derivatives of the invention when compared to similar acylated derivatives of the prior art.

Zinc-free formulations enable faster subcutaneous absorption, but for insulins in general, chemical and physical stability of zinc-free formulations is a challenge, and has until now only been shown to be possible with insulin glulisine (Apidra®; B3K, B29E human insulin), and only in the presence of surfactants when dispensed in vials.

We have now discovered that a subset of the A22K acylated insulin derivatives of the invention, with substitutions in position B3, very unexpectedly and unprecedented are both chemically and physically stable in formulations with no added zinc-ions and no added surfactants.

An advantage by using acylated insulin derivatives as prandial insulin therapy is to achieve higher plasma insulin concentrations than those achieved with treatment with un-acylated prandial insulins, like insulin aspart, insulin lispro or insulin glulisine.

The A22K acylated insulin derivatives according to the invention have a prandial-like time-action profile following subcutaneous administration.

The A22K acylated insulin derivatives with tetradecanedioic acid, pentadecanedioic acid, or hexadecanedioic acid based albumin binders according to the invention have shown to confer very high insulin receptor binding affinities, affinities that are reduced in the presence of 1.5% human serum albumin (HSA).

The A22K acylated insulin derivatives according to the invention do not have reduced solubility at physiological salt concentrations.

Accordingly, in its first aspect, the invention provides novel insulin derivatives, which insulin derivatives are acylated derivatives of human insulin analogues, which analogues are [A22K, desB27, B29R, desB30] relative to human insulin; and which insulin analogue is derivatized by acylation of the epsilon amino group of the lysine residue at the A22 position with a group of Formula II

[Acyl]-[Linker]- wherein the Linker group is an amino acid chain composed of from 1 to 10 amino acid residues selected from -gGlu- and -OEG-; wherein gGlu represents a gamma glutamic acid residue; OEG represents the residue of 8-amino-3,6-dioxaoctanoic acid (i.e. a group of the formula —NH—(CH$_2$)$_2$—O—(CH$_2$)$_2$—O—CH$_2$—CO—); which amino acid residues may be present in any order; and which amino acid chain comprises at least one gGlu residue; and wherein the Acyl group is a residue of an α,ω-di-carboxylic acid selected from 1,14-tetradecanedioic acid; 1,15-pentadecanedioic acid; and 1,16-hexadecanedioic acid;

which acylated analogue, may additionally comprise the A14E, and/or B3E or B3Q substitutions.

In another first aspect, the invention provides pharmaceutical compositions comprising the insulin derivative of the invention, and one or more pharmaceutically acceptable excipients.

In a further aspect, the invention relates to use of the insulin derivative of the invention as a medicament.

In a yet further aspect the invention provides methods for the treatment, prevention or alleviation of diseases, disorders or conditions relating to diabetes, Type 1 diabetes, Type 2 diabetes, impaired glucose tolerance, hyperglycemia, dyslipidemia, obesity, metabolic syndrome (metabolic syndrome X, insulin resistance syndrome), hypertension, cognitive disorders, atherosclerosis, myocardial infarction, stroke, cardiovascular disorders, coronary heart disease, inflammatory bowel syndrome, dyspepsia, or gastric ulcers, which method comprises administration to a subject in need thereof a therapeutically effective amount of the insulin derivative of the invention.

Other objects of the invention will be apparent to the person skilled in the art from the following detailed description and examples.

DETAILED DESCRIPTION OF THE INVENTION

Insulin Derivatives

In its first aspect the present invention provides novel insulin derivatives, which insulin derivative are acylated analogues of human insulin.

The insulin derivative of the invention may in particular be characterised as an acylated analogue of human insulin, which analogue is [A22K, desB27, B29R, desB30] relative to human insulin;

and which insulin analogue is derivatized by acylation of the epsilon amino group of the lysine residue at the A22 position with a group of Formula II

[Acyl]-[Linker]- wherein the Linker group is an amino acid chain composed of from 1 to 10 amino acid residues selected from -gGlu- and -OEG-; wherein gGlu represents a gamma glutamic acid residue; OEG represents the residue of 8-amino-3,6-dioxaoctanoic acid (i.e. a group of the formula —NH—(CH$_2$)$_2$—O—(CH$_2$)$_2$—O—CH$_2$—CO—); which amino acid residues may be present in any order; and which amino acid chain comprises at least one gGlu residue; and wherein the Acyl group is a residue of an α,ω-di-carboxylic acid selected from 1,14-tetradecanedioic acid; 1,15-pentadecanedioic acid; and 1,16-hexadecanedioic acid.

The insulin derivative of the invention may additionally comprise the A14E, and/or B3E or B3Q substitutions.

In one embodiment, the analogue of human insulin is [A14E, A22K, B3E, desB27, B29R, desB30]; [A14E, A22K, desB27, B29R, desB30]; [A22K, B3E, desB27, B29R, desB30]; [A22K, B3Q, desB27, B29R, desB30]; or [A22K, desB27, B29R, desB30]; relative to human insulin; and which insulin analogue is acylated at the epsilon amino group of the lysine residue at the A22 position.

In another embodiment, the analogue of human insulin is [A22K, desB27, B29R, desB30], relative to human insulin; and which insulin analogue is acylated at the epsilon amino group of the lysine residue at the A22 position.

In a third embodiment, the analogue of human insulin is [A22K, B3E, desB27, B29R, desB30], relative to human insulin; and which insulin analogue is acylated at the epsilon amino group of the lysine residue at the A22 position.

In a fourth embodiment, the analogue of human insulin is [A22K, B3Q, desB27, B29R, desB30], relative to human insulin; and which insulin analogue is acylated at the epsilon amino group of the lysine residue at the A22 position.

In a fifth embodiment, the analogue of human insulin is [A14E, A22K, desB27, B29R, desB30], relative to human insulin; and which insulin analogue is acylated at the epsilon amino group of the lysine residue at the A22 position.

In a sixth embodiment, the analogue of human insulin is [A14E, A22K, B3E, desB27, B29R, desB30], relative to human insulin; and which insulin analogue is acylated at the epsilon amino group of the lysine residue at the A22 position.

As described above, the insulin analogue is derivatized by acylation of the epsilon amino group of the lysine residue at the A22 position with a group of Formula II, as described above, i.e. a substituent holding an acyl group bound to a linking group.

In the context of this invention the linking group according to Formula II this is an amino acid chain composed of from 1 to 10 amino acid residues selected from -gGlu- and -OEG-.

In one embodiment, the linking group according to Formula II is an amino acid chain composed of from 1 to 7 amino acid residues selected from -gGlu- and -OEG-, comprising of from 1 to 4 gGlu residues and from 0 to 3 OEG residues.

In another embodiment, the linking group according to Formula II is selected from -gGlu-; -2×gGlu-; -3×gGlu-; -4×gGlu-; -gGlu-2×OEG-; -gGlu-3×(OEG-gGlu)-; -4×gGlu-2×OEG-; -2×OEG-; and -2×OEG-gGlu-.

In a third embodiment, the linking group according to Formula II is -gGlu-.

In a fourth embodiment, the linking group according to Formula II is -2×gGlu-.

In a fifth embodiment, the linking group according to Formula II is -3×gGlu-.

In a sixth embodiment, the linking group according to Formula II is -4×gGlu-.

In a seventh embodiment, the linking group according to Formula II is -gGlu-2×OEG-.

In an eight embodiment, the linking group according to Formula II is -gGlu-3×(OEG-gGlu)-.

In a ninth embodiment, the linking group according to Formula II is -4×gGlu-2×OEG-.

In a tenth embodiment, the linking group according to Formula II is -2×OEG-.

In an eleventh embodiment, the linking group according to Formula II is -2×OEG-gGlu-.

In the context of this invention the acyl group according to Formula II is derived from 1,14-tetradecanedioic acid; 1,15-pentadecanedioic acid; or 1,16-hexadecanedioic acid.

In one embodiment, the acyl group according to Formula II is derived from 1,14-tetradecanedioic acid (i.e. 1,14-tetradecanedioyl).

In another embodiment, the acyl group according to Formula II is derived from 1,15-pentadecanedioic acid (i.e. 1,15-pentadecanedioyl).

In a third embodiment, the acyl group according to Formula II is derived from 1,16-hexadecanedioic acid (i.e. 1,16-hexadecanedioyl).

In a further embodiment, the group of Formula II, as described above, is tetradecanedioyl-gGlu-; tetradecanedioyl-2×gGlu-; tetradecanedioyl-3×gGlu-; tetradecanedioyl-4×gGlu-; tetradecanedioyl-gGlu-2×OEG-; tetradecanedioyl-4×gGlu-2×OEG-; tetradecanedioyl-2×OEG-; pentadecanedioyl-4×gGlu; hexadecanedioyl-4×gGlu-; hexadecanedioyl-gGlu-2×OEG-; or hexadecanedioyl-3×(gGlu-OEG)-gGlu-.

In another embodiment, the group of Formula II is tetradecanedioyl-gGlu-.

In a third embodiment, the group of Formula II is tetradecanedioyl-2×gGlu-.

In a fourth embodiment, the group of Formula II is tetradecanedioyl-3×gGlu-.

In a fifth embodiment, the group of Formula II is tetradecanedioyl-4×gGlu-.

In a sixth embodiment, the group of Formula II is tetradecanedioyl-gGlu-2×OEG-.

In a seventh embodiment, the group of Formula II is tetradecanedioyl-2×OEG-.

In an eight embodiment, the group of Formula II is tetradecanedioyl-4×gGlu-2×OEG-.

In a ninth embodiment, the group of Formula II is pentadecanedioyl-4×gGlu-.

In a tenth embodiment, the group of Formula II is hexadecanedioyl-4×gGlu-.

In an eleventh embodiment, the group of Formula II is hexadecanedioyl-gGlu-2×OEG-.

In a twelfth embodiment, the group of Formula II is hexadecanedioyl-3×(gGlu-OEG)-gGlu-.

The insulin derivative of the invention may in particular be one selected from the group consisting of A22K(N(eps)-tetradecanedioyl-4×gGlu), desB27, B29R, desB30 human insulin;

A22K(N(eps)-tetradecanedioyl-4×gGlu), B3E, desB27, B29R, desB30 human insulin;

A14E, A22K(N(eps)-tetradecanedioyl-4×gGlu), desB27, B29R, desB30 human insulin;

A22K(N(eps)-hexadecanedioyl-4×gGlu), B3E, desB27, B29R, desB30 human insulin;

A22K(N(eps)-hexadecanedioyl-gGlu-2×OEG), B3E, desB27, B29R, desB30 human insulin;

A22K(N(eps)-hexadecanedioyl-3×(gGlu-OEG)-gGlu), B3E, desB27, B29R, desB30 human insulin;

A22K(N(eps)-tetradecanedioyl-4×gGlu), B3Q, desB27, B29R, desB30 human insulin;

A22K(N(eps)-hexadecanedioyl-gGlu-2×OEG), B3Q, desB27, B29R, desB30 human insulin;

A22K(N(eps)-hexadecanedioyl-3×(gGlu-OEG)-gGlu), B3Q, desB27, B29R, desB30 human insulin;

A22K(N(eps)-tetradecanedioyl-2×gGlu), desB27, B29R, desB30 human insulin;

A22K(N(eps)-hexadecanedioyl-4×gGlu), desB27, B29R, desB30 human insulin;

A22K(N(eps)-hexadecanedioyl-gGlu-2×OEG), desB27, B29R, desB30 human insulin;

A22K(N(eps)-hexadecanedioyl-3×(gGlu-OEG)-gGlu), desB27, B29R, desB30 human insulin;

A22K(N(eps)-tetradecanedioyl-gGlu), desB27, B29R, desB30 human insulin;

A22K(N(eps)-tetradecanedioyl-gGlu-2×OEG), B3E, desB27, B29R, desB30 human insulin;

A22K(N(eps)-tetradecanedioyl-gGlu-2×OEG), B3Q, desB27, B29R, desB30 human insulin;

A22K(N(eps)-tetradecanedioyl-2×OEG), desB27, B29R, desB30 human insulin;

A22K(N(eps)-hexadecanedioyl-4×gGlu), B3Q, desB27, B29R, desB30 human insulin;

A22K(N(eps)-pentadecanedioyl-4×gGlu), B3E, desB27, B29R, desB30 human insulin;

A22K(N(eps)-tetradecanedioyl-4×gGlu-2×OEG), desB27, B29R, desB30 human insulin;

A22K(N(eps)-tetradecanedioyl-4×gGlu-2×OEG), B3E, desB27, B29R, desB30 human insulin;

A14E, A22K(N(eps)-tetradecanedioyl-gGlu-2×OEG), B3E, desB27, B29R, desB30 human insulin;

A14E, A22K(N(eps)-tetradecanedioyl-4×gGlu), B3E, desB27, B29R, desB30 human insulin;

A22K(N(eps)-tetradecanedioyl-2×gGlu), B3E, desB27, B29R, desB30 human insulin;

A22K(N(eps)-tetradecanedioyl-gGlu), B3E, desB27, B29R, desB30 human insulin; and A22K(N(eps)-tetradecanedioyl-3×gGlu), B3E, desB27, B29R, desB30 human insulin.

Preferred Features of the Compounds of the Invention

The present invention may be further characterised by reference to one or more of the following features:

1. An acylated analogue of human insulin, which analogue is [A22K, desB27, B29R, desB30]; and which insulin analogue optionally is substituted with A14E, and/or B3E, or B3Q; and which insulin analogue is acylated at the epsilon amino group of the lysine residue at the A22 position.

2. The acylated analogue of human insulin according to clause 1, which analogue is [A22K, desB27, B29R, desB30] relative to human insulin; and which insulin analogue is substituted with B3E, or B3Q; and which insulin analogue is acylated at the epsilon amino group of the lysine residue at the A22 position.

3. The acylated analogue of human insulin according to clause 1, which analogue is [A22K, B3E, desB27, B29R, desB30] relative to human insulin; and which insulin analogue is acylated at the epsilon amino group of the lysine residue at the A22 position.

4. The acylated analogue of human insulin according to clause 1, which analogue is [A22K, B3Q, desB27, B29R, desB30] relative to human insulin; and which insulin analogue is acylated at the epsilon amino group of the lysine residue at the A22 position.

5. The acylated analogue of human insulin according to clause 1, which analogue is [A14E, A22K, desB27, B29R, desB30] relative to human insulin; and which insulin analogue is acylated at the epsilon amino group of the lysine residue at the A22 position.

6. The acylated analogue of human insulin according to clause 1, which analogue is [A14E, A22K, desB27, B29R, desB30] relative to human insulin; and which insulin analogue is substituted with B3E or B3Q; and which insulin analogue is acylated at the epsilon amino group of the lysine residue at the A22 position.

7. The acylated analogue of human insulin according to clause 1, which analogue is [A14E, A22K, B3E, desB27, B29R, desB30] relative to human insulin; and which insulin analogue is acylated at the epsilon amino group of the lysine residue at the A22 position.

8. The acylated analogue of human insulin according to clause 1, which analogue is [A22K, desB27, B29R, desB30] relative to human insulin; and which insulin analogue is derivatized by acylation of the epsilon amino group of the lysine residue at the A22 position with a group of Formula II

[Acyl]-[Linker]- wherein the Linker group is an amino acid chain composed of from 1 to 10 amino acid residues selected from -gGlu- and -OEG-; wherein gGlu represents a gamma glutamic acid residue; and OEG represents the residue of 8-amino-3,6-dioxaoctanoic acid (i.e. a group of the formula —NH—(CH$_2$)$_2$—O—(CH$_2$)$_2$—O—CH$_2$—CO—);

which amino acid residues may be present in any order; and which amino acid chain comprises at least one gGlu residue; and wherein the Acyl group is a residue of an α,ω-di-carboxylic acid selected from 1,14-tetradecanedioic acid;
1,15-pentadecanedioic acid; and
1,16-hexadecanedioic acid;

which acylated analogue, may additionally comprise the A14E, and/or B3E or B3Q substitutions.

9. The acylated analogue of human insulin according to clause 7, wherein the Acyl group is a di-acid group derived from 1,14-tetradecanedioic acid; 1,15-pentadecanedioic acid; or 1,16-hexadecanedioic acid.

10. The acylated analogue of human insulin according to clause 7, wherein the Acyl group is a di-acid group derived from 1,14-tetradecanedioic acid or 1,16-hexadecanedioic acid.

11. The acylated analogue of human insulin according to clause 7, wherein the Acyl group is a di-acid group derived from 1,14-tetradecanedioic acid.

12. The acylated analogue of human insulin according to clause 7, wherein the Acyl group is a di-acid group derived from 1,16-hexadecanedioic acid.

13. The acylated analogue of human insulin according to clause 7, wherein the Acyl group is a di-acid group derived from 1,15-pentadecanedioic acid.

14. The acylated analogue of human insulin according to clause 7, wherein the Linking group comprises 1-10 gGlu residues.

15. The acylated analogue of human insulin according to clause 7, wherein the Linking group comprises 1-8 gGlu residues.

16. The acylated analogue of human insulin according to clause 7, wherein the Linking group comprises 1-6 gGlu residues.

17. The acylated analogue of human insulin according to clause 7, wherein the Linking group comprises 1-4 gGlu residues.

18. The acylated analogue of human insulin according to clause 7, wherein the Linking group comprises 1-3 gGlu residues.

19. The acylated analogue of human insulin according to clause 7, wherein the Linking group comprises 1-2 gGlu residues.

20. The acylated analogue of human insulin according to clause 7, wherein the Linking group comprising one gGlu residue.

21. The acylated analogue of human insulin according to clause 7, wherein the Linking group comprises two gGlu residues.

22. The acylated analogue of human insulin according to clause 7, wherein the Linking group comprises three gGlu residues.

23. The acylated analogue of human insulin according to clause 7, wherein the Linking group comprises four gGlu residues.

24. The acylated analogue of human insulin according to clause 7, wherein the Linking group comprises 1-6 OEG residues.

25. The acylated analogue of human insulin according to clause 7, wherein the Linking group comprises 1-4 OEG residues.

26. The acylated analogue of human insulin according to clause 7, wherein the Linking group comprises 1-3 OEG residues.

27. The acylated analogue of human insulin according to clause 7, wherein the Linking group comprises one OEG residue.

28. The acylated analogue of human insulin according to clause 7, wherein the Linking group comprises two OEG residues.

29. The acylated analogue of human insulin according to clause 7, wherein the Linking group comprises three OEG residues.

30. The acylated analogue of human insulin according to clause 7, wherein the Linking group comprises no OEG residues.

31. The acylated analogue of human insulin according to clause 7, wherein the Linking group is selected from -gGlu-; -2×gGlu-; -3×gGlu-; -gGlu-3×(OEG-Glu)-; -4×gGlu-; -2×OEG-; -4×gGlu-2×OEG-; -2×OEG-gGlu-; and -gGlu-2× OEG-.

32. The acylated analogue of human insulin according to clause 7, wherein the Linking group is selected from -gGlu; -gGlu-3×(OEG-gGlu)-; and -gGlu-2×OEG-.

33. The acylated analogue of human insulin according to clause 7, wherein the Linking group is selected from -gGlu-; -2×gGlu-; and -4×gGlu-.

34. The acylated analogue of human insulin according to clause 7, wherein the group of Formula II [Acyl]-[Linker]- is tetradecanedioyl-gGlu-; tetradecanedioyl-2×gGlu-; tetradecanedioyl-3×gGlu-; tetradecanedioyl-4×gGlu-; tetradecanedioyl-gGlu-2×OEG-; tetradecanedioyl-2×OEG-; tetradecanedioyl-4×gGlu-2×OEG-; hexadecanedioyl-4×gGlu-; hexadecanedioyl-gGlu-2×OEG-; or hexadecanedioyl-3× (gGlu-OEG)-gGlu-.

35. The acylated analogue of human insulin according to clause 7, wherein the group of Formula II [Acyl]-[Linker]- is tetradecanedioyl-gGlu-; tetradecanedioyl-2×gGlu-; tetradecanedioyl-4×gGlu-; tetradecanedioyl-gGlu-2×OEG-; or tetradecanedioyl-2×OEG-; hexadecanedioyl-4×gGlu-; hexadecanedioyl-gGlu-2×OEG-; or hexadecanedioyl-3×(gGlu-OEG)-gGlu-.

Definitions

Nomenclature

Herein, the naming of the insulins is done according to the following principles:

The term "analogue" is frequently used for the insulin protein or peptide in question before it undergoes further chemical modification (derivatisation), and in particular acylation. The product resulting from such a chemical modification (derivatisation) is usually called a "derivative" or "acylated analogue". However, in the context of this application, the term "analogue" designates analogues of human insulin as well as (the acylated) derivatives of such human insulin analogues.

The names are given as analogues, derivatives and modifications (acylations) relative to human insulin. For the naming of the acyl moiety (i.e. the [Acyl]-[Linker]- group of formula II), in some instances the naming is done according to IUPAC nomenclature, and in other instances the naming is done as peptide nomenclature.

As an example, the acyl moiety of the following structure (Chem.1):

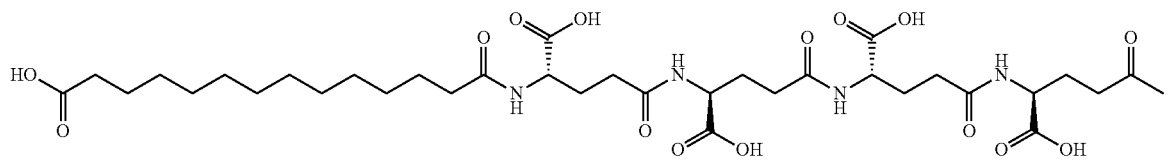 [SMILES: CC(=O)CC[C@H](NC(=O)CC[C@H](NC(=O)CC[C@H](NC(=O)CC[C@H](NC(=O)CCCCCCCCCCCCC(=O)O)C(=O)O)C(=O)O)C(=O)O)C(=O)O]

may be named "tetradecanedioyl-4×gGlu", "tetradecanedioyl-4×γGlu" or, "1,14-tetradecanedioyl-4×gGlu" or the like, wherein γGlu (and gGlu) is short hand notation for the amino acid gamma glutamic acid in the L-configuration, and "4×" means that the residue following is repeated 4 times.

Similarly, the acyl moiety of the following structure (Chem.2):

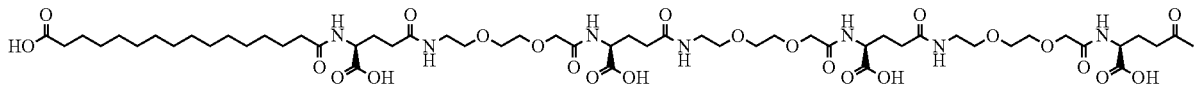 [SMILES: CC(=O)CC[C@H](NC(=O)COCCOCCNC(=O)CC[C@H](NC(=O)COCCOCCNC(=O)CC[C@H](NC(=O)COCCOCCNC(=O)CC[C@H](NC(=O)CCCCCCCCCCCCCCC(=O)O)C(=O)O)C(=O)O)C(=O)O)C(=O)O]

can for example be named "hexadecanedioyl-(gGlu-OEG)$_3$-gGlu", "hexadecanedioyl-(gGlu-OEG)$_3$-gGlu)", "hexadecanedioyl-3×(gGlu-OEG)-gGlu)", "1,16-hexadecanedioyl-(gGlu-OEG)$_3$-gGlu)", "1,16-hexadecanedioyl-(gGlu-OEG)$_3$-gGlu)", "1,16-hexadecanedioyl-3×(gGlu-OEG)-gGlu)", "hexadecanedioyl-(γGlu-OEG)$_3$-γGlu)", "hexadecanedioyl-(γGlu-OEG)$_3$-γGlu)", or "hexadecanedioyl-3×(γGlu-OEG)-γGlu)";

wherein the moiety of the following structure (Chem.3):

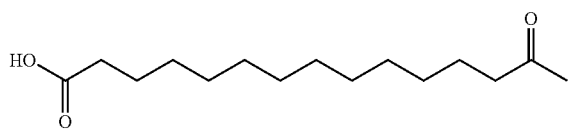 [SMILES: CC(=O)CCCCCCCCCCCCC(=O)O]

can for example be named tetradecanedioyl, 1,14-tetradecanedioyl or (short hand notation) C14 diacid. Similar notations apply for similar residues with 15 and 16 carbon atoms, pentadecanedioyl, C15 diacid, and hexadecanedioyl, C16 diacid, respectively.

γGlu (and gGlu) is short hand notation for the amino acid gamma glutamic acid in the L-configuration.

OEG is short hand notation for the amino acid residue 8-amino-3,6-dioxa-octanoic acid, $NH_2(CH_2)_2O(CH_2)_2OCH_2CO_2H$.

"2×" and "3×" means that the residues following is repeated 2, respectively, 3 times.

For example, the insulin derivative of Example 1 is named "A22K(N(eps)-tetradecanedioyl-4×gGlu), desB27, B29R, desB30 human insulin" to indicate that the A-chain, that contains 21 amino acid residues in human insulin, has been extended by 1 amino acid (position A22), with a lysine (K), that further is modified by acylation on the epsilon nitrogen in the lysine residue of A22, denoted $N^\epsilon$ (or N(eps)) by the moiety tetradecanedioyl-4×gGlu, the amino acid in position B27, T in human insulin, has been deleted, the amino acid in position B29, K in human insulin, has been substituted with arginine, R, the amino acid in position B30, threonine, T, in human insulin, has been deleted. Asterisks in the formulae below indicate that the residue in question is different (i.e. substituted) as compared to human insulin.

Throughout this application, both formulas and names of preferred insulins of the invention are given.

In addition, the insulins of the invention are also named according to IUPAC nomenclature (OpenEye, IUPAC style). According to this nomenclature, the insulin derivative of Example 1 is assigned the following name: N{Alpha}([ArgB29],des-ThrB27,ThrB30-Insulin(human)-(A)-peptidyl)-N{Epsilon} [(4S)-4-carboxy-4-[[(4S)-4-carboxy-4-[[(4S)-4-carboxy-4-[[(4S)-4-carboxy-4-(13-carboxytridecanoylamino)butanoyl]amino]butanoyl]-amino]butanoyl]amino]butanoyl]Lys,(B)-peptide.

It should be noted that formulas can be written with the lysine residue (that is modified by acylation) either is drawn with the lysine residue expanded (as shown e.g. in example 23) or drawn with the lysine residue contracted (as shown e.g. in example 1). In all cases the acyl group is attached to the epsilon nitrogen of the lysine residue.

For the sake of completeness it may be mentioned that deletion of the residue in position B27 (desB27) results in (formal) movement of the remaining amino acid residues towards the N-terminal end by one residue. Consequently, such an analogue may also be named B27P, B28R, desB29-30, since the residue in position B28 is a proline and the residue in position B29 is an arginine (see e.g. the compound of Example 1). This is because by deleting B27, the next amino acid in the sequence then shifts place and thus the amino acid in position B28 (proline) is shifted to the B27 position.

Physical Stability

The term "physical stability" of the insulin preparation as used herein refers to the tendency of the protein to form biologically inactive and/or insoluble aggregates of the protein as a result of exposure of the protein to thermo-mechanical stresses and/or interaction with interfaces and surfaces that are destabilizing, such as hydrophobic surfaces and interfaces. Physical stability of the aqueous protein preparations is evaluated by means of visual inspection and/or turbidity measurements after exposing the preparation filled in suitable containers (e.g. cartridges or vials) to mechanical/physical stress (e.g. agitation) at different temperatures for various time periods. Visual inspection of the preparations is performed in a sharp focused light with a dark background. A preparation is classified physically unstable with respect to protein aggregation, when it shows visual turbidity in daylight. Alternatively, the turbidity of the preparation can be evaluated by simple turbidity measurements well-known to the skilled person. Physical stability of the aqueous protein preparations can also be evaluated by using a spectroscopic agent or probe of the conformational status of the protein. The probe is preferably a small molecule that preferentially binds to a non-native conformer of the protein. One example of a small molecular spectroscopic probe of protein structure is Thioflavin T. Thioflavin T is a fluorescent dye that has been widely used for the detection of amyloid fibrils. In the presence of fibrils, and perhaps other protein configurations as well, Thioflavin T gives rise to a new excitation maximum at about 450 nm and enhanced emission at about 482 nm when bound to a fibril protein form. Unbound Thioflavin T is essentially non-fluorescent at the wavelengths.

Chemical Stability

The term "chemical stability" of the protein preparation as used herein refers to changes in the covalent protein structure leading to formation of chemical degradation products with potential less biological potency and/or potential increased immunogenic properties compared to the native protein structure. Various chemical degradation products can be formed depending on the type and nature of the native protein and the environment to which the protein is exposed. Increasing amounts of chemical degradation products are often seen during storage and use of the protein preparation. Most proteins are prone to deamidation, a process in which the side chain amide group in glutaminyl or asparaginyl residues is hydrolysed to form a free carboxylic acid or asparaginyl residues to form an isoAsp derivative. Other degradations pathways involves formation of high molecular weight products where two or more protein molecules are covalently bound to each other through transamidation and/ or disulfide interactions leading to formation of covalently bound dimer, oligomer and polymer degradation products (Stability of Protein Pharmaceuticals, Ahern T J & Manning M G, Plenum Press, New York 1992). Oxidation (of for instance methionine residues) can be mentioned as another variant of chemical degradation. The chemical stability of the protein preparation can be evaluated by measuring the amount of the chemical degradation products at various time-points after exposure to different environmental conditions (the formation of degradation products can often be accelerated by for instance increasing temperature). The amount of each individual degradation product is often determined by separation of the degradation products depending on molecule size, hydrofobicity, and/or charge using various chromatography techniques (e.g. SEC-HPLC and/or RP-HPLC). Since HMWP products are potentially immunogenic and not biologically active, low levels of HMWP are advantageous.

Methods of Synthesis

The insulin derivatives of the invention may be obtained by conventional methods for the preparation of insulin, insulin analogues and insulin derivatives, and in particular the methods described in the working examples.

In one embodiment, the insulin derivative of the invention is obtained by acylation of the epsilon amino group of the lysine residue at the A22 position with a group of Formula II which is tetradecanedioyl-4×gGlu.

In another embodiment, the insulin derivative of the invention is obtained by acylation of the epsilon amino group of the lysine residue at the A22 position at high pH, and in particular at a pH in the range of from 9.5 to 13, with a group of Formula II which is tetradecanedioyl-4×gGlu.

More particularly the insulin derivative of the invention is obtained by acylation of the epsilon amino group of the lysine residue at the A22 position with the compound (S)-2-((S)-4-Carboxy-4-{(S)-4-carboxy-4-[(S)-4-carboxy-4-(13-carboxy-tridecanoylamino)-butyrylamino]-butyrylamino}-butyrylamino)-pentanedioic acid 5-(2,5-dioxo-pyrrolidin-1-yl) ester (or alternatively designated tetradecanedioyl-4×gGlu-OSu) (Chem.4).

In another embodiment the insulin derivative of the invention is obtained by acylation of the epsilon amino group of the lysine residue at the A22 position with the compound 14-[[(1S)-1-carboxy-4-[2-[2-[2-[2-[2-[2-(2,5-dioxopyrrolidin-1-yl)oxy-2-oxoethoxy]ethoxy]ethylamino]-2-oxoethoxy]ethoxy]ethylamino]-4-oxobutyl]amino]-14-oxotetradecanoic acid (or alternatively designated tetradecanedioyl-gGlu-2×OEG-OSu) (Chem.5).

Preferred Features for Synthesis of the Compounds of the Invention

The present invention may be further characterised by reference to one or more of the following features:

1. The compound (S)-2-((S)-4-Carboxy-4-{(S)-4-carboxy-4-[(S)-4-carboxy-4-(13-carboxy-tridecanoylamino)-butyrylamino]-butyrylamino}-butyrylamino)-pentanedioic acid 5-(2,5-dioxo-pyrrolidin-1-yl) ester (or alternatively designated tetradecanedioyl-4×gGlu-OSu) (Chem.4), for use in an acylation process as an intermediate in the synthesis of the insulin derivative of the invention.

2. The compound 14-[[(1S)-1-carboxy-4-[2-[2-[2-[2-[2-[2-(2,5-dioxopyrrolidin-1-yl)oxy-2-oxoethoxy]ethoxy]ethylamino]-2-oxoethoxy]ethoxy]ethylamino]-4-oxobutyl]amino]-14-oxotetradecanoic acid (or alternatively designated tetradecanedioyl-gGlu-2×OEG-OSu) (Chem.5), for use in an acylation process as an intermediate in the synthesis of the insulin derivative of the invention.

3. A compound according to either one of clauses 1-2 for use as an intermediate compound in the synthesis of an insulin derivative, which insulin derivative is an acylated analogue of human insulin, which analogue holds the mutation A22K relative to human insulin, and to which position a compound of either one of clauses 1-2 is acylated.

4. A compound according to either one of clauses 1-2 for use as an intermediate compound in the synthesis of an insulin derivative, which insulin derivative is an acylated analogue of human insulin, which analogue is [A22K, desB27, B29R, desB30] relative to human insulin, and which analogue is acylated in position A22K with a compound of either one of clauses 1-2.

5. A compound according to either one of clauses 1-2 for use as an intermediate compound in the synthesis of an insulin derivative, which insulin derivative is an acylated analogue of human insulin, which analogue is [A22K, desB27, B29R, desB30] relative to human insulin, and which acylated analogue may additionally comprise the A14E, and/or B3E or B3Q substitutions, and which analogue is acylated in position A22K with a compound of either one of clauses 1-2.

6. The compound according to clause 1 for use as an intermediate compound in the synthesis of A22K(N(eps)-tetradecanedioyl-4×gGlu), desB27, B29R, desB30 human insulin;

A22K(N(eps)-tetradecanedioyl-4×gGlu), B3E, desB27, B29R, desB30 human insulin;

A14E, A22K(N(eps)-tetradecanedioyl-4×gGlu), desB27, B29R, desB30 human insulin;

A22K(N(eps)-tetradecanedioyl-4×gGlu), B3Q, desB27, B29R, desB30 human insulin;

A22K(N(eps)-tetradecanedioyl-4×gGlu-2×OEG), desB27, B29R, desB30 human insulin;

A22K(N(eps)-tetradecanedioyl-4×gGlu-2×OEG), B3E, desB27, B29R, desB30 human insulin; or A14E, A22K(N(eps)-tetradecanedioyl-4×gGlu), B3E, desB27, B29R, desB30 human insulin.

Biological Activity

In another aspect the invention provides novel insulin derivatives for use as medicaments, or for use in the manufacture of medicaments or pharmaceutical compositions.

The insulin derivatives of the invention are found to be short and fast acting insulin derivatives that are considered well suited for prandial use.

The insulin derivatives of the invention all possess insulin receptor affinities adequate for activating the insulin receptor in order to give the glycaemic response needed, i.e. being able to lower blood glucose in animals and humans.

The insulin derivatives of the invention are found to have a balanced insulin receptor (IR) to insulin-like growth factor 1 receptor (IGF-1R) affinity ratio (IR/IGF-1R).

In one aspect, the A22K acylated insulin of the invention has an IR/IGF-1R ratio of above 0.3; of above 0.4; of above 0.5; of above 0.6; of above 0.7; of above 0.8; of above 0.9; of above 1; of above 1.5; of above 2.

In another aspect, the A22K acylated insulin analogue is a compound of the invention, wherein the Acyl group of Formula II is derived from 1,14-tetradecanedioic acid, and which acylated insulin analogue has a mean residence time (MRT) of less than 250 minutes; of less than 200 minutes; of less than 175 minutes; of less than 150 minutes; of less than 125 minutes; following subcutaneous injection of a 600 μM (approx.) formulation of the acylated insulin analogue of the invention, containing 1.6% (w/vol, approx.) glycerol and 30 mM phenol/m-cresol, pH 7.4, to pigs.

In another embodiment, the A22K acylated insulin analogue is a compound of the invention, wherein the Acyl group of Formula II is derived from 1,16-hexadecanedioic acid, and which acylated insulin analogue has a mean residence time (MRT) of less than 700 minutes; of less than 600 minutes; of less than 500 minutes; of less than 400 minutes; of less than 300 minutes; following subcutaneous injection of a 600 μM (approx.) formulation of the acylated insulin analogue of the invention, containing 1.6% (w/vol, approx.) glycerol and 30 mM phenol/m-cresol, pH 7.4, to pigs.

In a further aspect, the invention relates to the medical use of the acylated insulin analogue of the invention, and in particular to the use of such insulin derivatives for the treatment, prevention or alleviation of diseases, disorders or conditions relating to diabetes, Type 1 diabetes, Type 2 diabetes, impaired glucose tolerance, hyperglycemia, dyslipidemia, obesity, metabolic syndrome (metabolic syndrome X, insulin resistance syndrome), hypertension, cognitive disorders, atherosclerosis, myocardial infarction, stroke, cardiovascular disorders, coronary heart disease, inflammatory bowel syndrome, dyspepsia, or gastric ulcers, which method comprises administration to a subject in need thereof a therapeutically effective amount of the insulin derivative of the invention.

In another embodiment, the invention relates to the use of such insulin derivatives for the treatment, prevention or alleviation of diseases, disorders or conditions relating to diabetes, Type 1 diabetes, Type 2 diabetes, or impaired glucose tolerance, which method comprises administration to a subject in need thereof a therapeutically effective amount of the insulin derivative of the invention.

In a third embodiment, the invention relates to the use of such insulin derivatives for the treatment, prevention or alleviation of diseases, disorders or conditions relating to diabetes, and in particular Type 1 diabetes or Type 2 diabetes.

Pharmaceutical Compositions

The present invention relates to acylated insulin analogues useful as medicaments.

Therefore, in another aspect, the invention provides novel pharmaceutical compositions comprising a therapeutically effective amount of an insulin derivative according to the present invention.

The pharmaceutical composition according to the invention optionally comprises one or more pharmaceutically acceptable carriers and/or diluents.

The pharmaceutical composition of the present invention may further comprise other excipients commonly used in pharmaceutical compositions e.g. preservatives, chelating agents, tonicity agents, absorption enhancers, stabilizers, antioxidants, polymers, surfactants, metal ions, oleaginous vehicles and proteins (e.g., human serum albumin, gelatine or proteins).

In one embodiment of the invention the pharmaceutical composition of the invention is an aqueous preparation, i.e. preparation comprising water. Such preparation is typically a solution or a suspension. In a further embodiment of the invention the pharmaceutical composition is an aqueous solution.

The term "aqueous preparation" is defined as a preparation comprising at least 50% w/w water. Likewise, the term "aqueous solution" is defined as a solution comprising at least 50% w/w water, and the term "aqueous suspension" is defined as a suspension comprising at least 50% w/w water. Aqueous suspensions may contain the active compounds in admixture with excipients suitable for the manufacture of aqueous suspensions.

In one embodiment of the invention the insulin preparation comprises an aqueous solution of an insulin derivative of the present invention, wherein said insulin compound is present in a concentration from about 0.1 mM to about 20.0 mM; more particularly of from about 0.2 mM to about 4.0 mM; of from about 0.3 mM to about 2.5 mM; of from about 0.5 mM to about 2.5 mM; of from about 0.6 mM to about 2.0 mM; or of from about 0.6 mM to about 1.2 mM.

In another embodiment of the invention the insulin preparation comprises an aqueous solution of an insulin derivative of the present invention, wherein said insulin compound is present in a concentration of about 0.1 mM, of about 0.3 mM, of about 0.4 mM, of about 0.6 mM, of about 0.9 mM, of about 1.2 mM, of about 1.5 mM, or of about 1.8 mM The pharmaceutical composition of the present invention may further comprise a buffer system. The buffer may be selected from the group consisting of, but not limited to, sodium acetate, sodium carbonate, sodium dihydrogen phosphate, disodium hydrogen phosphate, sodium phosphate, and tris(hydroxymethyl)-aminomethan, bicine, tricine, malic acid, glycyl-glycine, ethylene diamine, succinic acid, maleic acid, fumaric acid, tartaric acid, aspartic acid or mixtures thereof. Each one of these specific buffers constitutes an alternative embodiment of the invention.

In one embodiment the buffer is a phosphate buffer. In yet another embodiment, the concentration of said phosphate buffer is in the range from about 0.1 mM to 20 mM, In yet another embodiment the concentration of said phosphate buffer is in the range from 0.1 mM to about 10 mM, or from about 0.1 mM to about 8 mM, from about 1 mM to about 8 mM, or from about 2 mM to about 8 mM, or from 6 mM to 8 mM.

The pH of the injectable pharmaceutical composition of the invention is in the range of from 3 to 8.5. Preferably, the injectable pharmaceutical composition according to the invention has a pH in the range from about 6.8 to about 7.8.

In one embodiment the pH is in the range from about 7.0 to about 7.8, or from 7.2 to 7.6.

The insulin preparations of the present invention may further comprise a tonicity agent. The tonicity agent may be selected from the group consisting of a salt (e.g. sodium chloride), a sugar or sugar alcohol, an amino acid (e.g. L-glycine, L-histidine, arginine, lysine, isoleucine, aspartic acid, tryptophan, threonine), an alditol (e.g. glycerol (glycerine), 1,2-propanediol (propyleneglycol), 1,3-propanediol, 1,3-butanediol) polyethyleneglycol (e.g. PEG400), or mixtures thereof. Any sugar such as mono-, di-, or polysaccharides, or water-soluble glucans, including for example fructose, glucose, mannose, sorbose, xylose, maltose, lactose, sucrose, trehalose, dextran, pullulan, dextrin, cyclodextrin, soluble starch, hydroxyethyl starch and carboxymethylcellulose-Na may be used. In one embodiment the sugar additive is sucrose. Sugar alcohol includes, for example, mannitol, sorbitol, inositol, galactitol, dulcitol, xylitol, and arabitol. In one embodiment the sugar alcohol additive is mannitol. The sugars or sugar alcohols mentioned above may be used individually or in combination. Each one of these specific tonicity agents or mixtures hereof constitutes an alternative embodiment of the invention.

In a one embodiment of the invention, glycerol and/or mannitol and/or sodium chloride may be present in an amount corresponding to a concentration of from 0 to 250 mM, from 0 to 200 mM, or from 0 to 100 mM.

The insulin preparations of the present invention may further comprise a pharmaceutically acceptable preservative. The preservative may be present in an amount sufficient to obtain a preserving effect. The amount of preservative in a pharmaceutical composition of the invention may be determined from e.g. literature in the field and/or the known amount(s) of preservative in e.g. commercial products. Each one of these specific preservatives or mixtures hereof constitutes an alternative embodiment of the invention. The use of a preservative in pharmaceutical preparations is described, for example in Remington: *The Science and Practice of Pharmacy*, 19$^{th}$ edition, 1995.

In one embodiment, the injectable pharmaceutical composition comprises at least one phenolic compound as preservative agent.

In another embodiment the phenolic compound for use according to the invention may be present in up to about 6 mg/mL of final injectable pharmaceutical composition, in particular of up to about 4 mg/mL of final injectable pharmaceutical composition.

In another embodiment the phenolic compound for use according to the invention may be present in an amount of up to about 4.0 mg/mL of final injectable pharmaceutical composition; in particular of from about 0.5 mg/mL to about 4.0 mg/mL; or of from about 0.6 mg/mL to about 4.0 mg/mL.

In another embodiment the preservative is phenol.

In another embodiment, the injectable pharmaceutical composition comprises a mixture of phenol and m-cresol as preservative agent.

In another embodiment, the injectable pharmaceutical composition comprises about 16 mM phenol (1.5 mg/mL) and about 16 mM m-cresol (1.72 mg/mL).

The pharmaceutical composition of the present invention may further comprise a chelating agent. The use of a chelating agent in pharmaceutical preparations is well-known to the skilled person. For convenience reference is made to Remington: *The Science and Practice of Pharmacy*, 19$^{th}$ edition, 1995.

The pharmaceutical composition of the present invention may further comprise a absorption enhancer. The group of absorption enhancers may include but is not limited to nicotinic compounds. The term nicotinic compound includes nicotinamide, nicotinic acid, niacin, niacin amide and vitamin B3 and/or salts thereof and/or any combination thereof.

In one embodiment, the nicotinic compound is nicotinamide, and/or nicotinic acid, and/or a salt thereof. In another embodiment the nicotinic compound is nicotinamide. The nicotinic compound for use according to the invention may in particular be N-methyl nicotinamide, N,N-diethylnicotinamide, N-ethylnicotinamide, N,N-dimethylnicotinamide, N-propyl nicotinamide or N-butyl nicotinamide.

In another embodiment, the nicotinic compound is present in the amount of from about 5 mM to about 200 mM; in particular in the amount of from about 20 mM to about 200 mM; in the amount of from about 100 mM to about 170 mM; or in the amount of from about 130 mM to about 170 mM, such as about 130 mM, about 140 mM, about 150 mM, about 160 mM or about 170 mM.

The pharmaceutical composition of the present invention may further comprise a stabilizer. The term "stabilizer" as used herein refers to chemicals added to polypeptide containing pharmaceutical preparations in order to stabilize the peptide, i.e. to increase the shelf life and/or in-use time of such preparations. For convenience reference is made to Remington: *The Science and Practice of Pharmacy*, 19$^{th}$ edition, 1995.

The pharmaceutical composition of the invention may further comprise an amount of an amino acid base sufficient to decrease aggregate formation by the polypeptide or protein during storage of the composition. The term "amino acid base" refers to an amino acid or a combination of amino acids, where any given amino acid is present either in its free base form or in its salt form. The amino acids may in particular be arginine, lysine, aspartic acid, glutamic acid, aminoguanidine, ornithine or N-monoethyl L-arginine, ethionine or buthionine, or S-methyl-L cysteine. In one embodiment of the invention the amino acid base may be present in an amount corresponding to a concentration of from 1 to 100 mM; of from 1 to 50 mM; or of from 1 to 30 mM.

In one embodiment, the pharmaceutical composition of the present invention may further comprise a surfactant. The term "surfactant" as used herein refers to any molecules or ions that are comprised of a water-soluble (hydrophilic) part, the head, and a fat-soluble (lipophilic) segment. Surfactants accumulate preferably at interfaces, which the hydrophilic part is orientated towards the water (hydrophilic phase) and the lipophilic part towards the oil- or hydrophobic phase (i.e. glass, air, oil etc.). The concentration at which surfactants begin to form micelles is known as the critical micelle concentration or CMC. Furthermore, surfactants lower the surface tension of a liquid. Surfactants are also known as amphipathic compounds. The use of a surfactant in pharmaceutical preparations is well-known to the skilled person. For convenience reference is made to Remington: *The Science and Practice of Pharmacy*, 19$^{th}$ edition, 1995.

The invention further relates to a method for the preparation of such insulin preparations. The insulin preparations of this invention can be prepared by using any of a number of recognized methods. For example, the preparations can be prepared by mixing an aqueous solution of excipients with an aqueous solution of the insulin derivative, after which the pH is adjusted to a desired level and the mixture is made up to the final volume with water followed by sterile filtration.

Zinc-Free Pharmaceutical Compositions

Insulin preparations traditionally comprise zinc added as e.g. the chloride or acetate salt to obtain an acceptable stability of the pharmaceutical preparation. However, it has surprisingly been found that certain insulin derivatives of the invention, while maintaining a sufficient chemical and physical stability, may be formulated into pharmaceutical compositions without the addition of zinc, thereby giving a faster onset of action than comparable insulin analogues that need $Zn^{2+}$ ions for maintaining sufficient chemical and physical stability. The zinc-free formulations are faster absorbed from the subcutaneous tissue, and thus allowing for prandial use.

In this respect it needs mentioning, that a zinc-free insulin pharmaceutical composition is indeed difficult to obtain, as traces of zinc, to a more or less extent, may be present in the excipients conventionally used for the manufacture of pharmaceutical compositions, and in particular in the rubber materials used in medical containers.

Therefore, in one aspect, the invention provides pharmaceutical compositions comprising an insulin derivative of the invention, formulated as a low-zinc composition, i.e. without separate addition of zinc to the preparation. Such pharmaceutical compositions are usually referred to as "zinc-free compositions", although they may in fact be considered "low-zinc compositions".

However, provided zinc-free excipients can be provided, the insulin derivatives of the present invention in fact allows for the preparation of zinc-free pharmaceutical compositions. Therefore, in another aspect, the invention provides zinc-free pharmaceutical compositions comprising an insulin derivative of the invention, and one or more pharmaceutically acceptable carriers or diluents, devoid of any zinc.

We have moreover discovered that a subset of the A22K acylated insulin derivatives of the invention, holding a substitution in position B3, adds to both the chemical and physical stability of pharmaceutical compositions formulated without addition of zinc-ions and with no added surfactants. Therefore, in a further aspect, the invention provides a low-zinc or zinc-free pharmaceutical composition as described above, comprising an insulin derivative of the invention comprising an additional substitution in position B3 (i.e. B3E or B3Q), and one or more pharmaceutically acceptable carriers or diluents, in which pharmaceutical composition, however, no surfactant has been added.

In one embodiment the invention provides a pharmaceutical composition formulated as a low-zinc composition, with no added zinc ions, comprising an insulin derivative and one or more pharmaceutically acceptable carriers or diluents, wherein the insulin derivative is an acylated analogue of human insulin, which analogue is

[A22K, B3E or B3Q, desB27, B29R, desB30] relative to human insulin;

and which insulin analogue is derivatized by acylation of the epsilon amino group of the lysine residue at the A22 position with a group of Formula II

[Acyl]-[Linker]- wherein the Linker group is an amino acid chain composed of from 1 to 10 amino acid residues selected from -gGlu- and -OEG-; wherein gGlu represents a gamma glutamic acid residue;
OEG represents the residue of 8-amino-3,6-dioxaoctanoic acid (i.e. a group of the formula —NH—$(CH_2)_2$—O—$(CH_2)_2$—O—$CH_2$—CO—);
which amino acid residues may be present in any order; and
which amino acid chain comprises at least one gGlu residue; and
wherein the Acyl group is a residue of an α,ω-di-carboxylic acid selected from
1,14-tetradecanedioic acid;
1,15-pentadecanedioic acid; and
1,16-hexadecanedioic acid;
which acylated analogue, may additionally comprise the A14E substitution.

In another embodiment, the additional substitution in position B3 is B3E.

In a third embodiment, the additional substitution in position B3 is B3Q.

In a fourth embodiment the invention provides a pharmaceutical composition, formulated as a low-zinc composition, with no added zinc ions, comprising an acylated analogue of human insulin selected from:

A22K(N(eps)-tetradecanedioyl-4×gGlu), B3E, desB27, B29R, desB30 human insulin;
A22K(N(eps)-hexadecanedioyl-4×gGlu), B3E, desB27, B29R, desB30 human insulin;
A22K(N(eps)-hexadecanedioyl-gGlu-2×OEG), B3E, desB27, B29R, desB30 human insulin;
A22K(N(eps)-hexadecanedioyl-3×(gGlu-OEG)-gGlu), B3E, desB27, B29R, desB30 human insulin;
A22K(N(eps)-tetradecanedioyl-gGlu-2×OEG), B3E, desB27, B29R, desB30 human insulin;
A22K(N(eps)-pentadecanedioyl-4×gGlu), B3E, desB27, B29R, desB30 human insulin;
A22K(N(eps)-tetradecanedioyl-4×gGlu), B3Q, desB27, B29R, desB30 human insulin;
A22K(N(eps)-hexadecanedioyl-gGlu-2×OEG), B3Q, desB27, B29R, desB30 human insulin;
A22K(N(eps)-hexadecanedioyl-3×(gGlu-OEG)-gGlu), B3Q, desB27, B29R, desB30 human insulin;
A22K(N(eps)-tetradecanedioyl-gGlu-2×OEG), B3Q, desB27, B29R, desB30 human insulin;
A22K(N(eps)-hexadecanedioyl-4×gGlu), B3Q, desB27, B29R, desB30 human insulin;
A14E, A22K(N(eps)-tetradecanedioyl-4×gGlu), B3E, desB27, B29R, desB30 human insulin;
A14E, A22K(N(eps)-tetradecanedioyl-gGlu-2×OEG), B3E, desB27, B29R, desB30 human insulin;
A22K(N(eps)-tetradecanedioyl-2×gGlu), B3E, desB27, B29R, desB30 human insulin;
A22K(N(eps)-tetradecanedioyl-3×gGlu), B3E, desB27, B29R, desB30 human insulin;
A22K(N(eps)-tetradecanedioyl-4×gGlu-2×OEG), B3E, desB27, B29R, desB30 human insulin; and
A22K(N(eps)-tetradecanedioyl-gGlu), B3E, desB27, B29R, desB30 human insulin.

In yet another embodiment, the invention provides a low-zinc pharmaceutical composition as described above, wherein the zinc ions may be present in an amount corresponding to a concentration of less than 0.2 $Zn^{2+}$ ions per 6 insulin molecules; of less than 0.15 $Zn^{2+}$ ions per 6 insulin molecules; of less than 0.12 $Zn^{2+}$ ions per 6 insulin molecules; 0.1 $Zn^{2+}$ ions per 6 insulin molecules; of less than 0.09 $Zn^{2+}$ ions per 6 insulin molecules; of less than 0.08 $Zn^{2+}$ ions per 6 insulin molecules; of less than 0.07 $Zn^{2+}$ ions per 6 insulin molecules; of less than 0.06 $Zn^{2+}$ ions per 6 insulin molecules; of less than 0.05 $Zn^{2+}$ ions per 6 insulin molecules; of less than 0.04 $Zn^{2+}$ ions per 6 insulin molecules; of less than 0.03 $Zn^{2+}$ ions per 6 insulin molecules; of less than 0.02 $Zn^{2+}$ ions per 6 insulin molecules; or of less than 0.01 $Zn^{2+}$ ions per 6 insulin molecules.

In a further embodiment, the invention provides a low-zinc or zinc-free pharmaceutical composition as described above, formulated as an injectable composition. The pharmaceutical composition of this invention may be obtained using conventional methods known in the art. For example, the components may be mixed together in the form of aqueous solutions, after which the pH is adjusted to a desired level and the mixture is made up to the final volume with water followed by sterile filtration.

Parenteral administration may be performed by subcutaneous, intramuscular, intraperitoneal or intravenous injection by means of a syringe, optionally a pen-like syringe. Alternatively, parenteral administration can be performed by means of an infusion pump. As a further option, the insulin preparations containing the insulin compound of the invention can also be adapted to transdermal administration, e.g. by needle-free injection or from a microneedle patch, optionally an iontophoretic patch, or transmucosal, e.g. buccal, administration.

Insulin preparations according to the present invention may be administered to a patient in need of such treatment at several sites, for example, at topical sites, for example, skin and mucosal sites, at sites which bypass absorption, for example, administration in an artery, in a vein, in the heart, and at sites which involve absorption, for example, administration in the skin, under the skin, in a muscle or in the abdomen.

In one embodiment, the insulin preparations of this invention are well-suited for application in pen-like devices used for insulin therapy by injection.

The pharmaceutical composition of the invention may be used in the treatment of diabetes by parenteral administration.

In another embodiment the insulin preparations of the present invention may also be prepared for use in various medical devices normally used for the administration of insulin, including continuous subcutaneous insulin infusion therapy by use of pumps, and/or for application in basal insulin therapy.

It is recommended that the dosage of the insulin preparations of this invention which is to be administered to the patient be selected by a physician. It is currently contemplated that the insulin derivative according to the invention shall be present in the final pharmaceutical composition in an amount of from about 0.1 mM to about 20.0 mM; more particularly of from about 0.2 mM to about 4.0 mM; of from about 0.3 mM to about 2.5 mM; of from about 0.5 mM to about 2.5 mM; of from about 0.6 mM to about 2.0 mM; or of from about 0.6 mM to about 1.2 mM.

Preferred Features of the Pharmaceutical Composition of the Invention

The present invention may be further characterised by reference to one or more of the following features:

1. A pharmaceutical composition comprising the acylated analogue of human insulin of the invention, and one or more pharmaceutically acceptable excipients.

2. The pharmaceutical composition according to clause 1, formulated as a low-zinc composition, with no added zinc ions.

3. The pharmaceutical composition according to clause 1, formulated as a low-zinc composition, with no added zinc ions, comprising an acylated analogue of human insulin holding a substitution in position B3.

4. The pharmaceutical composition according to clause 1, formulated as a low-zinc composition, with no added zinc ions, comprising an acylated analogue of human insulin holding the substitution B3E or B3Q.

5. The pharmaceutical composition according to clause 1, formulated as a low-zinc composition, with no added zinc ions, comprising an acylated analogue of human insulin holding the substitution B3E.

6. The pharmaceutical composition according to clause 1, formulated as a low-zinc composition, with no added zinc ions, comprising an acylated analogue of human insulin holding the substitution B3Q.

7. The pharmaceutical composition according to clause 1, formulated as a low-zinc composition, with no added zinc ions, comprising an acylated analogue of human insulin selected from:

A22K(N(eps) tetradecanedioyl-4×gGlu), B3E, desB27, B29R, desB30 human insulin;

A22K(N(eps)-hexadecanedioyl-4×gGlu), B3E, desB27, B29R, desB30 human insulin;

A22K(N(eps)-hexadecanedioyl-gGlu-2×OEG), B3E, desB27, B29R, desB30 human insulin;

A22K(N(eps)-hexadecanedioyl-3×(gGlu-OEG)-gGlu), B3E, desB27, B29R, desB30 human insulin;

A22K(N(eps)-tetradecanedioyl-gGlu-2×OEG), B3E, desB27, B29R, desB30 human insulin;

A22K(N(eps)-pentadecanedioyl-4×gGlu), B3E, desB27, B29R, desB30 human insulin;

A22K(N(eps)-tetradecanedioyl-4×gGlu-2×OEG), B3E, desB27, B29R, desB30 human insulin;

A14E, A22K(N(eps)-tetradecanedioyl-gGlu-2×OEG), B3E, desB27, B29R, desB30 human insulin;

A14E, A22K(N(eps)-tetradecanedioyl-4×gGlu), B3E, desB27, B29R, desB30 human insulin;

A22K(N(eps)-tetradecanedioyl-2×gGlu), B3E, desB27, B29R, desB30 human insulin;

A22K(N(eps)-tetradecanedioyl-gGlu), B3E, desB27, B29R, desB30 human insulin;

and

A22K(N(eps)-tetradecanedioyl-3×gGlu), B3E, desB27, B29R, desB30 human insulin.

8. The pharmaceutical composition according to clause 1, formulated as a low-zinc composition, with no added zinc ions, comprising an acylated analogue of human insulin selected from:

A22K(N(eps)-tetradecanedioyl-4×gGlu), B3Q, desB27, B29R, desB30 human insulin;

A22K(N(eps)-hexadecanedioyl-gGlu-2×OEG), B3Q, desB27, B29R, desB30 human insulin;

A22K(N(eps)-hexadecanedioyl-3×(gGlu-OEG)-gGlu), B3Q, desB27, B29R, desB30 human insulin;

A22K(N(eps)-tetradecanedioyl-gGlu-2×OEG), B3Q, desB27, B29R, desB30 human insulin; and A22K(N(eps)-hexadecanedioyl-4×gGlu), B3Q, desB27, B29R, desB30 human insulin.

9. The pharmaceutical composition according to either one of clauses 7-8, comprising less than 0.2 $Zn^{2+}$ ions per 6 insulin molecules.

10. The low-zinc pharmaceutical composition according to either one of clauses 7-8, wherein no surfactant has been added.

11. The pharmaceutical composition according to either one of clauses 7-8, comprising a nicotinic compound.

12. The pharmaceutical composition according to either one of clauses 7-8, comprising a nicotinic compound, phenylalanine, and/or a salt thereof, in a total concentration from about 20 mM to about 170 mM.

13. The pharmaceutical composition according to either one of clauses 7-8, comprising a nicotinic compound, phenylalanine and/or a salt thereof, in a total concentration from about 130 mM to about 170 mM.

14. The pharmaceutical composition according to either one of clauses 7-8, comprising a pharmaceutically acceptable excipient, diluent and/or adjuvant.

Methods of Therapy

The present invention relates to drugs for therapeutic use. More specifically the invention relates to the use of the acylated derivatives of human insulin analogues of the invention for the treatment or prevention of medical conditions relating to diabetes.

Therefore, in another aspect, the invention provides a method for the treatment or alleviation of a disease or disorder or condition of a living animal body, including a human, which disease, disorder or condition may be selected from a disease, disorder or condition relating to diabetes, Type 1 diabetes, Type 2 diabetes, impaired glucose tolerance, hyperglycemia, dyslipidemia, obesity, metabolic syndrome (metabolic syndrome X, insulin resistance syndrome), hypertension, cognitive disorders, atherosclerosis, myocardial infarction, stroke, cardiovascular disorders, coronary heart disease, inflammatory bowel syndrome, dyspepsia, or gastric ulcers, which method comprises the step of administering to a subject in need thereof a therapeutically effective amount of the acylated analogue of human insulin of the invention.

In another embodiment the invention provides a method for the treatment or alleviation of a disease or disorder or condition of a living animal body, including a human, which disease, disorder or condition may be selected from a disease, disorder or condition relating to diabetes, Type 1 diabetes, Type 2 diabetes, impaired glucose tolerance, hyperglycemia, dyslipidemia, obesity, metabolic syndrome (metabolic syndrome X, insulin resistance syndrome), hypertension, cognitive disorders, atherosclerosis, myocardial infarction, stroke, cardiovascular disorders, coronary heart disease, inflammatory bowel syndrome, dyspepsia, or gastric ulcers, which method comprises administration to a subject in need thereof a therapeutically effective amount of the acylated analogue of human insulin of the invention.

In a third embodiment the invention provides a method for the treatment or alleviation of a disease or disorder or condition of a living animal body, including a human, which disease, disorder or condition may be selected from a disease, disorder or condition relating to diabetes, Type 1 diabetes, Type 2 diabetes, impaired glucose tolerance, hyperglycemia, dyslipidemia, obesity, or metabolic syndrome (metabolic syndrome X, insulin resistance syndrome).

In a fourth embodiment the invention provides a method for the treatment or alleviation of a disease or disorder or condition of a living animal body, including a human, which disease, disorder or condition may be selected from a disease, disorder or condition relating to diabetes, in particular Type 1 diabetes, or Type 2 diabetes.

BRIEF DESCRIPTION OF THE DRAWINGS

The present invention is further illustrated by reference to the accompanying drawing, in which:

FIG. 3b shows the resulting changes in plasma glucose originating from the insulin profiles in FIG. 3a;

EXAMPLES

Figure 1:
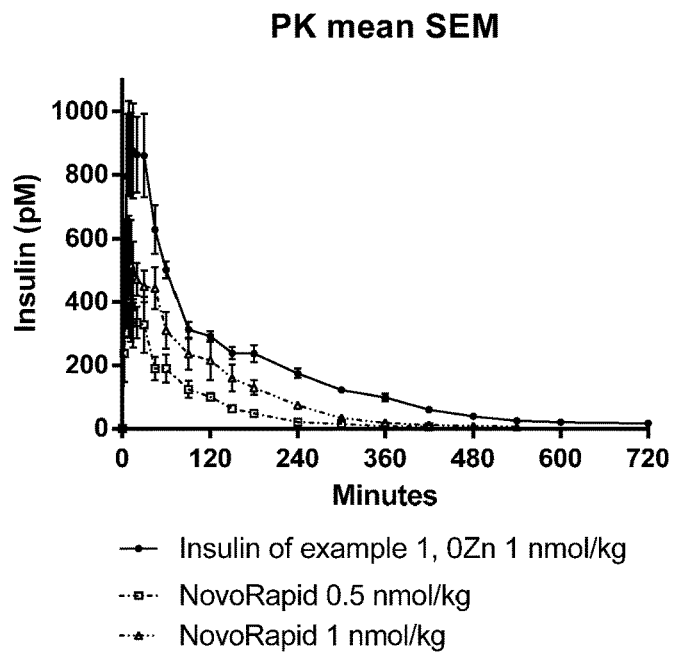
FIG. 1 shows the PK (pharmacokinetic) profile (insulin concentrations vs. time) of the insulin derivative of Example 1 formulated with 0 zinc per 6 insulin molecules (1 nmol/kg) in comparison with the profile of NovoRapid®/NovoLog® (insulin aspart, commercial formulation, 3 zinc per 6 insulin molecules (0.5 and 1 nmol/kg)
Figure 2:
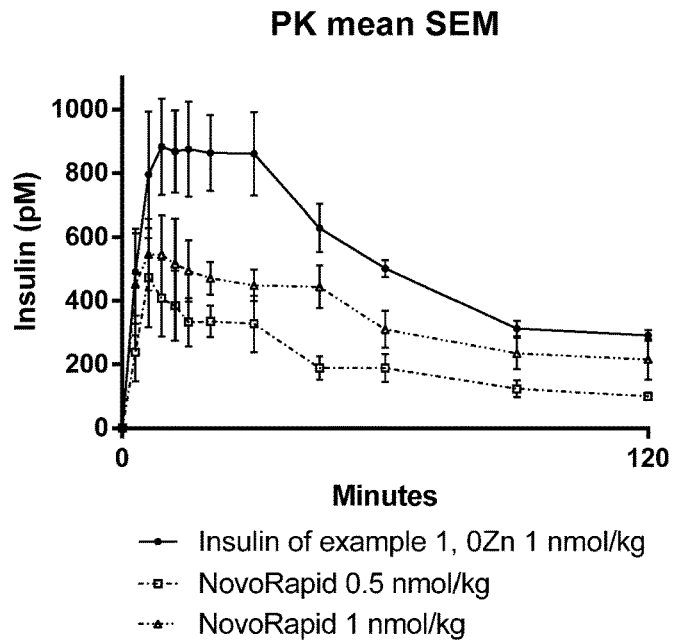
FIG. 2 shows the same data as in FIG. 1, but only the first 2 hours are shown.
Figure 3A:
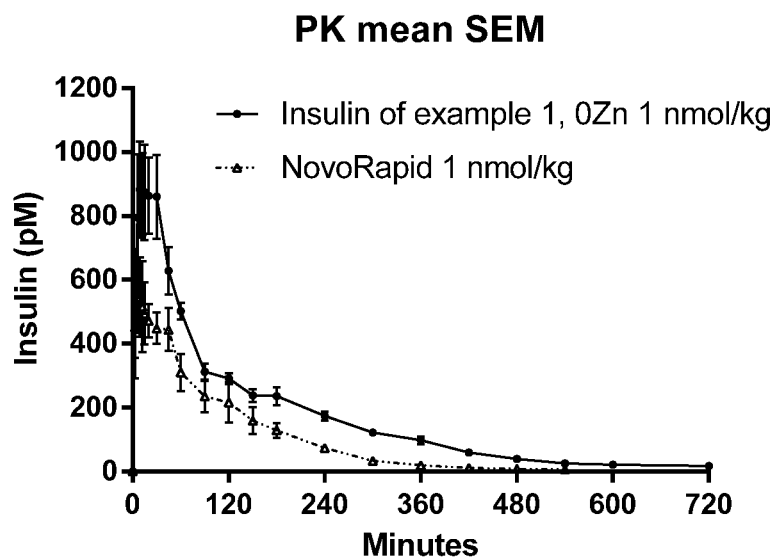
FIG. 3a shows the same data as in FIG. 1, but shows only the data for the insulin of Example 1 formulated with 0 zinc per 6 insulin molecules (1 nmol/kg) in comparison with the profile of NovoRapid®/NovoLog® (insulin aspart, commercial formulation, 3 zinc per 6 insulin molecules (1 nmol/kg)
Figure 3B:
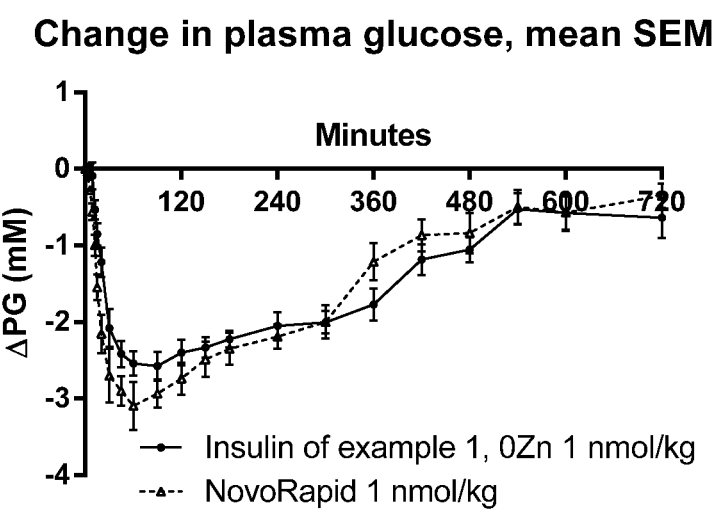

The invention is further illustrated with reference to the following examples, which are not intended to be in any way limiting to the scope of the invention as claimed.

Insulin Analogue Expression and Purification

Insulin Analogue Expression

The insulin analogue, i.e. the two-chain non-acylated insulin analogues, for use according to the invention are produced recombinantly by expressing a DNA sequence encoding the insulin analogue in question in a suitable host cell by well-known techniques, e.g. as disclosed in U.S. Pat. No. 6,500,645. The insulin analogue is either expressed directly or as a precursor molecule which may have an N-terminal extension on the B-chain and/or a connecting peptide (C-peptide) between the B-chain and the A-chain. This N-terminal extension and C-peptide are cleaved off in vitro by a suitable protease, e.g. *Achromobactor lyticus* protease (ALP) or trypsin, and will therefore have a cleavage site next to position B1 and A1, respectively. N-terminal extensions and C-peptides of the type suitable for use according to this invention are disclosed in e.g. U.S. Pat. No. 5,395,922, EP 765395 and WO 9828429.

The polynucleotide sequence encoding the insulin analogue precursor for use according to the invention may be prepared synthetically by established methods, e.g. the phosphoramidite method described by Beaucage et al. (1981) *Tetrahedron Letters* 22 1859-1869, or the method described by Matthes et al. (1984) *EMBO Journal* 3 801-805. According to the phosphoramidite method, oligonucleotides are synthesised in e.g. an automatic DNA synthesiser, purified, duplexed, and ligated to form the synthetic DNA construct. A currently preferred way of preparing the DNA construct is by polymerase chain reaction (PCR).

The recombinant method will typically make use of a vector which is capable of replicating in the selected microorganism or host cell and which carries a polynucleotide sequence encoding the insulin analogue precursor for use according to the present invention. The recombinant vector may be an autonomously replicating vector, i.e., a vector which exists as an extra-chromosomal entity, the replication of which is independent of chromosomal replication, e.g. a plasmid, an extra-chromosomal element, a mini-chromosome, or an artificial chromosome. The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used. The vector may be linear or closed circular plasmids and will preferably contain an element(s) that permits stable integration of the vector into the host cell's genome or autonomous replication of the vector in the cell independent of the genome.

The recombinant expression vector may be one capable of replicating in yeast. Examples of sequences which enable the vector to replicate in yeast are the yeast plasmid 2 μm replication genes REP 1-3 and origin of replication.

The vector may contain one or more selectable markers, which permit easy selection of trans-formed cells. A selectable marker is a gene the product, which provides for biocide or viral resistance, resistance to heavy metals, prototrophy to auxotrophs, and the like. Examples of bacterial selectable markers are the dal genes from *Bacillus subtilis* or *Bacillus licheniformis*, or markers which confer antibiotic resistance such as ampicillin, kanamycin, chloramphenicol or tetracycline resistance. Selectable markers for use in a filamentous fungal host cell include amdS (acetamidase), argB (ornithine carbamoyltransferase), pyrG (orotidine-5'-phosphate decarboxylase) and trpC (anthranilate synthase. Suitable markers for yeast host cells are ADE2, HIS3, LEU2, LYS2, MET3, TRP1, and URA3. A well suited selectable marker for yeast is the *Schizosaccharomyces pompe* TPI gene (Russell (1985) *Gene* 40 125-130).

In the vector, the polynucleotide sequence is operably connected to a suitable promoter sequence. The promoter may be any nucleic acid sequence which shows transcriptional activity in the host cell of choice including mutant, truncated, and hybrid promoters, and may be obtained from genes encoding extra-cellular or intra-cellular polypeptides either homologous or heterologous to the host cell.

Examples of suitable promoters for directing the transcription in a bacterial host cell, are the promoters obtained from the *E. coli* lac operon, *Streptomyces coelicolor* agarase gene (dagA), *Bacillus subtilis* levansucrase gene (sacB), *Bacillus licheniformis* alpha-amylase gene (amyL), *Bacillus stearothermophilus* maltogenic amylase gene (amyM), *Bacillus amyloliquefaciens* alpha-amylase gene (amyQ), and *Bacillus licheniformis* penicillinase gene (penP). Examples of suitable promoters for directing the transcription in a filamentous fungal host cell are promoters obtained from the genes for *Aspergillus oryzae* TAKA amylase, *Rhizomucor miehei* aspartic proteinase, *Aspergillus niger* neutral alpha-amylase, and *Aspergillus niger* acid stable alpha-amylase. In a yeast host, useful promoters are the *Saccharomyces cerevisiae* Mal, TPI, ADH, TDH3 or PGK promoters.

The polynucleotide sequence encoding the insulin peptide backbone for use according to the invention also will typically be operably connected to a suitable terminator. In yeast, a suitable terminator is the TPI terminator (Alber et al. (1982) *J. Mol. Appl. Genet.* 1 419-434).

The procedures used to combine the polynucleotide sequence encoding the insulin analogue for use according to the invention, the promoter and the terminator, respectively, and to insert them into a suitable vector containing the information necessary for replication in the selected host, are well known to persons skilled in the art. It will be understood that the vector may be constructed either by first preparing a DNA construct containing the entire DNA sequence encoding the insulin backbones for use according to the invention, and subsequently inserting this fragment into a suitable expression vector, or by sequentially inserting DNA fragments containing genetic information for the individual elements (such as the signal and pro-peptide (N-terminal extension of the B-chain), C-peptide, A- and B-chains), followed by ligation.

The vector comprising the polynucleotide sequence encoding the insulin analogue for use according to the invention is introduced into a host cell, so that the vector is maintained as a chromosomal integrant, or as a self-replicating extra-chromosomal vector. The term "host cell" encompasses any progeny of a parent cell that is not identical to the parent cell due to mutations that occur during replication. The host cell may be a unicellular microorganism, e.g. a prokaryote, or a non-unicellular microorganism, e.g. a eukaryote. Useful unicellular cells are bacterial cells such as gram positive bacteria including, but not limited to, a *Bacillus* cell, a *Streptomyces* cell, or a gram negative bacteria such as *E. coli* and *Pseudomonas* sp. Eukaryote cells may be mammalian, insect, plant, or fungal cells.

The host cell may in particular be a yeast cell. The yeast organism may be any suitable yeast organism which, on cultivation, secretes the insulin peptide backbone or the precursor hereof into the culture medium. Examples of suitable yeast organisms are include strains selected from *Saccharomyces cerevisiae, Saccharomyces kluyveri, Schizosaccharomyces pombe, Sacchoromyces uvarum, Kluyveromyces lactis, Hansenula polymorpha, Pichia pastoris, Pichia methanolica, Pichia kluyveri, Yarrowia lipolytica, Candida* sp.*, Candida utilis, Candida cacaoi, Geotrichum* sp.*,* and *Geotrichum fermentans*.

The transformation of the yeast cells may for instance be effected by protoplast formation followed by transformation by known methods. The medium used to cultivate the cells may be any conventional medium suitable for growing yeast organisms.

Insulin Analogue Purification

The secreted insulin analogue or precursor hereof may be recovered from the medium by conventional procedures including separating the yeast cells from the medium by centrifugation, by filtration or by catching or adsorbing the insulin analogue or precursor hereof on an ion exchange matrix or on a reverse phase absorption matrix, precipitating the proteinaceous components of the supernatant, or by filtration by means of a salt, e.g. ammonium sulphate, followed by purification by a variety of chromatographic procedures, e.g. ion exchange chromatography, affinity chromatography, etc.

The purification and digestion of the insulin peptide backbones of this invention is carried out as follows:

The single-chain insulin analogue precursor, which may contain an N-terminal extension of the B-chain and a modified C-peptide between the B-chain and the A-chain, is purified and concentrated from the yeast culture supernatant by cation exchange (Kjeldsen et al. (1998) *Prot. Expr. Pur.* 14 309-316).

The single-chain insulin analogue precursor is matured into two-chain insulin peptide backbone by digestion with lysine-specific immobilised ALP (Kristensen et al. (1997) *J. Biol. Chem.* 20 12978-12983) or by use of trypsin to cleave off the N-terminal extension of the B-chain, if present, and the C-peptide.

Trypsin Digestion

The eluate from the cation exchange chromatography step containing the insulin analogue precursor is diluted with water to an ethanol concentration of 15-20%. Glycine is added to a concentration of 50 mM and pH is adjusted to 9.0-9.5 by NaOH. Trypsin is added in a proportion of 1:300 (w:w) and digestion is allowed to proceed at 4 degrees. The digestion is analytically monitored every 20 minutes until digestion is completed. The digestion is terminated with addition of 1 M citric acid in a proportion of 3:100 (volume: volume).

The digestion reaction is analysed by analytical LC on a Waters Acquity Ultra-Performance Liquid Chromatography system using a C18 column and the molecular weight is confirmed by MALDI-TOF MS (Bruker Daltonics Autoflex II TOF/TOF).

The two-chain insulin analogue is purified by reversed phase HPLC (Waters 600 system) on a C18 column using an acetonitrile gradient. The desired insulin analogue, e.g. A22K, desB27, B29R, desB30 human insulin, A22K, B3E, desB27, B29R, desB30 human insulin, or A22K, B3Q, desB27, B29R, desB30 human insulin is recovered by lyophilisation.

Purity is determined by analytical LC on a Waters Acquity Ultra-Performance Liquid Chromatography system using a C18 column, and the molecular weight is confirmed by MALDI-TOF MS.

Abbreviations

ALP—Achromobacter *lyticus* protease
C-peptide—connecting peptide
HPLC—high-performance liquid chromatography
IR—insulin receptor
IGF-1R insulin-like growth factor 1 receptor
LC—liquid chromatography
MALDI-TOF—matrix-assisted laser desorption ionisation time-of-flight
MS—mass spectrometry
PCR—polymerase chain reaction
PD—pharmacodynamics (blood/plasma glucose lowering effect)
PG—plasma glucose
PK—pharmacodynamics (blood/plasma insulin concentrations versus time profiles)
tBu is tert-butyl;
DCM is dichloromethane;
DIC is diisopropylcarbodiimide;
DIPEA=DIEA is N,N-disopropylethylamine;
DMF is N,N-dimethylformamide;
DMSO is dimethyl sulphoxide;
EtOAc is ethyl acetate;
Fmoc is 9-fluorenylmethyloxycarbonyl;
γGlu (gGlu) is gamma L-glutamyl;
HCl is hydrochloric acid;
HOBt is 1-hydroxybenzotriazole;
NMP is N-methylpyrrolidone;
MeCN is acetonitrile;
OEG is [2-(2-aminoethoxy)ethoxy]ethylcarbonyl;
Su is succinimidyl-1-yl=2,5-dioxo-pyrrolidin-1-yl;
OSu is succinimidyl-1-yloxy=2,5-dioxo-pyrrolidin-1-yloxy;
RPC is reverse phase chromatography;
RT is room temperature;
TCTU is O-(6-chloro-benzotriazol-1-yl)-N,N,N',N'-tetramethyluronium tetrafluoroborate;
TFA is trifluoroacetic acid;
THF is tetrahydrofuran;
TNBS is 2,4,6-trinitrobenzenesulfonic acid;
TRIS is tris(hydroxymethyl)aminomethane; and
TSTU is O—(N-succinimidyl)-1,1,3,3-tetramethyluronium tetrafluoroborate.

General Remarks

The following examples and general procedures refer to intermediate compounds and final products identified in the specification and in the synthesis schemes. The preparation of the compounds of the present invention is described in detail using the following examples, but the chemical reactions described are disclosed in terms of their general applicability to the preparation of compounds of the invention.

Occasionally, the reaction may not be applicable as described to each compound included within the disclosed scope of the invention. The compounds for which this occurs will be readily recognised by those skilled in the art. In these cases the reactions can be successfully performed by conventional modifications known to those skilled in the art, i.e. by appropriate protection of interfering groups, by changing to other conventional reagents, or by routine modification of reaction conditions.

Alternatively, other reactions disclosed herein or otherwise conventional will be applicable to the preparation of the corresponding compounds of the invention. In all preparative methods, all starting materials are known or may easily be prepared from known starting materials. All temperatures are set forth in degrees Celsius and unless otherwise indicated, all parts and percentages are by weight when referring to yields and all parts are by volume when referring to solvents and eluents.

The compounds of the invention can be purified by employing one or more of the following procedures which are typical within the art. These procedures can—if needed—be modified with regard to gradients, pH, salts, concentrations, flow, columns and so forth. Depending on factors such as impurity profile, solubility of the insulins in question etcetera, these modifications can readily be recognised and made by a person skilled in the art.

After acidic HPLC or desalting, the compounds are isolated by lyophilisation of the pure fractions.

After neutral HPLC or anion exchange chromatography, the compounds are desalted, precipitated at isoelectrical pH, or purified by acidic HPLC.

Typical Purification Procedures

RP-HPLC System:

Gilson system consisting of the following: Liquid handler Model 215, Pump Model 322-H2 and UV Detector Model 155 (UV 215 nm and 280 nm).

Anion Exchange and Desalting System:
Äkta Explorer system consists of the following: Pump Model P-900, UV detector Model UV-900 (UV 214, 254 and 280 nm), pH and conductivity detector Model pH/C-900, Fraction collector Model Frac-950.
Acidic RP-HPLC:
Column: Phenomenex Gemini, 5 µM 5u C18 110 Å, 30×250 mm
Flow: 20 mL/min
Buffer A: 0.1% TFA in water
Buffer B: 0.1% TFA in acetonitrile
Neutral RP-HPLC:
Column: Phenomenex Gemini, 5 µM 5u C18 110 Å, 30×250 mm
Flow: 20 mL/min
Buffer A: 10 mM Tris, 15 mM $(NH_4)_2SO_4$, pH=7.3, 20% acetonitrile in milliQ
Buffer B: 20% milliQ in acetonitrile
Anion Exchange Chromatography:
Column-material: Poros50HQ or Source30Q
Flow: column dependent
Buffer A: 15 mM Tris, 25 mM $NH_4OAc$, 50% EtOH, pH=7.5.
Buffer B: 15 mM Tris, 500 mM $NH_4OAc$, 50% EtOH, pH=7.5.
Desalting:
Column: HiPrep 26/10 another (or the same) Fmoc protected amino acid and deprotection. The synthetic sequence is terminated by coupling of mono-tert-butyl protected fatty (α, ω) diacids, like hexadecanedioic, pentadecanedioic, or tetradecanedioic acid mono-tert-butyl esters.

Cleavage of the compounds from the resin is accomplished using diluted acid like 0.5-5% TFA/DCM (trifluoroacetic acid in dichloromethane), acetic acid (e.g. 10% in DCM, or HOAc/trifluoroethanol/DCM 1:1:8), or hexafluoroisopropanol in DCM (see e.g. F. Z. Dörwald: *Organic Synthesis on Solid Phase*; Wiley-VCH 2000, ISBN 3-527-29950-5; N. Sewald & H.-D. Jakubke: *Peptides: Chemistry and Biology*; Wiley-VCH, 2002, ISBN 3-527-30405-3; or *The Combinatorial Chemistry Catalog*, 1999, Novabiochem AG, and references cited therein). This ensures that tert-butyl esters present in the compounds as carboxylic acid protecting groups are not deprotected.

Finally, the C-terminal carboxy group (liberated from the resin) is activated, e.g., as the N-hydroxysuccinimide ester (OSu). This activated ester is deprotected, e.g. using neat TFA, and used either directly or after purification (crystallisation) as coupling reagent in attachment to parent insulins of the invention. This procedure is illustrated below.
Example Illustrating a General Procedure for Synthesis of Acylation Reagent on Solid Phase: Synthesis of Tetradecanedioyl-4×gGlu-OSu (Chem.4)

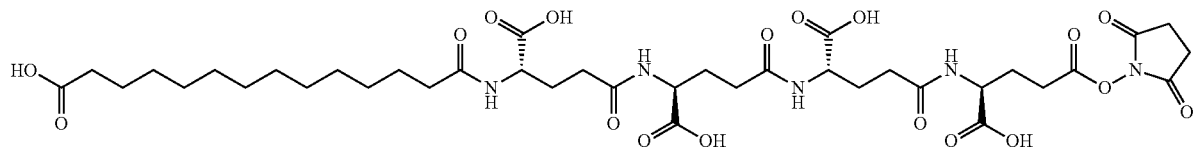 [SMILES: O=C(O)CCCCCCCCCCCCC(=O)N[C@@H](CCC(=O)N[C@@H](CCC(=O)N[C@@H](CCC(=O)N[C@@H](CCC(=O)ON1C(=O)CCC1=O)C(=O)O)C(=O)O)C(=O)O)C(=O)O]

Flow: 20 mL/min
Buffer A: 0.1% TFA in water
Buffer B: 0.1% TFA in acetonitrile

Acylation reagents were synthesized either in solution (see below) or on solid phase as described in e.g. WO 2009/115469.
General Procedure for the Solid Phase Synthesis of Acylation Reagents of the General Formula III

[Acyl]-[Linker]-Act wherein the Acyl and Linker groups are as defined above, and Act is the leaving group of an active ester, such as N-hydroxysuccinimide (OSu), or 1-hydroxybenzotriazole, and
wherein carboxylic acids within the Acyl and Linker moieties of the acyl moiety are protected as tert-butyl esters.

Compounds of the general Formula III may be synthesised on solid support using procedures in the art of solid phase peptide synthesis known to the skilled person.

One such procedure comprises attachment of a Fmoc protected amino acid to a polystyrene 2-chlorotritylchloride resin. The attachment may be accomplished using the free N-protected amino acid in the presence of a tertiary amine, like triethyl amine or N,N-diisopropylethylamine (see references below). The C-terminal end (which is attached to the resin) of this amino acid is at the end of the synthetic sequence being coupled to the parent insulins of the invention.

After attachment of the Fmoc amino acid to the resin, the Fmoc group is deprotected using, e.g., secondary amines, like piperidine or diethyl amine, followed by coupling of 2-Chlorotrityl resin 100-200 mesh 1.5 mmol/g (15.79 g, 23.69 mmol) was left to swell in dry dichloromethane (150 mL) for 20 minutes. A solution of Fmoc-Glu-OtBu (6.72 g, 15.79 mmol) and N,N-diisopropylethylamine (10.46 mL, 60.01 mmol) in dry dichloromethane (120 mL) was added to resin and the mixture was shaken for 16 hrs. Resin was filtered and treated with a solution of N,N-diisopropylethylamine (5.5 mL, 31.59 mmol) in methanol/dichloromethane mixture (9:1, 150 mL, 5 min). Then resin was washed with N,N-dimethylformamide (2×150 mL), dichloromethane (2×150 mL) and N,N-dimethylformamide (2×150 mL).

Fmoc group was removed by treatment with 20% piperidine in N,N-dimethylformamide (2×150 mL, 1×5 min, 1×20 min). Resin was washed with N,N-dimethylformamide (2×150 mL), 2-propanol (2×150 mL), dichloromethane (2×150 mL) and N,N-dimethylformamide (2×150 mL). Solution of Fmoc-Glu-OtBu (10.08 g, 23.69 mmol), O-(6-chloro-benzotriazol-1-yl)-N,N,N',N'-tetramethyluronium tetrafluoroborate (TCTU, 8.42 g, 23.69 mmol) and N,N-diisopropylethylamine (7.43 mL, 42.64 mmol) in N,N-dimethylformamide (120 mL) was added to resin and mixture was shaken for 16 hr. Resin was filtered and treated with a solution of N,N-diisopropylethylamine (5.5 mL, 31.59 mmol) in methanol/dichloromethane mixture (9:1, 150 mL, 5 min). Then resin was washed with N,N-dimethylformamide (2×150 mL), dichloromethane (2×150 mL) and N,N-dimethylformamide (2×150 mL).

Fmoc group was removed by treatment with 20% piperidine in N,N-dimethylformamide (2×150 mL, 1×5 min, 1×20 min). Resin was washed with N,N-dimethylformamide (2×150 mL), 2-propanol (2×150 mL), dichloromethane (2×150 mL) and N,N-dimethylformamide (2×150 mL). Solution of Fmoc-Glu-OtBu (10.08 g, 23.69 mmol), O-(6-chloro-benzotriazol-1-yl)-N,N,N',N'-tetramethyluronium tetrafluoroborate (TCTU, 8.42 g, 23.69 mmol) and N,N-diisopropylethylamine (7.43 mL, 42.64 mmol) in N,N-dimethylformamide (120 mL) was added to resin and mixture was shaken for 16 hr. Resin was filtered and treated with a solution of N,N-diisopropylethylamine (5.5 mL, 31.59 mmol) in methanol/dichloromethane mixture (9:1, 150 mL, 5 min). Then resin was washed with N,N-dimethylformamide (2×150 mL), dichloromethane (2×150 mL) and N,N-dimethylformamide (2×150 mL).

Fmoc group was removed by treatment with 20% piperidine in N,N-dimethylformamide (2×150 mL, 1×5 min, 1×20 min). Resin was washed with N,N-dimethylformamide (2×150 mL), 2-propanol (2×150 mL), dichloromethane (2×150 mL) and N,N-dimethylformamide (2×150 mL). Solution of Fmoc-Glu-OtBu (10.08 g, 23.69 mmol), O-(6-chloro-benzotriazol-1-yl)-N,N,N',N∝-tetramethyluronium tetrafluoroborate (TCTU, 8.42 g, 23.69 mmol) and N,N-diisopropylethylamine (7.43 mL, 42.64 mmol) in N,N-dimethylformamide (120 mL) was added to resin and mixture was shaken for 16 hr. Resin was filtered and treated with a solution of N,N-diisopropylethylamine (5.5 mL, 31.59 mmol) in methanol/dichloromethane mixture (9:1, 150 mL, 5 min). Then resin was washed with N,N-dimethylformamide (2×150 mL), dichloromethane (2×150 mL) and N,N-dimethylformamide (2×150 mL).

Fmoc group was removed by treatment with 20% piperidine in N,N-dimethylformamide (2×150 mL, 1×5 min, 1×20 min). Resin was washed with N,N-dimethylformamide (2×150 mL), 2-propanol (2×150 mL), dichloromethane (2×150 mL) and N,N-dimethylformamide (2×150 mL). Solution of tetradecanedioic acid mono-tert-butyl ester (7.45 g, 23.69 mmol), O-(6-chloro-benzotriazol-1-yl)-N,N,N',N'-tetramethyluronium tetrafluoroborate (TCTU, 8.42 g, 23.69 mmol) and N,N-diisopropylethylamine (7.43 mL, 42.64 mmol) in the mixture of N,N-dimethylformamide (40 mL) and dichloromethane (80 mL) was added to resin and mixture was shaken for 16 hr. Resin was filtered and washed with dichloromethane (2×150 mL), N,N-dimethylformamide (2×150 mL), methanol (2×150 mL) and dichloromethane (10×150 mL).

The product was cleaved from the resin by the treatment with trifluoroethanol (150 mL) overnight. Resin was filtered off and washed with dichloromethane (3×100 mL). The solvent was removed under reduced pressure. The residue was purified by column chromatography on silica gel (gradient elution dichloromethane/methanol 100:0 to 95:5) giving titled compound as white solid.

Product was dried in vacuo to yield (S)-2-((S)-4-tert-Butoxycarbonyl-4-{(S)-4-tert-butoxycarbonyl-4-[(S)-4-tert-butoxycarbonyl-4-(13-tert-butoxycarbonyl-tridecanoylamino)-butyrylamino]-butyrylamino}-butyrylamino)-pentanedioic acid 1-tert-butyl ester.

Yield: 14.77 g (89%).

$^1$H NMR spectrum (300 MHz, CDCl$_3$, δH): 7.22 (d, J=7.7 Hz, 1H); 6.97 (d, J=7.9 Hz, 1H); 6.72 (d, J=7.9 Hz, 1H); 6.41 (d, J=7.9 Hz, 1H); 4.59-4.43 (m, 4H); 2.49-2.13 (m, 16H); 2.06-1.72 (m, 4H); 1.70-1.52 (m, 4H); 1.52-1.38 (m, 45H); 1.35-1.21 (m, 16H).

LC-MS purity: 100% (ELSD).

LC-MS Rt (Sunfire 4.6 mm×100 mm, acetonitrile/water 50:50 to 100:0+0.1% FA): 7.39 min.

LC-MS m/z: 1055.0 (M+H)+.

The obtained tert-butyl protected tetradecanedioyl-4× gGlu-OH ((S)-2-((S)-4-tert-Butoxycarbonyl-4-{(S)-4-tert-butoxycarbonyl-4-[(S)-4-tert-butoxycarbonyl-4-(13-tert-butoxycarbonyl-tridecanoylamino)-butyrylamino]-butyrylamino}-butyrylamino)-pentanedioic acid 1-tert-butyl ester) was dissolved in tetrahydrofuran. DIPEA was added followed by TSTU dissolved in acetonitrile. The reaction mixture was stirred for 3 h and then evaporated in vacuo, re-dissolved in ethyl acetate, washed with 0.1M HCl (aq), dried over MgSO$_4$, filtered and evaporated in vacuo. LC-MS (electrospray): m/z=1174.7 (M+Na$^+$). Calc: 1175.4.

The protected and OSu-activated compound was dissolved in 10 mL TFA and stirred at room temperature overnight. Diethyl ether was added and the precipitate formed was filtered off and dried on vacuum overnight to afford (S)-2-((S)-4-Carboxy-4-{(S)-4-carboxy-4-[(S)-4-carboxy-4-(13-carboxy-tridecanoylamino)-butyrylamino]-butyrylamino}-butyrylamino)-pentanedioic acid 5-(2,5-dioxo-pyrrolidin-1-yl) ester (tetradecanedioyl-4×gGlu-OSu). LC-MS (electrospray): m/z=872.2 (M+H$^+$). Calc: 871.9.

Example Illustrating a General Procedure for Synthesis of Acylation Reagent on Solid Phase: Synthesis of Tetradecanedioyl-gGlu-2×OEG-OSu (Chem.5)

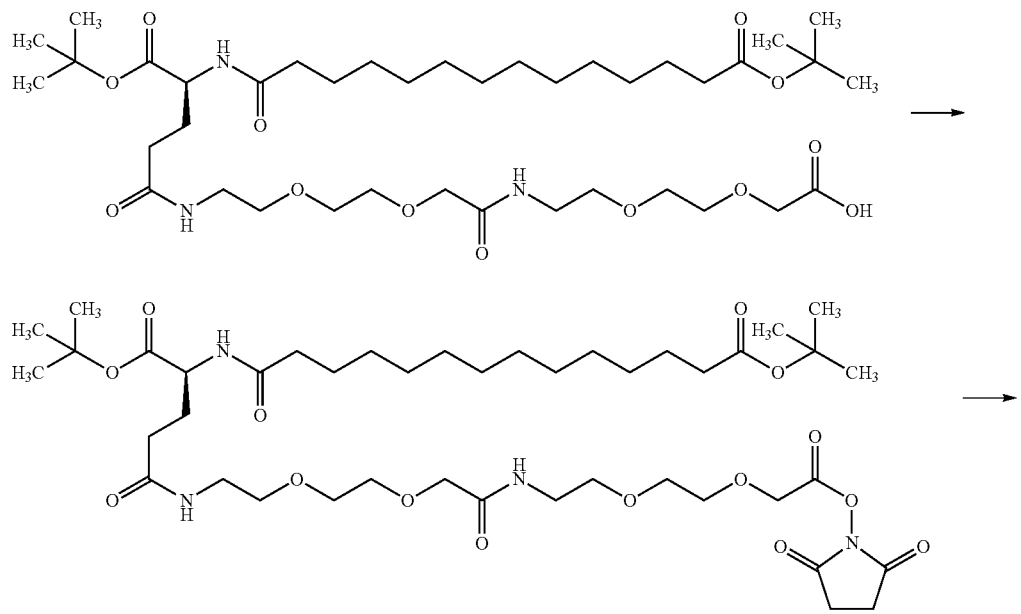

-continued

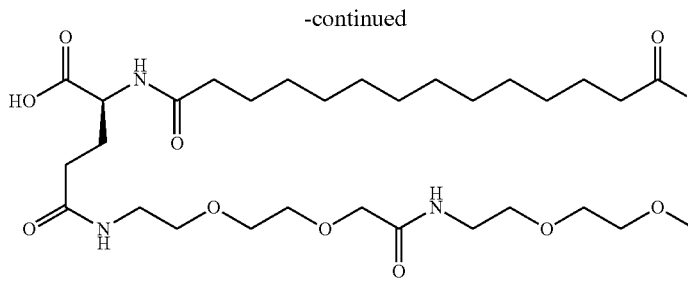

13-{(S)-1-tert-Butoxycarbonyl-3-[2-(2-{[2-(2-carboxymethoxy-ethoxy)-ethylcarbamoyl]-methoxy}-ethoxy)-ethylcarbamoyl]-propylcarbamoyl}-tridecanoic acid tert-butyl ester 2-Chlorotrityl resin 100-200 mesh 1.7 mmol/g (79.8 g, 135.6 mmol) was left to swell in dry dichloromethane (450 mL) for 20 minutes. A solution of {2-[2-(9H-fluoren-9-ylmethoxycarbonylamino)-ethoxy]-ethoxy}-acetic acid (Fmoc-OEG-OH, 34.9 g, 90.4 mmol) and N,N-diisopropylethylamine (59.9 mL, 343.6 mmol) in dry dichloromethane (100 mL) was added to resin and the mixture was shaken for 4 hrs. Resin was filtered and treated with a solution of N,N-diisopropylethylamine (31.5 mL, 180.8 mmol) in methanol/dichloromethane mixture (4:1, 150 mL, 2×5 min). Then resin was washed with N,N-dimethylformamide (2×300 mL), dichloromethane (2×300 mL) and N,N-dimethylformamide (3×300 mL). Fmoc group was removed by treatment with 20% piperidine in dimethylformamide (1×5 min, 1×30 min, 2×300 mL). Resin was washed with N,N-dimethylformamide (3×300 mL), 2-propanol (2×300 mL) and dichloromethane (350 mL, 2×300 mL).

Solution of {2-[2-(9H-fluoren-9-ylmethoxycarbonylamino)-ethoxy]-ethoxy}-acetic acid (Fmoc-OEG-OH, 52.3 g, 135.6 mmol), O-(6-chloro-benzotriazol-1-yl)-N,N,N',N' tetramethyluronium tetrafluoroborate (TCTU, 48.2 g, 135.6 mmol) and N,N-diisopropylethylamine (42.5 mL, 244.1 mmol) in N,N-dimethylformamide (250 mL) was added to resin and mixture was shaken for 2 hr. Since ninhydrin test was still positive, resin was filtered and treated with the same amounts of reagents for another 30 minutes. Resin was filtered and washed with N,N-dimethylformamide (2×300 mL), dichloromethane (2×300 mL) and N,N-dimethylformamide (3×300 mL). Fmoc group was removed by treatment with 20% piperidine in dimethylformamide (1×5 min, 1×30 min, 2×300 mL). Resin was washed with N,N-dimethylformamide (3×300 mL), 2-propanol (2×300 mL) and dichloromethane (350 mL, 2×300 mL).

Solution of (S)-2-(9H-fluoren-9-ylmethoxycarbonylamino)-pentanedioic acid 1-tert-butyl ester (Fmoc-LGlu-OtBu, 57.7 g, 135.6 mmol), O-(6-chloro-benzotriazol-1-yl)-N,N,N',N'-tetramethyluronium tetrafluoroborate (TCTU, 48.2 g, 135.6 mmol) and N,N-diisopropylethylamine (42.5 mL, 244.1 mmol) in N,N-dimethylformamide (250 mL) was added to resin and mixture was shaken for 1 hr. Resin was filtered and washed with N,N-dimethylformamide (2×300 mL), dichloromethane (2×300 mL) and N,N-dimethylformamide (2×300 mL). Fmoc group was removed by treatment with 20% piperidine in dimethylformamide (1×5 min, 1×30 min, 2×300 mL). Resin was washed with N,N-dimethylformamide (3×300 mL), 2-propanol (2×300 mL) and dichloromethane (350 mL, 2×300 mL).

Solution of tetradecanedioic acid mono-tert-butyl ester (C14(OtBu)-OH, 42.7 g, 135.6 mmol), O-(6-chloro-benzotriazol-1-yl)-N,N,N',N'-tetramethyluronium tetrafluoroborate (TCTU, 48.2 g, 135.6 mmol) and N,N-diisopropylethylamine (42.5 mL, 244.1 mmol) in dichloromethane/N,N-dimethylformamide mixture (4:1, 300 mL) was added to resin and mixture was shaken for 1.5 hr. Resin was filtered and washed with N,N-dimethylformamide (6×300 mL), dichloromethane (4×300 mL), methanol (4×300 mL) and dichloromethane (7×600 mL). The product was cleaved from resin by treatment with 2,2,2-trifluoroethanol (600 mL) for 18 hrs. Resin was filtered off and washed with dichloromethane (4×300 mL), dichloromethane/2-propanol mixture (1:1, 4×300 mL), 2-propanol (2×300 mL) and dichloromethane (6×300 mL). Solutions were combined; solvent evaporated and crude product was purified by column chromatography (Silicagel 60A, 0.060-0.200 mm; eluent: dichloromethane/methanol 1:0-9:1).

Pure 13-{(S)-1-tert-Butoxycarbonyl-3-[2-(2-{[2-(2-carboxymethoxy-ethoxy)-ethylcarbamoyl]-methoxy}-ethoxy)-ethylcarbamoyl]-propylcarbamoyl}-tridecanoic acid tert-butyl ester was dried in vacuo and obtained as orange oil.

Yield: 55.2 g (77%).
RF (SiO$_2$, dichloromethane/methanol 9:1): 0.35.
1H NMR spectrum (300 MHz, CDCl$_3$, δH): 7.37 (bs, 1H); 7.02 (bs, 1H); 6.53 (d, J=7.9 Hz, 1H); 4.54-4.38 (m, 1H); 4.17 (s, 2H); 4.02 (s, 2H); 3.82-3.40 (m, 16H); 2.37-2.12 (m, 7H); 2.02-1.82 (m, 1H); 1.71-1.51 (m, 4H); 1.47 (s, 9H); 1.43 (s, 9H); 1.25 (bs, 16H).
LC-MS purity: 100%.
LC-MS Rt (Sunfire 4.6 mm×100 mm, acetonitrile/water 70:30 to 100:0+0.1% FA): 3.93 min.
LC-MS m/z: 791.0 (M+H)+.

13-{(S)-1-tert-Butoxycarbonyl-3-[2-(2-{[2-(2-carboxymethoxy-ethoxy)-ethylcarbamoyl]-methoxy}-ethoxy)-ethylcarbamoyl]-propylcarbamoyl}-tridecanoic acid tert-butyl ester (tetradecanedioyl-gGlu-2×OEG-OH, 8.89 g, 11.3 mmol)) was dissolved in 100 mL of acetonitrile, and TSTU (4.07 g, 13.5 mmol) and DIPEA (2.35 mL, 13.5 mmol) were added to the stirred solution and the mixture was stirred at room temperature for 1 hour. The solvent was evaporated and the residue was dissolved in dichloromethane and washed twice with 0.05M HCl.

The organic phase was dried (MgSO$_4$) and evaporated in vacuo. This afforded 9.98 g (100%) of 13-((S)-1-tert-Butoxycarbonyl-3-{2-[2-({2-[2-(2,5-dioxo-pyrrolidin-1-yloxycarbonylmethoxy)-ethoxy]-ethylcarbamoyl}-methoxy)-ethoxy]-ethylcarbamoyl}-propylcarbamoyl)-tridecanoic acid tert-butyl ester as an oil.

13-((S)-1-tert-Butoxycarbonyl-3-{2-[2-({2-[2-(2,5-dioxo-pyrrolidin-1-yloxycarbonylmethoxy)-ethoxy]-ethylcarbamoyl}-methoxy)-ethoxy]-ethylcarbamoyl}-propylcarbamoyl)-tridecanoic acid tert-butyl ester (4 g) was dissolved in trifluoroacetic acid (10 mL) and the mixture was stirred at room temperature for 1 hour and evaporated in vacuo. The residue was dissolved in dichloromethane (10 mL) and evaporated in vacuo. Addition of cold diethyl ether (10 mL) resulted in precipitation of a white greasy solid. This was isolated by decantation and was dried in vacuo. This afforded 3.4 g (quant.) of 14-[[(1S)-1-carboxy-4-[2-[2-[2-[2-[2-[2-(2,5-dioxopyrrolidin-1-yl)oxy-2-oxoethoxy]ethoxy]ethylamino]-2-oxoethoxy]ethoxy]ethylamino]-4-oxobutyl]amino]-14-oxotetradecanoic acid (tetradecanedioyl-gGlu-2×OEG-OSu), which was stored at −18° C.

LC-MS (electrospray): m/z=775.33; calc: 774.8.

Acylation and Purification of Insulin Derivatives

A general procedure (A) for the acylation and purification of the insulin derivatives of the invention is described in Example 1, below. This procedure has also been applied to the synthesis of the compounds of Examples 2-25, below. Purification using other methods (as described above) have also been done for some of these derivatives.

Example 1; General Procedure (A)

A22K(N(Eps)-Tetradecanedioyl-4×gGlu), desB27, B29R, desB30 Human Insulin

IUPAC (OpenEye, IUPAC style) name: N{Alpha}([ArgB29],des-ThrB27,ThrB30-Insulin(human)-(A)-peptidyl)-N{Epsilon}[(4S)-4-carboxy-4-[[(4S)-4-carboxy-4-[[(4S)-4-carboxy-4-[[(4S)-4-carboxy-4-(13-carboxytridecanoylamino)butanoyl]amino]butanoyl]amino]butanoyl]amino]butanoyl]Lys,(B)-peptide.

A22K, desB27, B29R, desB30 human insulin (2.0 g) was dissolved in 40 mL 0.1M Na$_2$CO$_3$ (aq), and pH adjusted to 11.2 with 1M NaOH (aq). Tetradecanedioyl-4×gGlu-OSu (0.454 g) was dissolved in 2 mL DMF and added drop wise to the insulin solution while keeping pH at a constant 11.2 with 1M NaOH (aq). The reaction mixture was stirred at room temperature for 30 min, then neutralized to pH=7.5 using 0.1M HCl (aq) and diluted with 1:1 EtOH/milliQ water.

The resulting insulin was purified by anion exchange chromatography on a Poros50HQ 74 mL column, eluting with a 25 to 500 mM ammonium acetate in 15 mM Tris, 50 v/v % ethanol, pH 7.5 (acetic acid). Desalting of pure fractions was performed on a reverse phase column eluting with a gradient of acetonitrile in milliQ water containing 0.1% trifluoroacetic acid. The resulting pure insulin was lyophilized. LC-MS (electrospray): m/z=1629.98 (M+4)/4. Calc: 1630.65.

The acylation reagent, tetradecanedioyl-4×gGlu-OSu, was synthesized as described above.

Example 2; General Procedure (A)

A22K(N(Eps)-Tetradecanedioyl-4×gGlu), B3E, desB27, B29R, desB30 Human Insulin

IUPAC (OpenEye, IUPAC style) name: N{Alpha}([GluB3,ArgB29],des-ThrB27,ThrB30-Insulin(human)-(A)-peptidyl)-N{Epsilon}[(4S)-4-carboxy-4-[[(4S)-4-carboxy-4-[[(4S)-4-carboxy-4-[[(4S)-4-carboxy-4-(13-carboxytridecanoylamino)butanoyl]amino]butanoyl]amino]butanoyl]Lys,(B)-peptide.

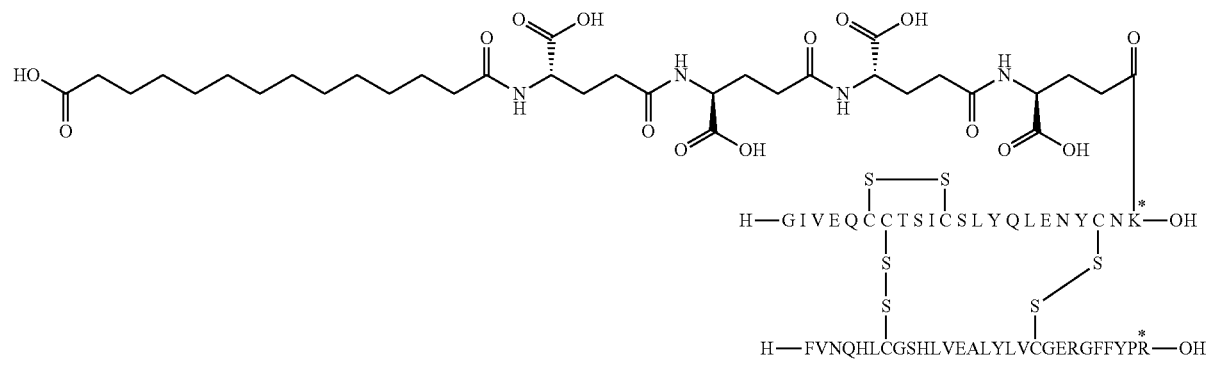

(SEQ ID NO: 1 and SEQ ID NO: 3)

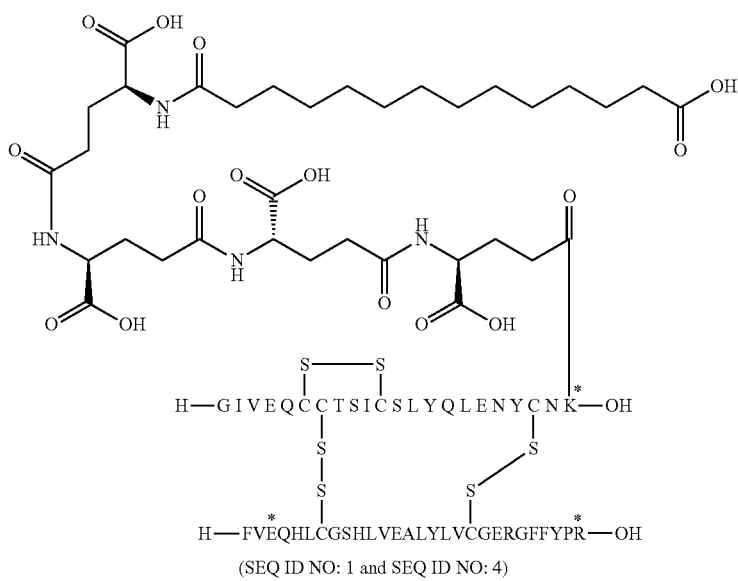

(SEQ ID NO: 1 and SEQ ID NO: 4)

This analogue was prepared according to the method described in Example 1.

LC-MS (electrospray): m/z=1633.9 (M+4H$^+$). Calc: 1634.4

Example 3; General Procedure (A)

A14E, A22K(N(Eps)-Tetradecanedioyl-4×gGlu), desB27, B29R, desB30 Human Insulin

IUPAC (OpenEye, IUPAC style) name: N{Alpha}([GluA14,ArgB29],des-ThrB27,ThrB30-Insulin(human)-(A)-peptidyl)-N{Epsilon}[(4S)-4-carboxy-4-[[(4S)-4-carboxy-4-[[(4S)-4-carboxy-4-[[(4S)-4-carboxy-4-(13-carboxytridecanoylamino)butanoyl]-amino]butanoyl]amino]butanoyl]amino]butanoyl]Lys,(B)-peptide.

LC-MS (electrospray): m/z=1622.2 (M+4)/4. Calc: 1622.1

Example 4; General Procedure (A)

A22K(N(Eps)-Hexadecanedioyl-4×gGlu), B3E, desB27, B29R, desB30 Human Insulin

IUPAC (OpenEye, IUPAC style) name: N{Alpha}([GluB3,ArgB29],des-ThrB27,ThrB30-Insulin(human)-(A)-peptidyl)-N{Epsilon}[(4S)-4-carboxy-4-[[(4S)-4-carboxy-4-[[(4S)-4-carboxy-4-[[(4S)-4-carboxy-4-[[(4S)-4-carboxy-4-(15-carboxypentadecanoylamino)butanoyl]amino]butanoyl]amino]butanoyl]amino]butanoyl]Lys,(B)-peptide.

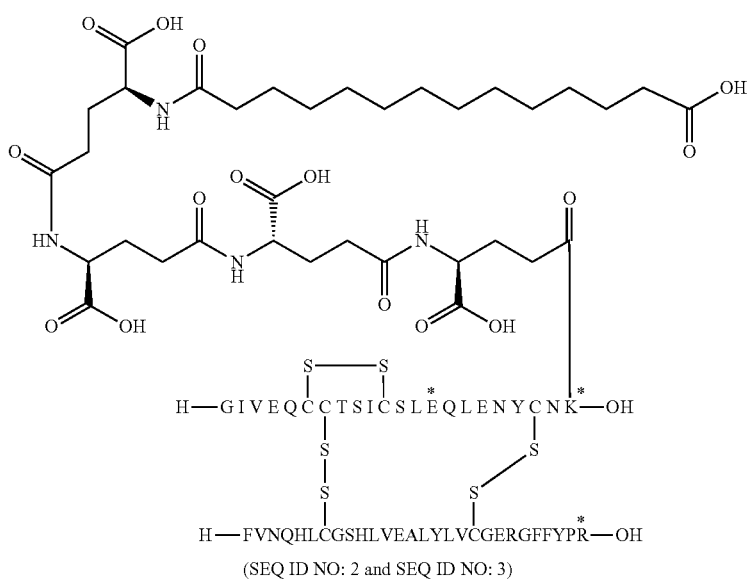

(SEQ ID NO: 2 and SEQ ID NO: 3)

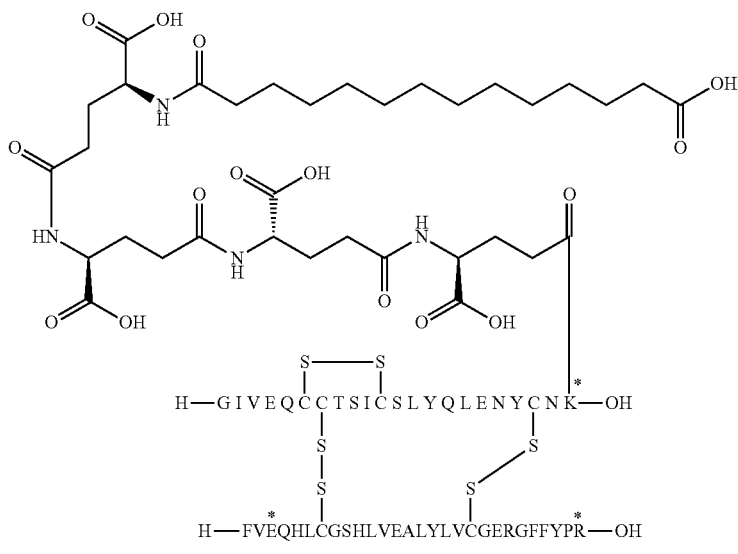

(SEQ ID NO: 1 and SEQ ID NO: 4)

LC-MS (electrospray): m/z=1641.2 (M+4H$^+$). Calc: 1641.4.

Example 5; General Procedure (A)

A22K(N(Eps)-Hexadecanedioyl-gGlu-2×OEG), B3E, desB27, B29R, desB30 Human Insulin IUPAC (OpenEye, IUPAC style) name: N{Alpha}([GluB3, ArgB29],des-ThrB27,ThrB30-Insulin(human)-(A)-peptidyl)-N{Epsilon}[2-[2-[2-[[2-[2-[2-[[(4S)-4-carboxy-4-(15-carboxypentadecanoylamino)butanoyl]amino]ethoxy] ethoxy]acetyl]amino]ethoxy]-ethoxy]acetyl]Lys,(B)-peptide.

LC-MS (electrospray): m/z=1616.6 (M+4)/4. Calc: 1617.1

Example 6; General Procedure (A)

A22K(N(Eps)-Hexadecanedioyl-3×(gGlu-OEG)-gGlu), B3E, desB27, B29R, desB30 Human Insulin IUPAC (OpenEye, IUPAC style) name: N{Alpha}([GluB3, ArgB29],des-ThrB27,ThrB30-Insulin(human)-(A)-peptidyl)-N{Epsilon}[(4S)-4-carboxy-4-[[2-[2-[2-[[(4S)-4-carboxy-4-[[2-[2-[2-[[(4S)-4-carboxy-4-[[2-[2-[2-[[(4S)-4-carboxy-4-(15-carboxypentadecanoylamino)butanoyl]-amino]ethoxy]ethoxy]acetyl]amino]butanoyl]amino] ethoxy]ethoxy]acetyl]amino]butanoyl]-amino]ethoxy] ethoxy]acetyl]amino]butanoyl]Lys,(B)-peptide.

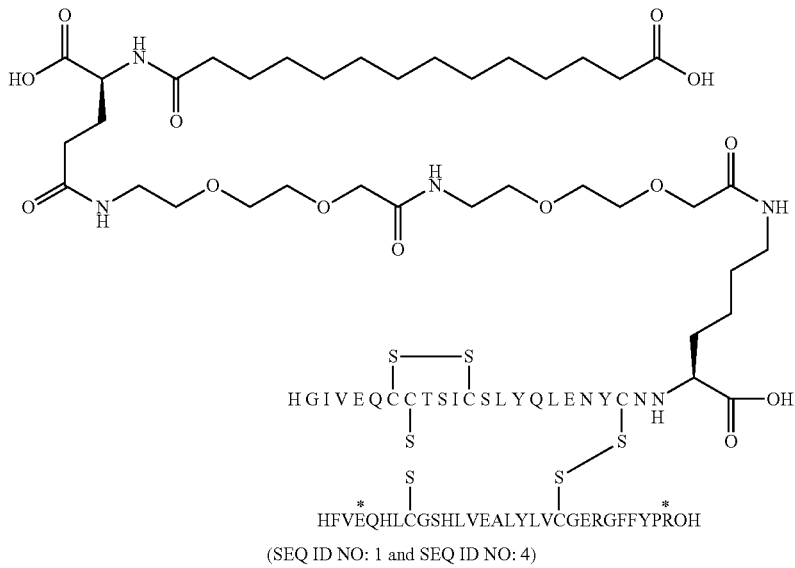

(SEQ ID NO: 1 and SEQ ID NO: 4)

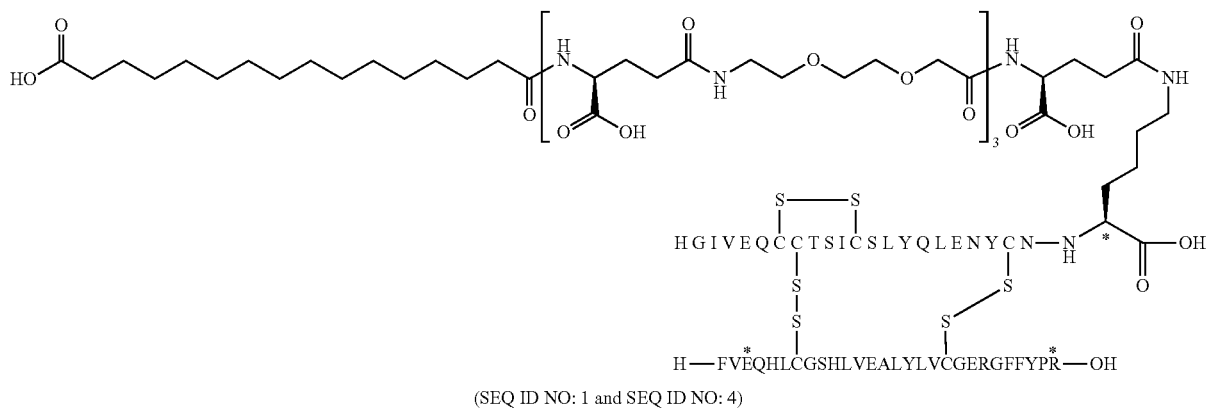

(SEQ ID NO: 1 and SEQ ID NO: 4)

LC-MS (electrospray): m/z=1749.9 (M+4)/4. Calc: 1750.3

Example 7; General Procedure (A)

A22K(N(Eps)-Tetradecanedioyl-4×gGlu), B3Q, desB27, B29R, desB30 Human Insulin

IUPAC (OpenEye, IUPAC style) name: N{Alpha}([GlnB3, ArgB29],des-ThrB27,ThrB30-Insulin(human)-(A)-peptidyl)-N{Epsilon}[(4S)-4-carboxy-4-[[(4S)-4-carboxy-4-[[(4S)-4-carboxy-4-[[(4S)-4-carboxy-4-(13-carboxytridecanoylamino)butanoyl]amino]butanoyl]amino]butanoyl]amino]butanoyl]Lys,(B)-peptide.

LC-MS (electrospray): m/z=1634.2 (M+4)/4. Calc: 1633.1

Example 8; General Procedure (A)

A22K(N(Eps)-Hexadecanedioyl-gGlu-2×OEG), B3Q, desB27, B29R, desB30 Human Insulin IUPAC (OpenEye, IUPAC style) name: N{Alpha}([GlnB3, ArgB29],des-ThrB27,ThrB30-Insulin(human)-(A)-peptidyl)-N{Epsilon}[2-[2-[2-[[2-[2-[2-[[(4S)-4-carboxy-4-(15-carboxypentadecanoylamino)butanoyl]amino]ethoxy]ethoxy]acetyl]amino]ethoxy]ethoxy]-acetyl]Lys,(B)-peptide.

(SEQ ID NO: 1 and SEQ ID NO: 5)

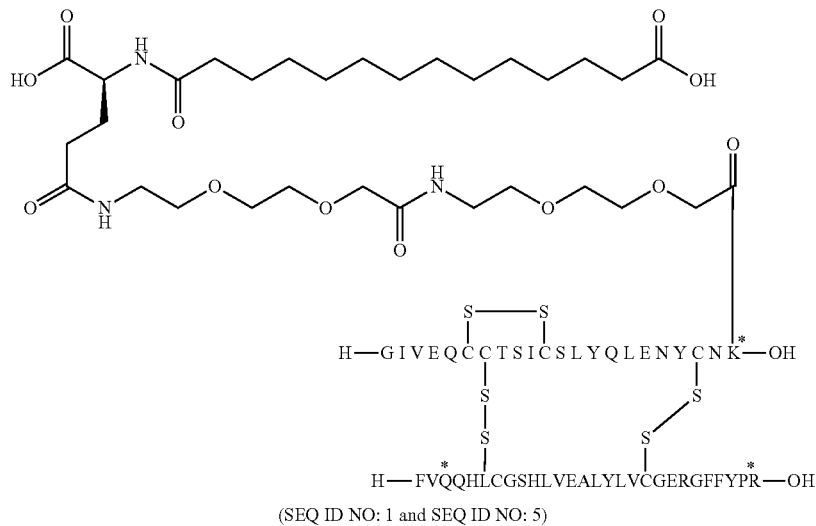

(SEQ ID NO: 1 and SEQ ID NO: 5)

LC-MS (electrospray): m/z=1616.6 (M+4)/4. Calc: 1615.8.

Example 9; General Procedure (A)

A22K(N(Eps)-Hexadecanedioyl-3×(gGlu-OEG)-gGlu), B3Q, desB27, B29R, desB30 Human Insulin IUPAC (OpenEye, IUPAC style) name: N{Alpha}([GlnB3,ArgB29],des-ThrB27,ThrB30-Insulin(human)-(A)-peptidyl)-N{Epsilon}[(4S)-4-carboxy-4-[[2-[2-[2-[[(4S)-4-carboxy-4-[[2-[2-[2-[[(4S)-4-carboxy-4-[[2-[2-[2-[[(4S)-4-carboxy-4-(15-carboxypentadecanoylamino)butanoyl] amino]ethoxy]ethoxy]acetyl] amino]butanoyl]amino]ethoxy]ethoxy]acetyl]amino]butanoyl] amino]ethoxy]ethoxy]acetyl] amino]butanoyl]Lys,(B)-peptide.

LC-MS (electrospray): m/z=1749.8 (M+4)/4. Calc: 1748.5

Example 10; General Procedure (A)

A22K(N(Eps)-Tetradecanedioyl-2×gGlu), desB27, B29R, desB30 Human Insulin

IUPAC (OpenEye, IUPAC style) name: N{Alpha}([ArgB29],des-ThrB27,ThrB30-Insulin(human)-(A)-peptidyl)-N{Epsilon}[(4S)-4-carboxy-4-[[(4S)-4-carboxy-4-(13-carboxytridecanoylamino)butanoyl]amino]butanoyl]Lys,(B)-peptide.

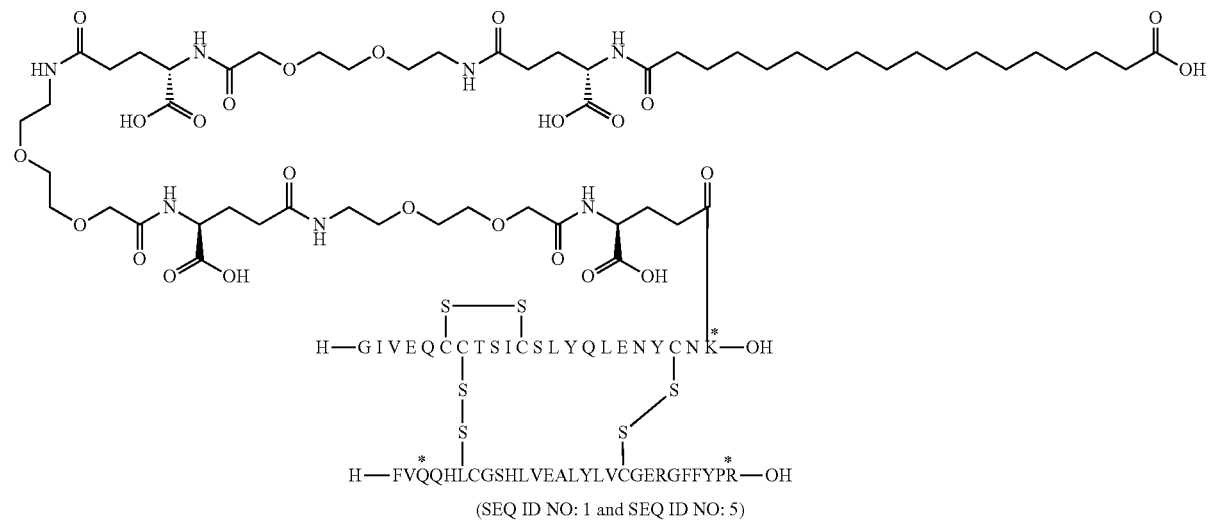

(SEQ ID NO: 1 and SEQ ID NO: 5)

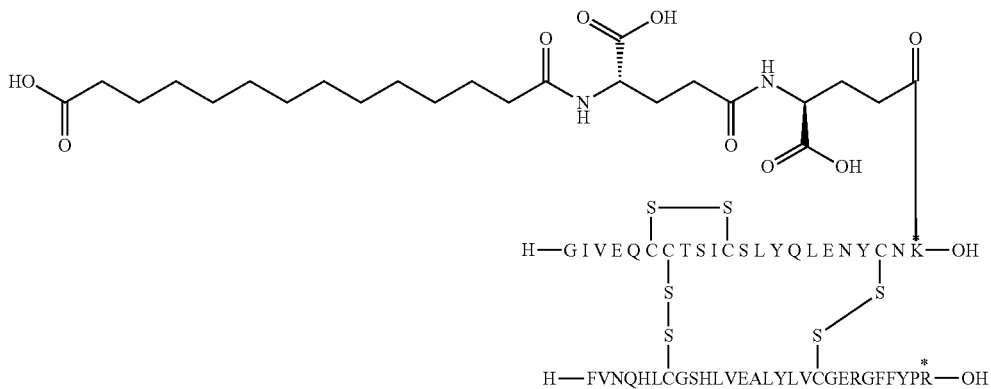

(SEQ ID NO: 1 and SEQ ID NO: 3)

LC-MS (electrospray): m/z=1565.6 (M+4)/4. Calc: 1566.1

Example 11; General Procedure (A)

A22K(N(eps)-hexadecanedioyl-4×gGlu), desB27, B29R, desB30 human insulin

IUPAC (OpenEye, IUPAC style) name: N{Alpha}([ArgB29],des-ThrB27,ThrB30-Insulin(human)-(A)-peptidyl)-N{Epsilon}[(4S)-4-carboxy-4-[[(4S)-4-carboxy-4-[[(4S)-4-carboxy-4-[[(4S)-4-carboxy-4-(15-carboxypentadecanoylamino)butanoyl]amino]butanoyl]-amino]butanoyl]amino]butanoyl]Lys,(B)-peptide.

LC-MS (electrospray): m/z=1637.4 (M+4)/4. Calc: 1636.6

Example 12; General Procedure (A)

A22K(N(Eps)-Hexadecanedioyl-gGlu-2×OEG), desB27, B29R, desB30 Human Insulin

IUPAC (OpenEye, IUPAC style) name: N{Alpha}([ArgB29],des-ThrB27,ThrB30-Insulin(human)-(A)-peptidyl)-N{Epsilon}[2-[2-[2-[[2-[2-[2-[[(4S)-4-carboxy-4-(15-carboxypentadecanoylamino)butanoyl]amino]ethoxy]ethoxy]acetyl]amino]ethoxy]ethoxy]-acetyl]Lys,(B)-peptide.

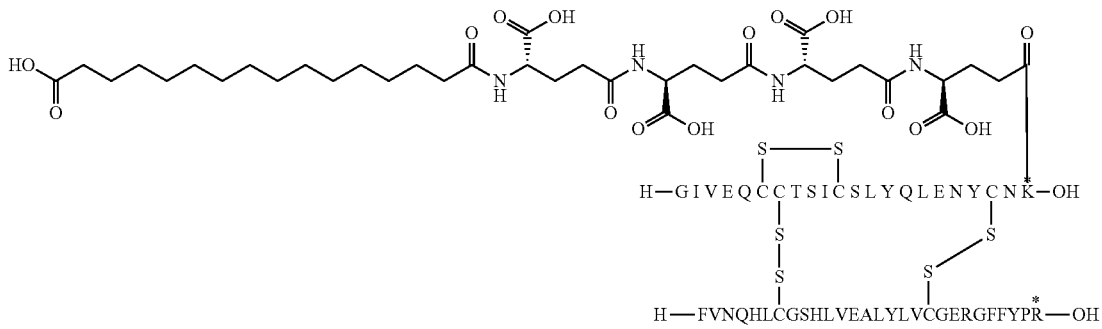

(SEQ ID NO: 1 and SEQ ID NO: 3)

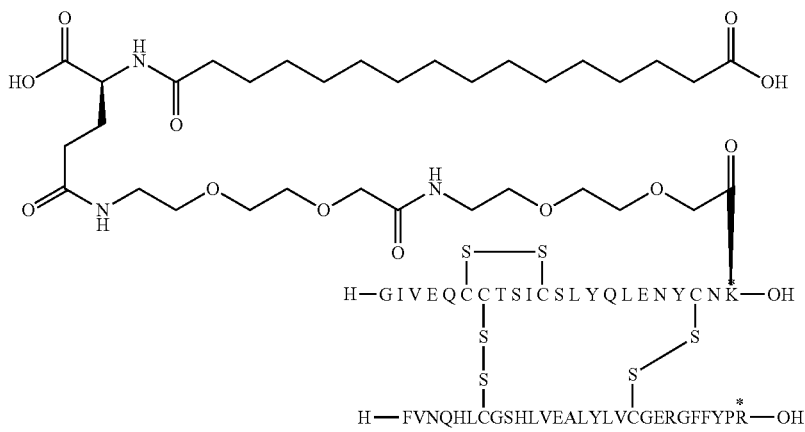

(SEQ ID NO: 1 and SEQ ID NO: 3)

LC-MS (electrospray): m/z=1613.2 (M+4)/4. Calc: 1613.4

Example 13; General Procedure (A)

A22K(N(Eps)-Hexadecanedioyl-3×(gGlu-OEG)-gGlu), desB27, B29R, desB30 Human Insulin IUPAC (OpenEye, IUPAC style) name: N{Alpha}([ArgB29],des-ThrB27,ThrB30-Insulin(human)-(A)-peptidyl)-N{Epsilon}[(4S)-4-carboxy-4-[[2-[2-[2-[[(4S)-4-carboxy-4-[[2-[2-[2-[[(4S)-4-carboxy-4-[[2-[2-[2-[[(4S)-4-carboxy-4-(15-carboxypentadecanoylamino) butanoyl]amino]ethoxy]ethoxy]acetyl]amino]butanoyl]amino]ethoxy]ethoxy]acetyl]amino]-butanoyl]amino]ethoxy]ethoxy]acetyl]amino]butanoyl]Lys,(B)-peptide.

LC-MS (electrospray): m/z=1746.4 (M+4)/4. Calc: 1746.5.

Example 14; General Procedure (A)

A22K(N(Eps)-Tetradecanedioyl-gGlu), desB27, B29R, desB30 Human Insulin

IUPAC (OpenEye, IUPAC style) name: N{Alpha}([ArgB29],des-ThrB27,ThrB30-Insulin(human)-(A)-peptidyl)-N{Epsilon}[(4S)-4-carboxy-4-(13-carboxytridecanoylamino) butanoyl]Lys,(B)-peptide.

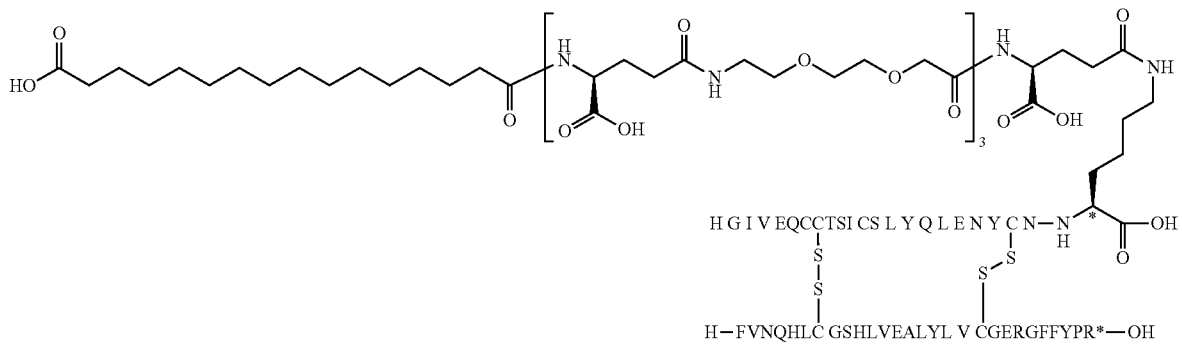

(SEQ ID NO: 1 and SEQ ID NO: 3)

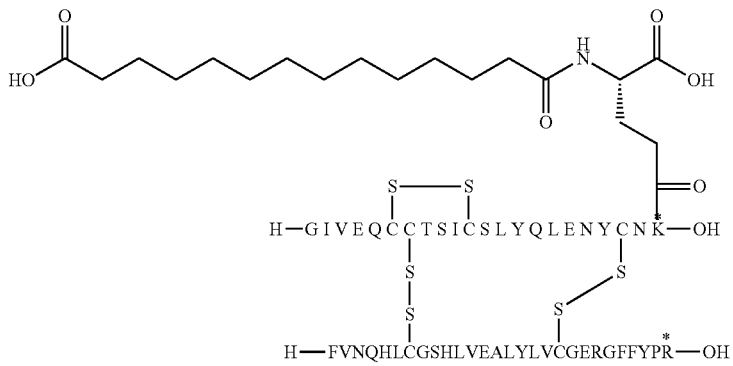

(SEQ ID NO: 1 and SEQ ID NO: 3)

LC-MS (electrospray): m/z=1533.2 (M+4)/4. Calc: 1533.8

Example 15; General Procedure (A)

A22K(N(Eps)-Tetradecanedioyl-gGlu-2×OEG), B3E, desB27, B29R, desB30 Human Insulin IUPAC (OpenEye, IUPAC style) name: N{Alpha}([GluB3, ArgB29],des-ThrB27,ThrB30-Insulin(human)-(A)-peptidyl)-N{Epsilon}[2-[2-[2-[[2-[2-[2-[[(4S)-4-carboxy-4-(13-carboxytridecanoylamino)butanoyl]amino]ethoxy]ethoxy]acetyl]amino]ethoxy]ethoxy]-acetyl]Lys,(B)-peptide.

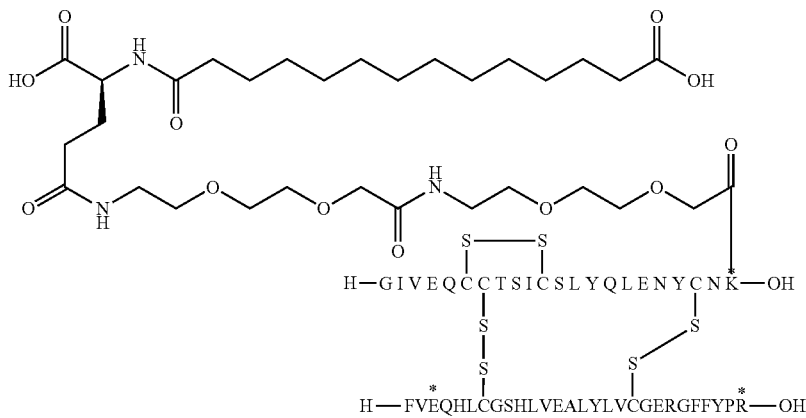

(SEQ ID NO: 1 and SEQ ID NO: 4)

LC-MS (electrospray): m/z=1610.7 (M+4)/4. Calc: 1610.1

Example 16; General Procedure (A)

A22K(N(Eps)-Tetradecanedioyl-gGlu-2×OEG), B3Q, desB27, B29R, desB30 Human Insulin IUPAC (OpenEye, IUPAC style) name: N{Alpha}([GlnB3, ArgB29],des-ThrB27,ThrB30-Insulin(human)-(A)-peptidyl)-N{Epsilon}[2-[2-[2-[[2-[2-[2-[[(4S)-4-carboxy-4-(13-carboxytridecanoylamino)butanoyl]amino]ethoxy]ethoxy]acetyl]amino]ethoxy]ethoxy]-acetyl]Lys,(B)-peptide.

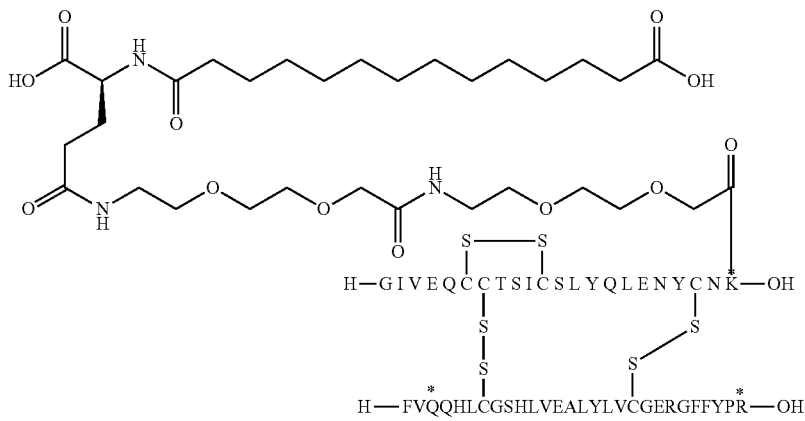

(SEQ ID NO: 1 and SEQ ID NO: 5)

LC-MS (electrospray): m/z=1609.7 (M+4)/4. Calc: 1609.9

Example 17; General Procedure (A)

A22K(N(Eps)-Tetradecanedioyl-2×OEG), desB27, B29R, desB30 Human Insulin

IUPAC (OpenEye, IUPAC style) name: N{Alpha}([ArgB29],des-ThrB27,ThrB30-Insulin(human)-(A)-peptidyl)-N{Epsilon}[2-[2-[2-[[2-[2-[2-[[(4S)-4-carboxy-4-(13-carboxytridecanoylamino)butanoyl]amino]ethoxy]ethoxy]acetyl]amino]ethoxy]ethoxy]-acetyl]Lys,(B)-peptide.

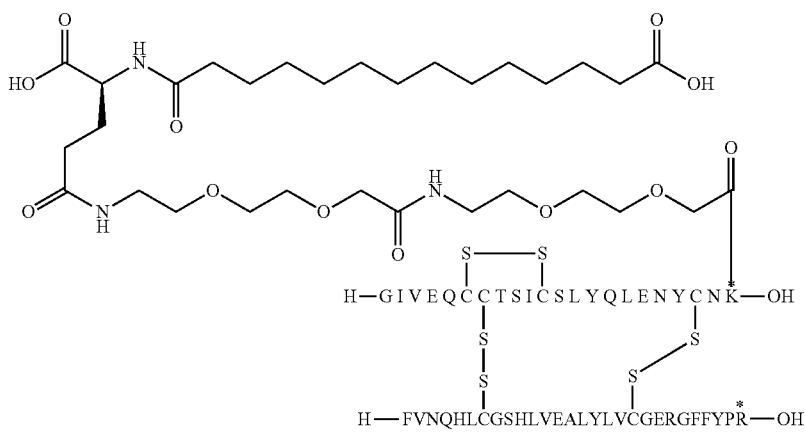

(SEQ ID NO: 1 and SEQ ID NO: 3)

LC-MS (electrospray): m/z=1606.3 (M+4)/4. Calc: 1606.4

Example 18; General Procedure (A)

A22K(N(Eps)-Hexadecanedioyl-4×gGlu), B3Q, desB27, B29R, desB30 Human Insulin

IUPAC (OpenEye, IUPAC style) name: N{Alpha}([GlnB3,ArgB29],des-ThrB27,ThrB30-Insulin(human)-(A)-peptidyl)-N{Epsilon}[(4S)-4-carboxy-4-[[(4S)-4-carboxy-4-[[(4S)-4-carboxy-4-[[(4S)-4-carboxy-4-(15-carboxypentadecanoylamino)butanoyl]amino]butanoyl]amino]butanoyl]amino]butanoyl]Lys,(B)-peptide.

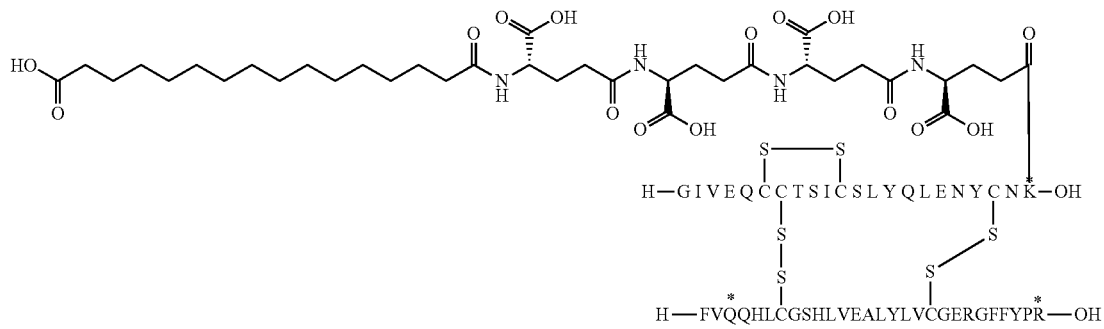

(SEQ ID NO: 1 and SEQ ID NO: 5)

LC-MS (electrospray): m/z=1640.9 (M+4)/4. Calc: 1641.1

Example 19; General Procedure (A)

A22K(N(Eps)-Pentadecanedioyl-4×gGlu), B3E, desB27, B29R, desB30 Human Insulin

IUPAC (OpenEye, IUPAC style) name: N{Alpha}([GluB3, ArgB29],des-ThrB27,ThrB30-Insulin(human)-(A)-peptidyl)-N{Epsilon}[(4S)-4-carboxy-4-[[(4S)-4-carboxy-4-[[(4S)-4-carboxy-4-[[(4S)-4-carboxy-4-(14-carboxytetradecanoylamino)butanoyl]amino]butanoyl]amino]butanoyl]amino]butanoyl]Lys,(B)-peptide.

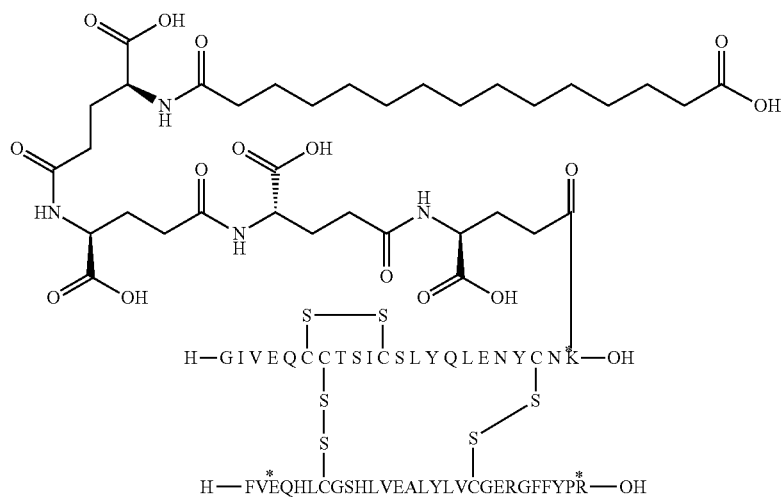

(SEQ ID NO: 1 and SEQ ID NO: 4)

LC-MS (electrospray): m/z=1637.63 (M+4)/4. Calc: 1636.76

Example 20; General Procedure (A)

A22K(N(Eps)-Tetradecanedioyl-4×gGlu-2×OEG), desB27, B29R, desB30 Human Insulin

IUPAC (OpenEye, IUPAC style) name: N{Alpha}([ArgB29],des-ThrB27,ThrB30-Insulin(human)-(A)-peptidyl)-N{Epsilon}[2-[2-[2-[[2-[2-[2-[[(4S)-4-carboxy-4-[[(4S)-4-carboxy-4-[[(4S)-4-carboxy-4-[[(4S)-4-carboxy-4-(13-carboxytridecanoylamino)butanoyl]amino]-butanoyl]amino]butanoyl]amino]ethoxy]ethoxy]acetyl]amino]ethoxy]-ethoxy]acetyl]Lys,(B)-peptide.

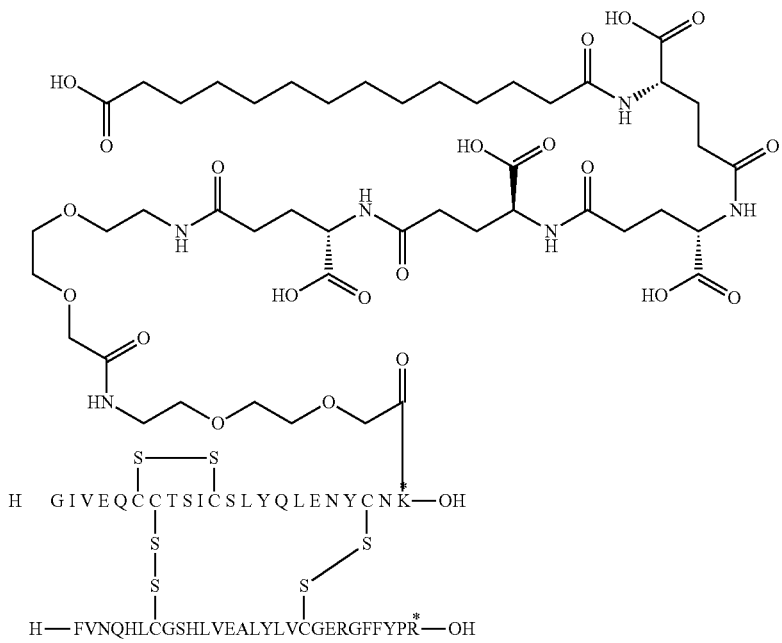

(SEQ ID NO: 1 and SEQ ID NO: 3)

LC-MS (electrospray): m/z=1703.0 (M+4)/4. Calc: 1703.2

Example 21; General Procedure (A)

A22K(N(Eps)-Tetradecanedioyl-4×gGlu-2×OEG), B3E, desB27, B29R, desB30 Human Insulin IUPAC (OpenEye, IUPAC style) name: N{Alpha}([GluB3, ArgB29],des-ThrB27,ThrB30-Insulin(human)-(A)-peptidyl)-N{Epsilon}[2-[2-[2-[[2-[2-[2-[[(4S)-4-carboxy-4-[[(4S)-4-carboxy-4-[[(4S)-4-carboxy-4-[[(4S)-4-carboxy-4-(13-carboxytridecanoylamino)butanoyl]amino]-butanoyl]amino]butanoyl]amino]butanoyl]amino]ethoxy]ethoxy]acetyl]amino]ethoxy]ethoxy]-acetyl]Lys,(B)-peptide.

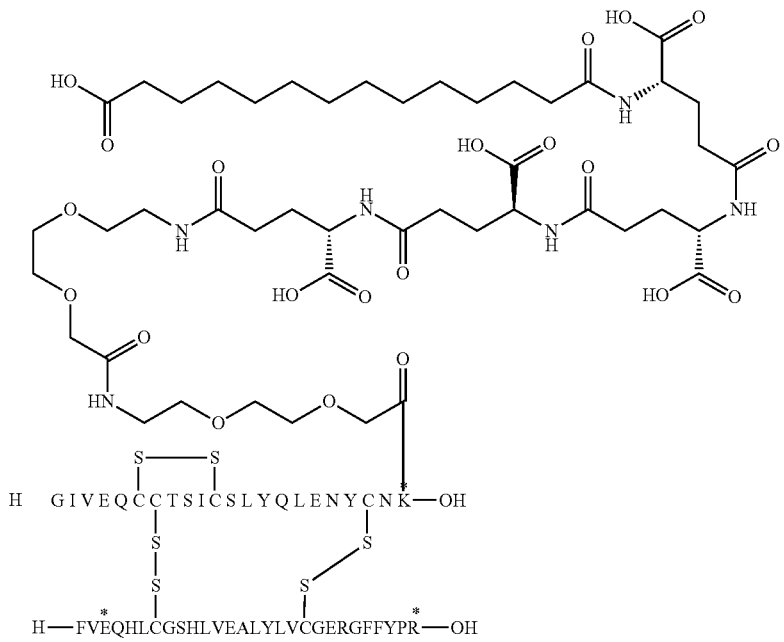

(SEQ ID NO: 1 and SEQ ID NO: 4)

LC-MS (electrospray): m/z=1706.6 (M+4)/4. Calc: 1707.0

Example 22; General Procedure (A)

A14E,
A22K(N(Eps)-Tetradecanedioyl-gGlu-2×OEG),
B3E, desB27, B29R, desB30 Human Insulin IUPAC (OpenEye, IUPAC style) name: N{Alpha}([GluA14,GluB3,ArgB29],des-ThrB27,ThrB30-Insulin(human)-(A)-peptidyl)-N{Epsilon}[2-[2-[2-[[2-[2-[2-[[(4S)-4-carboxy-4-(13-carboxytridecanoylamino)butanoyl]amino]ethoxy]ethoxy]acetyl]amino]ethoxy]ethoxy]-acetyl]Lys,(B)-peptide.

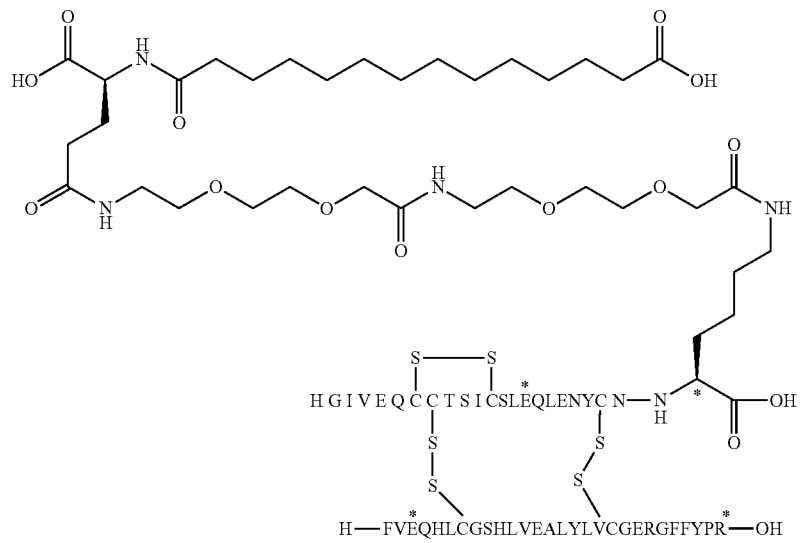

(SEQ ID NO: 2 and SEQ ID NO: 4)

LC-MS (electrospray): m/z=1601.9 (M+4)/4. Calc: 1601.6

Example 23; General Procedure (A)

A14E, A22K(N(Eps)-Tetradecanedioyl-4×gGlu),
B3E, desB27, B29R, desB30 Human Insulin IUPAC (OpenEye, IUPAC style) name: N{Alpha}([GluA14,GluB3,ArgB29],des-ThrB27,ThrB30-Insulin(human)-(A)-peptidyl)-N{Epsilon}[(4S)-4-carboxy-4-[[(4S)-4-carboxy-4-[[(4S)-4-carboxy-4-[[(4S)-4-carboxy-4-(13-carboxytridecanoylamino)butanoyl]amino]-butanoyl]amino]butanoyl]amino]butanoyl]Lys,(B)-peptide.

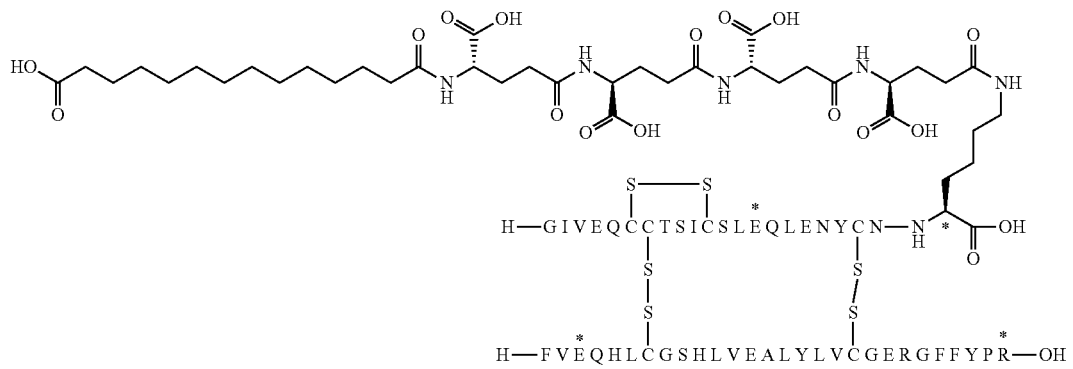

(SEQ ID NO: 2 and SEQ ID NO: 4)

LC-MS (electrospray): m/z=1625.9 (M+4)/4. Calc: 1625.8

Example 24; General Procedure (A)

A22K(N(Eps)-Tetradecanedioyl-2×gGlu), B3E, desB27, B29R, desB30 Human Insulin

IUPAC (OpenEye, IUPAC style) name: N{Alpha}([GluB3, ArgB29],des-ThrB27,ThrB30-Insulin(human)-(A)-peptidyl)-N{Epsilon}[(4S)-4-carboxy-4-[[(4S)-4-carboxy-4-(13-carboxy-tridecanoylamino)butanoyl]amino]butanoyl]Lys, (B)-peptide.

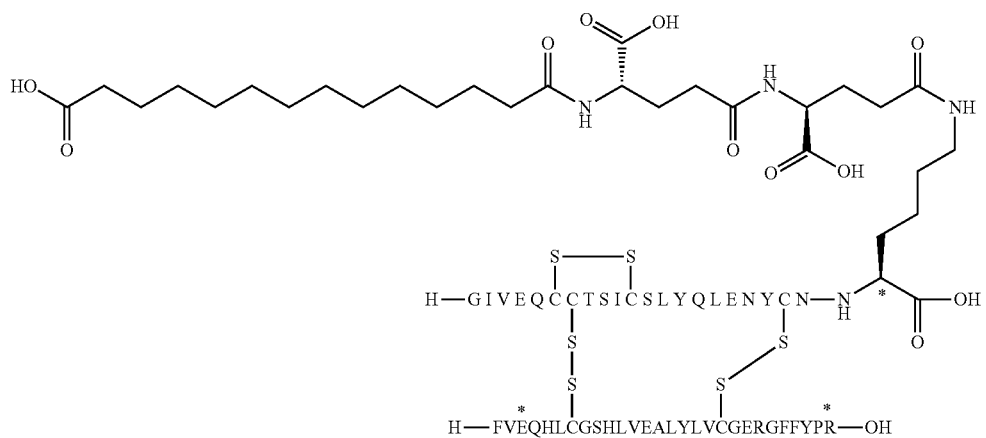

(SEQ ID NO: 1 and SEQ ID NO: 4)

LC-MS (electrospray): m/z=1537.7 (M+4)/4. Calc: 1537.5

Example 25; General Procedure (A)

A22K(N(Eps)-Tetradecanedioyl-gGlu), B3E, desB27, B29R, desB30 Human Insulin

IUPAC (OpenEye, IUPAC style) name: N{Alpha}([GluB3, ArgB29],des-ThrB27,ThrB30-Insulin(human)-(A)-peptidyl)-N{Epsilon}[(4S)-4-carboxy-4-(13-carboxytridecanoylamino)-butanoyl]Lys,(B)-peptide.

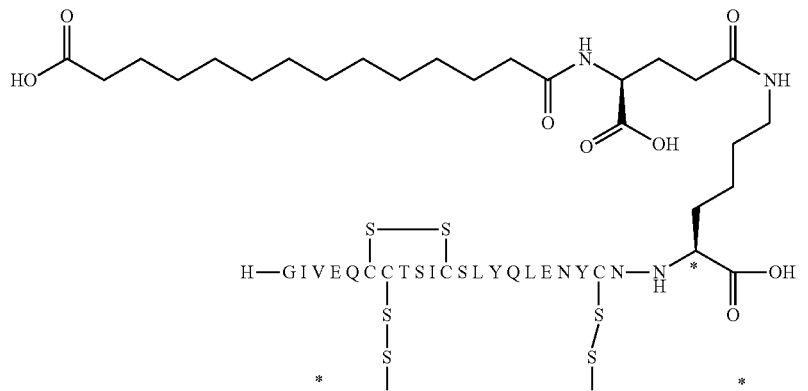

(SEQ ID NO: 1 and SEQ ID NO: 4)

LC-MS (electrospray): m/z=1537.7 (M+4)/4. Calc: 1537.5

Example 26; General Procedure (A)

A22K(N(Eps)-Tetradecanedioyl-3xgGlu), B3E, desB27, B29R, desB30 Human Insulin

IUPAC (OpenEye, IUPAC style) name: N{Alpha}([GluB3, ArgB29],des-ThrB27,ThrB30-Insulin(human)-(A)-peptidyl)-N{Epsilon}[(4S)-4-carboxy-4-[[(4S)-4-carboxy-4-[[(4S)-4-carboxy-4-(13-carboxytridecanoylamino)butanoyl]amino]butanoyl]amino]butanoyl]Lys,(B)-peptide.

Example 27; Insulin Receptor Affinity of Selected Insulin Derivatives of the Invention, Measured on Solubilised Receptors The relative binding affinity of the insulin analogues of the invention for the human insulin receptor (IR) is determined by competition binding in a scintillation proximity assay (SPA) (according to Glendorf T et al. (2008) *Biochemistry* 47 4743-4751).

In brief, dilution series of a human insulin standard and the insulin analogue to be tested are performed in 96-well Optiplates (Perkin-Elmer Life Sciences) followed by the addition of [$^{125}$I-A14Y]-human insulin, anti-IR mouse antibody 83-7, solubilised human IR-A (semipurified by wheat germ agglutinin chromatography from baby hamster kidney (BHK) cells overexpressing the IR-A holoreceptor), and

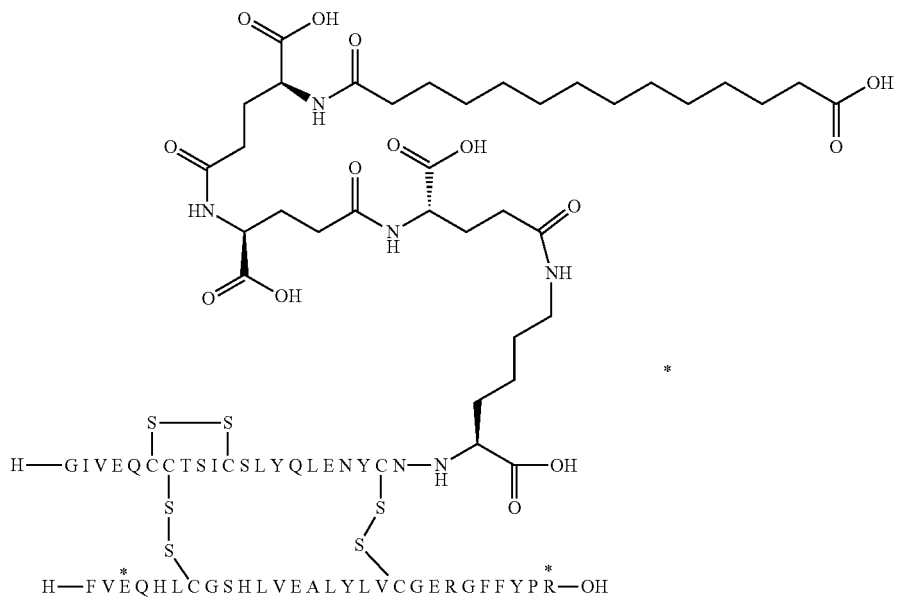

(SEQ ID NO: 1 and SEQ ID NO: 4)

This analogue may be prepared according to the method described in Example 1.

SPA beads (Anti-Mouse polyvinyltoluene SPA Beads, GE Healthcare) in binding buffer consisting of 100 mM HEPES (pH 7.8), 100 mM NaCl, 10 mM $MgSO_4$, and 0.025% (v/v) Tween 20. Plates are incubated with gentle shaking for 22-24 h at 22° C., centrifuged at 2000 rpm for 2 minutes and counted on a TopCount NXT (Perkin-Elmer Life Sciences).

Data from the SPA are analysed according to the four-parameter logistic model (Vølund A (1978) *Biometrics* 34 357-365), and the binding affinities of the analogues calculated relative to that of the human insulin standard measured within the same plate.

A related assay is also used wherein the binding buffer contains 1.5% HSA (w/v) (Sigma A1887) in order to mimic more physiological conditions.

Insulin receptor affinities and other in vitro data of selected insulin analogues of the invention are presented in Table 1, below.

Example 28; Insulin and Insulin-Like Growth Factor-1 Receptor Affinities of Selected Insulin Derivatives of the Invention, Measured on Membrane Associated Receptors Membrane-associated human IR and IGF-1R are purified from BHK cells stably transfected with the pZem219B vector containing either the human IR-A, IR-B or IGF-IR insert. BHK cells are harvested and homogenized in ice-cold buffer (25 mM HEPES pH 7.4, 25 mM $CaCl_2$ and 1 mM $MgCl_2$, 250 mg/L bacitracin, 0.1 mM Pefablock). The homogenates are layered on a 41% (w/v) sucrose cushion and centrifuged for 75 minutes at 95000 g at 4° C. The plasma membranes are collected, diluted 1:5 with buffer (as above) and centrifuged again for 45 minutes at 40000 g at 4° C. The pellets are re-suspended in a minimal volume of buffer and drawn through a needle (size 23) three times before storage at −80° C. until usage.

The relative binding affinity for either of the membrane-associated human IR-A, IR-B or IGF-1R is determined by competition binding in a SPA setup. IR assays are performed in duplicate in 96-well OptiPlates (Perkin-Elmer Life Sciences). Membrane protein is incubated with gentle agitation for 150 minutes at 25° C. with 50 pM [$^{125}$I-A14Y]-human insulin in a total volume of 200 μL assay buffer (50 mM HEPES, 150 mM NaCl, 5 mM $MgSO_4$, 0.01% Triton X-100, 0.1% (w/v) HSA (Sigma A1887), Complete EDTA-free protease inhibitors), 50 μg of wheat germ agglutinate (WGA)-coated PVT microspheres (GE Healthcare) and increasing concentrations of ligand. Assays are terminated by centrifugation of the plate at 2000 rpm for 2 minutes and bound radioactivity quantified by counting on a TopCount NXT (Perkin-Elmer Life Sciences).

IGF-1R assays are conducted essentially as for the IR binding assays except that membrane-associated IGF-1R and 50 pM [$^{125}$I-Tyr31]-human IGF-1 were employed. Data from the SPA are analysed according to the four-parameter logistic model (Vølund A (1978) *Biometrics* 34 357-365), and the binding affinities of the analogues to be tested are calculated relative to that of the human insulin standard measured within the same plate.

IR (A isoform) and IGF-1R binding data of selected insulin analogues of the invention are given in Table 1, below.

TABLE 1

IR (A isoform) and IGF-1 receptor binding data of selected insulin analogues of the invention

| Ex. No. | Relative IR-A affinity* (@ 0% HSA) (%) | Relative IR-A affinity* (@ 1.5% HSA) (%) | Relative IR-A affinity** (@ 0.1% HSA) (%) | Relative IGF-1R affinity*** (@ 0.1% HSA) (%) | IR IGF1 ratio**** |
|---|---|---|---|---|---|
| 1 | 218.4 | 106.2 | 150.4 | 233.8 | 0.64 |
| 2 | 144.0 | 69.2 | 131.4 | 137.0 | 0.96 |
| 3 | 150.2 | 95.6 | 111.0 | 127.8 | 0.87 |
| 4 | 176.8 | 10.9 | 37.8 | 66.4 | 0.57 |
| 5 | 178.5 | 17.0 | 39.0 | 184.2 | 0.21 |
| 6 | 128.0 | 17.7 | 54.6 | 126.5 | 0.43 |
| 7 | 193.8 | 111.6 | 126.3 | 194.7 | 0.65 |
| 8 | 169.2 | 27.6 | 33.6 | 197.4 | 0.17 |
| 9 | 209.0 | 29.9 | 19.3 | 130.9 | 0.15 |
| 10 | 166.8 | 91.4 | 237.6 | 241.3 | 0.98 |
| 11 | 277.4 | 15.8 | 39.3 | 108.8 | 0.36 |
| 12 | 167.6 | 35.5 | 46.4 | 309.7 | 0.15 |
| 13 | 291.3 | 29.2 | 79.9 | 208.9 | 0.38 |
| 14 | 211.9 | 76.7 | 173.9 | 325.9 | 0.59 |
| 15 | 203.0 | 89.4 | 98.4 | 228.5 | 0.43 |
| 16 | 223.5 | 92.5 | 107.3 | 415.7 | 0.26 |
| 17 | 241.7 | 117.9 | 117.3 | 546.4 | 0.21 |
| 18 | 166.2 | 17.8 | 36.8 | 89.8 | 0.41 |
| 19 | 166.9 | 52.8 | 75.8 | 118.0 | 0.64 |
| 20 | 184.4 | 127.8 | 130.5 | 260.1 | 0.50 |
| 21 | 99.0 | 132.6 | 74.9 | 151.7 | 0.49 |
| 22 | 64.9 | 54.5 | 43.6 | 143.3 | 0.30 |
| 23 | 84.4 | 44.3 | 38.9 | 90.9 | 0.43 |
| 24 | 183.5 | 76.6 | 84.3 | 184.3 | 0.46 |
| 25 | 188.7 | 68.8 | 65.2 | 225.7 | 0.29 |

*Solubilised cloned human insulin receptor A isoform, data expressed in % relative to human insulin, protocol given in Example 27.
**Membrane-associated cloned human insulin receptor A isoform receptor, data expressed in % relative to human insulin, protocol given in Example 28.
***Membrane-associated cloned human insulin-like growth factor-1 receptor, data expressed in % relative to human insulin, protocol given in Example 28.
****Ratio of IR-A to IGF-1R affinities from membrane-associated receptors, protocols from Example 28.

Example 29; Monomer-Dimer Equilibrium Analysed by SEC-HPLC Dilution

A series of dilutions with SEC-HPLC (size exclusion HPLC) were performed to assess the monomer-dimer equilibrium of zinc free insulin. By injecting a varying volume (2.5-80 μL) of 0.6 mM of the insulin analogue to be tested on a Superose 12 10/300 GL column, and eluting with 140 mM NaCl, 10 mM Tris pH 7.7 with a flow rate of 0.8 mL/min, the sample is diluted practically proportional to the injection volume. Based on the shift in retention time as a function of dilution, two parameters were calculated; increase in molecular weight (Mw-increase) and R-slope.

R-slope was derived as the slope of a retention time vs. log(injection volume) plot whereas Mw-increase was calculated via a set of reference samples as the apparent molecular weight increase between the lowest and highest injection volume. Both parameters reflect the tendency of the insulin analogue to dissociate in response to dilution and hence, the potential for obtaining fast dissociation to monomers upon sc injection.

The results of these determinations and those of the insulin analogues of the prior art are presented in Tables 2-4, below.

TABLE 2

Increase in molecular weight (Mw-increase)
Compounds of the invention

| Compound of Example. | R-slope (min/µL) | Mw-increase (%) |
|---|---|---|
| 1 | −0.05 | 3.18 |
| 2 | −0.06 | 4.29 |
| 3 | −0.06 | 5.18 |
| 4 | −0.02 | 1.69 |
| 7 | −0.03 | 2.55 |
| 10 | −0.08 | 6.01 |
| 11 | −0.13 | 10.71 |

TABLE 3

Increase in molecular weight (Mw-increase)
Compounds of the prior art (WO 2009/022013‡)

| Prior art Ex.‡ | R-slope (min/µL) | MW-increase (%) |
|---|---|---|
| Insulin aspart | −0.04 | 3.00 |
| Human insulin | −0.65 | 56.0 |
| 1 | −0.78 | 83.2 |
| 4 | −0.66 | 68.2 |
| 5 | −0.52 | 53.3 |
| 42 | −0.74 | 75.8 |
| 44 | −0.75 | 75.5 |
| 45 | −0.73 | 71.6 |

The given example numbers are A22K acylated analogues without deletion of the B27Thr residue (desB27) known and described in the prior art (e.g. WO 2009/022013).

TABLE 4

Increase in molecular weight (Mw-increase)
Compounds of the prior art (WO 2007/096431‡)

| Prior art Ex No‡ | R-slope (min/µL) | MW-increase (%) |
|---|---|---|
| 11 | * | * |
| 12 | −0.66 | 74.4 |

*) No data could be obtained due to poor solubility of the insulin analogue at pH 7.4

The given example numbers are A22K acylated analogues without deletion of the B27Thr residue (desB27) known and described in the prior art (e.g. WO 2007/096431).

Conclusion

It can be concluded that the A22K acylated insulins of the invention, being desB27 analogues, are much more prone to dissociate in response to dilution, and are thus much more usable for prandial bolus administration than similar A22K acylated analogues (without deletion of the B27Thr residue) of the prior art. It can further be concluded that the insulins of the invention in this assay resemble insulin aspart (commercially available as NovoRapid® or NovoLog®(Novo Nordisk A/S), used as a prandial insulin) more than human insulin (also used as a prandial insulin, but with a slower action profile than that of insulin aspart) underlining the improved properties of the derivatives of the invention relative to those of the prior art.

The analogues of the invention all have a less negative R-slope −0.13 to −0.02 (Table 2) thus resembling insulin aspart (R-slope −0.04; see Table 3) much more than human insulin (R-slope −0.65; see Table 3). Contrary, all the tested similar analogues of the prior art have a R-slope resembling that of human insulin (−0.52 to −0.78; Tables 3 and 4).

Consequently, all the analogues of the invention showed less Mw-increase than those of the prior art (up to 10.7% versus 53-83%, respectively (see Tables 2, 3 and 4).

These data indicate that the compounds of the invention are more monomeric than the similar analogues of the prior art. In this respect the compounds of the invention resemble insulin aspart, whereas the similar analogues of the prior art resemble human insulin.

Example 30; Self-Association Measured by Small Angle X-Ray Scattering (SAXS)

SAXS data was used to estimate the self-association state of the insulin analogues to be tested after subcutaneous injection. SAXS data were collected from Zn-free formulations containing 0.6 mM of insulin analogue to be tested and 140 mM NaCl at pH 7.4. For each analogue, the relative amounts of monomer, dimer and larger species was estimated using the fact that a SAXS scattering profile has an intensity contribution from all individual components in a multicomponent mixture. By using intensities (form factors) from each component it is possible to estimate the volume fraction contribution of each component in the mixture. A system of linear equations using the algorithm of nonnegative or unconstrained least-squares is used to minimize the discrepancy between the experimental and calculated scattering curves. Form factors are calculated from crystal structures of a monomer, dimer, hexamer etc. The volume fractions are expressed in percentages (%).

The average molecular weight is approximated by using a reference sample with known concentration and assuming that the ratio of the molecular masses is identical to the ratio of the scattered intensity at zero angle, I(0), normalized against the measured concentrations.

Results obtained from derivatives of the invention and of derivatives of the prior art are shown in Tables 5, 6, and 7, below.

TABLE 5

SAXS data of derivatives of the invention

| Ex. No. | Radius of gyration, Rg (nm) | Dmax** (nm) | Monomer (%) | Dimer (%) | Larger species (%) |
|---|---|---|---|---|---|
| 1 | 1.8 | 6.5 | 80 | 0 | 20 |
| 2 | 1.4 | 4.3 | 74 | 24 | 2 |
| 4 | 1.3 | 4.0 | 69 | 30 | 1 |
| 10 | 1.8 | 6.6 | 78 | 0 | 22 |
| 11 | 1.6 | 5.7 | 63 | 26 | 11 |
| 7 | 1.6 | 5.8 | 66 | 27 | 7 |
| 18 | 1.6 | 5.5 | 56 | 39 | 5 |

TABLE 6

SAXS data of derivatives of the prior art (WO 2009/022013‡)

| Ex. No.‡ | Radius of gyration, Rg (nm) | Dmax (nm) | Monomer (%) | Dimer (%) | Larger species (%) |
|---|---|---|---|---|---|
| 5 | 2.9 | 10 | 48 | 0 | 52 |
| 4 | 3.2 | 11.4 | 0 | 58 | 42 |
| 44 | 2.3 | 8.0 | 0 | 57 | 43 |
| 6 | 2.4 | 7.9 | 30 | 22 | 48 |
| 42 | 2.6 | 8.9 | 0 | 47 | 53 |
| 1 | 2.8 | 10.0 | 0 | 46 | 54 |
| 45 | 2.4 | 8.2 | 27 | 17 | 56 |

TABLE 7

SAXS data of derivatives of the prior art (WO 2007/096431‡)

| Ex. No.‡ | Radius of gyration, Rg (nm) | Dmax (nm) | Monomer (%) | Dimer (%) | Larger species (%) |
|---|---|---|---|---|---|
| 12 | 3.1 | 12.0 | 48 | 0 | 52 |
| 11* | * | * | * | * | * |

*) Derivative precipitated in assay buffer indicating presence of very large species or aggregates. No data could be obtained.

It can be concluded from these studies that the derivatives of the invention, at conditions mimicking conditions in the subcutaneous tissue after injection, are much more prone to dissociate into monomers and will thus be absorbed much more quickly after subcutaneous injection than analogues of the prior art. The monomeric content ranges from 63-83% for the analogues of the invention, versus 0-48% for the analogues of prior art. It can further be concluded that for the analogues of the prior art, the largest molecular species observed are both larger in size (Rg and Dmax) as well as found in larger amounts (42-62% vs 1-22% for the analogues of the invention). This underlines the utility of the analogues for prandial use compared to analogues of the prior art.

Example 31; Preparation of Pharmaceutical Preparations

The pharmaceutical preparations of the present invention may be formulated as an aqueous solution. The aqueous solution is made isotonic, for example, with sodium chloride and/or glycerol. Furthermore, the aqueous medium may contain buffers and preservatives. The pH value of the preparation is adjusted to the desired value and may be between about 3 to about 8.5, between about 3 and about 5, or about 6.5, or about 7.4, or about 7.5, depending on the isoelectric point, pI, of the insulin analogue in question.

Preparation of Zinc-Free Insulin Formulations

Zinc-free insulin analogues were dissolved in aqueous solution, which in the final formulation contained 0.6 mM insulin analogue, 16 mM m-cresol, 16 mM phenol, 7 mM disodium phosphate, appropriate amounts of nicotinamide and glycerol, and the pH was adjusted to 7.3-7.5 (measured at room temperature) using 1 N hydrochloric acid/1 N NaOH. Water was added to the final volume and the solution was sterile-filtered through a 0.2 μm filter. The formulation was filled into 2 ml vials and sealed using crimp caps.

Example 32; ThT Fibrillation Assay for the Assessment of Physical Stability of Protein Formulations Low physical stability of a peptide may lead to amyloid fibril formation, which is observed as well-ordered, thread-like macromolecular structures in the sample eventually resulting in gel formation. Thioflavin T (ThT) has a distinct fluorescence signature when binding to fibrils [Naiki et al. (1989) *Anal. Biochem.* 177 244-249; LeVine (1999) *Methods. Enzymol.* 309 274-284].

Formation of a partially folded intermediate of the peptide is suggested as a general initiating mechanism for fibrillation. Few of those intermediates nucleate to form a template onto which further intermediates may assemble and the fibrillation proceeds. The lag-time corresponds to the interval in which the critical mass of nucleus is built up and the apparent rate constant is the rate with which the fibril itself is formed (FIG. 1).

Sample Preparation

Samples were prepared freshly before each assay. Samples of each composition was mixed with an aqueous ThT-solution (0.1 mM ThT) in a volumetric ratio of 990:10 and transferred to a 96 well microtiter plate (Packard Opti-Plate™-96, white polystyrene). Usually, four or eight replica of each sample (corresponding to one test condition) were placed in one column of wells. The plate was sealed with Scotch 15 Pad (Qiagen).

Incubation and Fluorescence Measurement

Incubation at given temperature, shaking and measurement of the ThT fluorescence emission were done in a Fluoroskan Ascent FL fluorescence platereader or Varioskan plate reader (Thermo Labsystems). The temperature was adjusted to 37° C. The orbital shaking was adjusted to 960 rpm with an amplitude of 1 mm in all the presented data. Fluorescence measurement was done using excitation through a 444 nm filter and measurement of emission through a 485 nm filter. Each run was initiated by incubating the plate at the assay temperature for 10 minutes. The plate was measured every 20 minutes for up to 45 hours. Between each measurement, the plate was shaken and heated as described.

TABLE 8

Exemplary compositions of insulin preparations

| Ex. No | Insulin derivative (mM) | Phenol (mM) | m-cresol (mM) | Nicotinamide (mM) | Glycerol (% w/v) | Phosphate (mM) | pH |
|---|---|---|---|---|---|---|---|
| A | 2 | 0.6 | 16 | 16 | — | 1.8 | 7 | 7.4 |
| B | 2 | 0.6 | 16 | 16 | 80 | 1.3 | 7 | 7.4 |
| C | 2 | 0.6 | 16 | 16 | 170 | 0.7 | 7 | 7.4 |
| D | 7 | 0.6 | 16 | 16 | — | 1.8 | 7 | 7.4 |
| E | 7 | 0.6 | 16 | 16 | 80 | 1.3 | 7 | 7.4 |
| F | 7 | 0.6 | 16 | 16 | 170 | 0.7 | 7 | 7.4 |
| G | 4 | 0.6 | 16 | 16 | — | 1.8 | 7 | 7.4 |
| H | 4 | 0.6 | 16 | 16 | 80 | 1.3 | 7 | 7.4 |
| I | 4 | 0.6 | 16 | 16 | 170 | 0.7 | 7 | 7.4 |
| J | 180 | 0.6 | 16 | 16 | 170 | 0.7 | 7 | 7.4 |

Data Handling

Figure 14A:
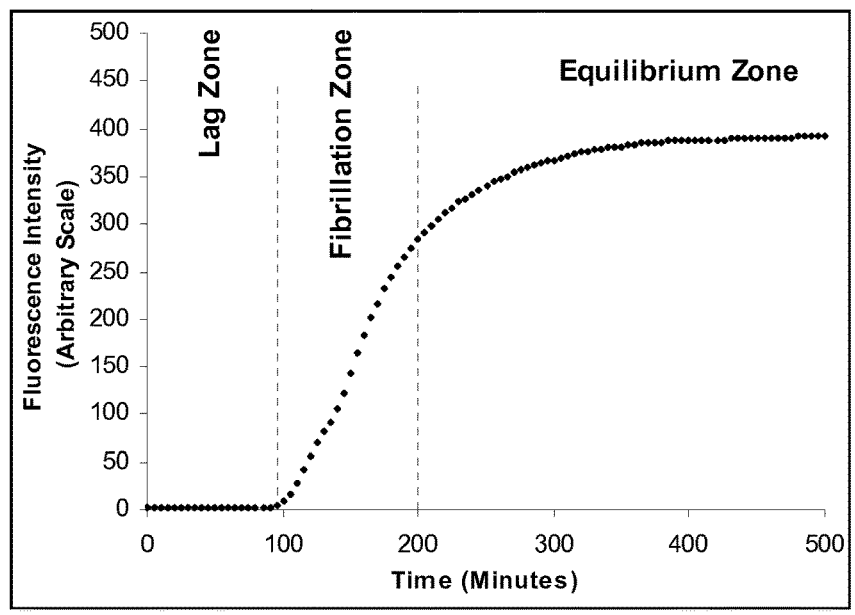
FIGS. 14A, 14B and 14C show fluorescence vs. time plots, from which the lag time can be estimated as the intercept between linear approximation of the Lag Zone and Fibrillation Zone.
Figure 14B:
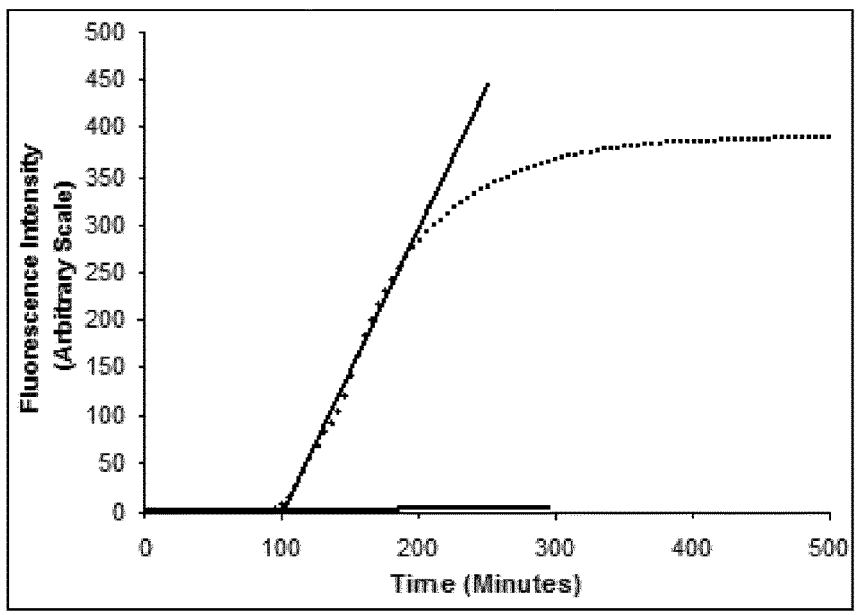
Figure 14C:
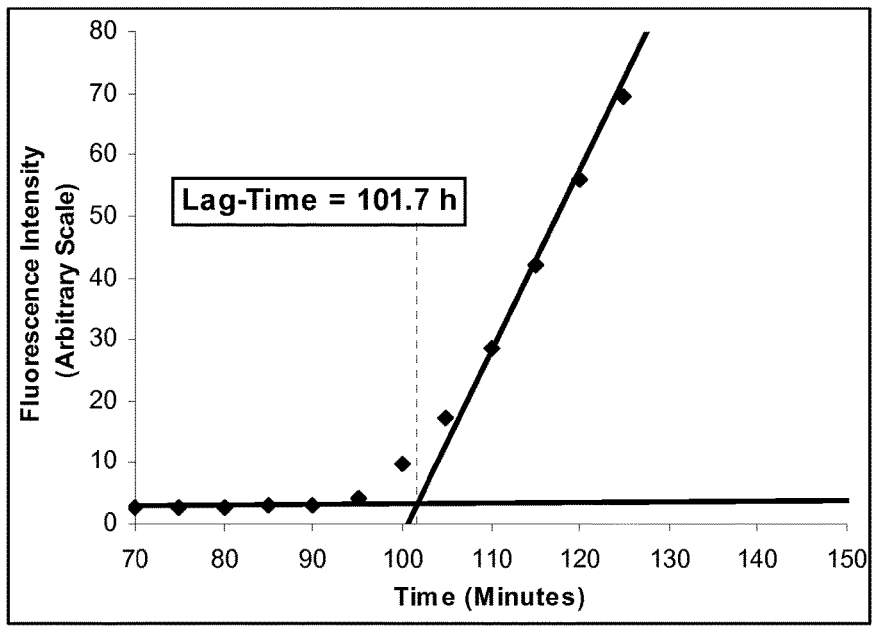

Fluorescence vs. time plots were generated in Microsoft Excel and the lag time was estimated as the intercept between linear approximation of the Lag Zone and Fibrillation Zone as illustrated in FIGS. 14A, 14B and 14C (illustration 1A, 1B and 1C, respectively). An increase in lag-time corresponds to an increased physical stability. The data points are typically a mean of four or eight samples.

no. 186005225) with an eluent containing 55% (v/v) acetonitrile, 0.05% TFA at a flow rate of 0.2 ml/min and a column temperature of 40° C. Detection was performed with a tunable absorbance detector (Waters Acquity TUV) at 215 nm. Injection volume was 1.5 μl of both the 600 μM insulin analogue formulations and a 600 μM human insulin standard. Each analogue preparation was incubated at 5, 25 and 37° C. in 2 ml vials. At defined times HMWP and content of the preparations were measured. The results are shown in Table 9, below.

TABLE 9

HMWP content by storage at 37° C.

| Weeks at 37° C. | Example No 2 | | | Example No 4 | | | Example No 7 | | | Ex. No 18 | WO 2009/022013 Ex. No 5 |
|---|---|---|---|---|---|---|---|---|---|---|---|
| | A | B | C | D | E | F | G | H | I | J | — |
| 0 | 0.5% | 0.1% | 0.1% | 0.5% | 0.2% | 0.2% | 1.9% | 0.1% | 0.1% | 0.5% | 3.3% |
| 2 | 0.6% | 0.2% | 0.2% | 0.7% | 0.4% | 0.4% | 2.5% | 0.5% | 0.5% | 1.1% | 4.9% |
| 4 | 0.8% | 0.3% | 0.3% | 1.0% | 0.5% | 0.5% | 4.1% | 0.7% | 0.7% | * | 13.1% |
| 8 | 2.3% | * | * | 2.2% | * | * | 6.8% | * | * | * | 29.1% |

* Not determined

Results obtained for the A22K acylated analogues if the invention, and of similar A22K acylated analogues of the prior art without deletion of the B27Thr residue (desB27), are shown in Table 8, below.

TABLE 8

Physical stability measured as ThT lag time of zinc-free preparations

| Example No | Formulation | Lag time (h) in ThT assay | RSD (%) |
|---|---|---|---|
| 2 | A | 26.7 | 27 |
| 2 | B | 34.9 | 16 |
| 2 | C | 42 | 6 |
| 4 | D | 43.5 | 5 |
| 4 | E | 45 | * |
| 4 | F | 45 | * |
| 7 | G | 26.3 | 20 |
| 7 | H | 20.2 | 31 |
| 7 | I | 15 | 15 |
| 18 | J | 14 | 17 |
| WO 2009/022013 Ex 5 | — | 15.0 | 17 |
| WO 2007/096431 Ex 12 | — | 4.7 | 17 |

* No fibrillation within timespan of ThT assay

It is concluded that the A22K acylated insulin analogues of the invention display better or similar stability towards fibrillation (i.e. have increased physical stability) in zinc-free formulation both with and without nicotinamide added than similar analogues of the prior art. This is very surprising since SAXS and SEC-HPLC dilution data indicate that the insulin analogues of the invention are smaller in size (i.e. composed of monomers and dimers) which the skilled person would expect would lead to less physical stability.

Example 33; Analysis of Insulin Chemical Stability

Size Exclusion Chromatography
Formulations Used: See Example 31
Quantitative determination of high molecular weight protein (HMWP) and monomer insulin analogue was performed on Waters Acquity BEH200 SEC column (150×2.4 mm, part It is concluded that formation of high molecular weight proteins (HMWP) by storage in zinc-free formulation at 37° C. is far less for insulin derivatives of the invention (formation of up to 6.8% HMWP after 8 weeks storage for the insulins of the invention of Examples 2, 4 and 7, respectively), whereas a similar insulin derivative of the prior art results in formation of 29.1% HMWP). It is further concluded that the insulin derivatives of the invention form low levels of HMWP in zinc-free formulation and in presence of nicotinamide when stored at 37° C.

Reverse Phase Chromatography (UPLC)

Determination of the insulin related impurities were performed on a UPLC system using a Phenomenex Kinetex C18 column, size of 2.1×150 mm, particle size of 1.7 μm, and pore size of 100 Å (Phenomenex part no. 00F-4475-AN), with a flow rate of 0.3 ml/min at 50° C. and with UV detection at 215 nm. Elution was performed with a mobile phase consisting of the following: A: 10% (v/v) acetonitrile, 0.09M di-ammonium hydrogen phosphate, pH 3.6, and B: 80% (v/v) acetonitrile. Gradient: 0-7 min linear change from 15% B to 26% B, 7-34 min linear change to 40% B, 34-36 minutes linear change to 80% B for column wash, before returning to initial conditions at 39 min 15% B. The amount of impurities was determined as absorbance area measured in percent of total absorbance area determined after elution of the preservatives. Each analogue preparation was incubated at 5, 25 and 37° C. in 2 ml vials. At defined times the insulin related impurities of the preparations was measured. The results are shown in Table 10, below.

TABLE 10

Purity by storage at 37° C.

| Weeks at 37° C. | Example No 2 | | | Example No 4 | | | Example No 7 | | | Ex. No 18 | WO 2009/022013 Ex. No 5 |
|---|---|---|---|---|---|---|---|---|---|---|---|
| Formulation | A | B | C | D | E | F | G | H | I | J | — |
| 0 | 95.2% | 98.1% | 97.8% | 92.0% | 95.7% | 95.4% | 84.1% | 98.13% | 98.0% | 92.9% | 88.4% |
| 2 | 93.8% | 96.8% | 96.6% | 90.5% | 94.8% | 95.1% | 79.7% | 95.6% | 95.5% | 90.0% | 36.3% |
| 4 | 93.2% | 94.4% | 94.3% | 89.3% | 92.3% | 92.1% | 76.4% | 93.2% | 92.7% | * | 16.1% |
| 8 | 87.5% | * | * | 86.5% | * | * | 69.1% | * | * | * | 4.1% |

* Not determined

It is concluded that the insulin derivatives of the invention are far more stable in formulation without zinc than a similar A22K acylated analogue of the prior art. The analogues of the prior art are so unstable that less than 5% (corresponding to a loss of purity of 84% points) of the derivative is intact after 8 weeks of storage at 37° C. The insulin analogues of the invention (represented by the compounds of Examples 2, 4 and 7) have less than 7.7, 5.5 and 15% points purity loss, respectively, after 8 weeks of storage at 37° C. It is further concluded that the insulin derivatives of the invention are stable in zinc-free formulation with nicotinamide added.

Example 34; Subcutaneous PK/PD Profiles in LYD Pigs

The insulin derivatives of the invention may be tested by subcutaneous administration to pigs, e.g. comparing with insulin aspart (NovoRapid) in the commercial formulation or comparing with similar A22K acylated insulin analogues of the prior art according to this protocol. The derivatives may be tested for pharmacokinetic and/or pharmacodynamic parameters.
General Methods Used
Ultrasound Examination and Marking of Injection Area During anaesthesia for placement of permanent intravenous catheters, the pigs are examined by ultrasound with and Esaote ultrasound scanner model "MyLabFive" and a linear probe type "LA435 6-18 MHz". Mid neck between ear and scapula, on the right or left side (opposite the catheter), an area of 2×2 cm with no underlying muscle (suitable for subcutaneous injection) is identified and marked by tattoo.
Feeding Schedule The pigs are fasted (no breakfast) prior to the experiment.
The pigs are in their normal pens during the entire experiment and they are not anaesthetized. The pigs are fasted until the 12-hour blood sample has been collected, but with free access to water. After the 12-hour blood sample the pigs are fed food and apples.
Dosing The Penfill is mounted in a NovoPen®4. A new needle is used for each pig. A needle stopper is used to secure max sc penetration to 5 mm below the epidermis. Dose volume (IU volume) is calculated and noted for each pig.

Dose volume (U)=((Weight×dose nmol/kg)/conc nmol/mL)×100 U/mL

The pig is dosed in the subcutis laterally on the right or left side (opposite the catheter) of the neck and the needle is kept in the subcutis for a minimum of 10 seconds after injection to secure deposition of compound.
Treatment of Hypoglycaemia After subcutaneous dosing, glucose solution should be ready for i.v. injection to prevent hypoglycaemia, i.e. 4-5 syringes (20 mL) are filled with sterile 20% glucose, ready for use. Diagnosis of hypoglycemia is based on clinical symptoms and blood glucose measurements on a glucometer (Glucocard X-meter).

Treatment consists of slow i.v. injection of 50-100 ml 20% glucose (10-20 g glucose). The glucose is given in fractions over 5-10 minutes until effect.
Blood Sampling The patency of the jugular catheters is checked prior to the experiment with sterile 0.9% NaCl without addition of 10 IU/mL heparin.

Before and after the dosing, blood samples will be taken in the stable from a central venous catheter at the following time points:

Predose (−10, 0), 3, 6, 9, 12, 15, 20, 30, 45, 60, 90, 120, 150, 180, 240, 300, 360, 420, 480, 540, 600 and 720 minutes Samples are taken with a 3-way stop-cock. 4-5 ml of waste blood is withdrawn and discarded before taking the sample.

Blood samples of 0.8 ml are collected into tubes coated with EDTA for glucose and insulin analysis.

After each blood sample the catheter is flushed with 5 ml of sterile 0.9% NaCl without addition of 10 IU/mL heparin.

The tube is tilted gently a minimum of 10 times to ensure sufficient mixing of blood and anticoagulant (EDTA) and after one minute it is placed on wet ice. The tubes are spun for 10 min at 3000 rpm and 4° C. within 1 hour after sampling. The samples are stored on wet ice until pipetting.

Aseptic technique is demanded to avoid bacterial growth in the catheter with increased risk of clotting.
Closure of the Catheters after the Experiment If blood sampling has not been performed using an aseptic technique, a single intravenous treatment with 1 ml per 10 kg Pentrexyl® (1 g of ampicillin dissolved in 10 ml 0.9% NaCl) can be administered slowly i.v. via the catheter that has been used for blood sampling. Following this treatment, the catheter is flushed with 10 ml 0.9% NaCl.

Catheters are flushed with 5 ml of sterile 0.9% NaCl added heparin (10 IU/mL). The catheters are closed with a new luer-lock with latex injection membrane and 1.0 ml of TauroLockHep500 is injected through the membrane as a lock for the catheter.
Analysis of Blood Samples Plasma glucose: 10 ul of plasma is pipetted into 500 ul of buffer solution for measurements of glucose concentration in plasma in the BIOSEN autoanalyser.

Plasma insulin: 1×50 µl of plasma are pipetted into 0.65 ml Micronic® tubes (ELISA/LOCI/SPA setup) for analysis, using either ELISA or LC-MS.

Plasma is stored frozen at −20° C.

Example 35; Subcutaneous PK/PD Profile of the Insulin Derivative of Example 1 in LYD Pigs Following the general procedure above, the following PK and PD profiles were obtained for the insulin derivative of Example 1.

Formulations Used

Insulin derivative of Example 1, pH=7.4; 609 µM; 1.6% (w/vol) glycerol; 30 mM phenol (0 Zn/hexamer).

Insulin Aspart, commercial formulation, 600 µM; 1.6% (w/vol) glycerol; 7 mM phosphate; 10 mM sodium chloride; 300 µM zinc acetate; 16 mM phenol; 16 mM m-cresol.

The results of these determinations are presented in the appended FIGS. 1-4 and in Table 11, below.

TABLE 11

Pharmacokinetic parameters (mean ± SD)

| Compound | | $T_{max}^a$ (min) | Cmax/D pM/ (nmol/ kg) | AUC/D pM * min/ (pmol/ kg) | $\%_{extrap}$ | $T_{1/2}^b$ (min) | MRT (min) |
|---|---|---|---|---|---|---|---|
| Example 1 | Mean | 11 | 1212 | 122 | 2 | 116 | 165 |
| 0 Zn/hexamer | SD | | 456 | 25 | | 10 | 20 |
| 1 nmol/kg | | | | | | | |
| (n = 8) | | | | | | | |
| NovoRapid ® | Mean | 11 | 1277 | 67 | 2 | 67 | 93 |
| 0.5 nmol/kg | SD | | 788 | 26 | | 16 | 19 |
| (n = 8) | | | | | | | |
| NovoRapid ® | Mean | 14 | 880 | 64 | 2 | 75 | 110 |
| 1 nmol/kg | SD | | 335 | 20 | | 7 | 11 |
| (n = 8) | | | | | | | |

$^a T_{max}$ given as median
$^b T_{1/2}$ given as harmonic mean ± pseudo SD
$^c$Bioavailability calculated based on iv. data (not shown)

Conclusion

It is concluded that insulin derivative of Example 1 in a formulation without zinc has a very similar PK/PD profile as insulin aspart (NovoRapid®) commercial formulation. Further, the mean retention time of this insulin derivative was 165 minutes. It can be concluded that the insulin derivative of Example 1 is useful as a rapid acting (prandial) insulin.

Example 36; Subcutaneous PK/PD Profile of the Insulin Derivative of Example 2 in LYD Pigs Following the general procedure above, the following PK and PD profiles were obtained for the insulin derivative of Example 2.

Formulations Used

Insulin derivative of Example 2, pH=7.367; 607 µM; 1.6% (w/vol) glycerol; 30 mM phenol (0 Zn/hexamer).

Insulin aspart, commercial formulation, 600 µM; 1.6% (w/vol) glycerol; 7 mM phosphate; 10 mM sodium chloride; 300 µM zinc acetate; 16 mM phenol; 16 mM m-cresol.

Figure 4A:
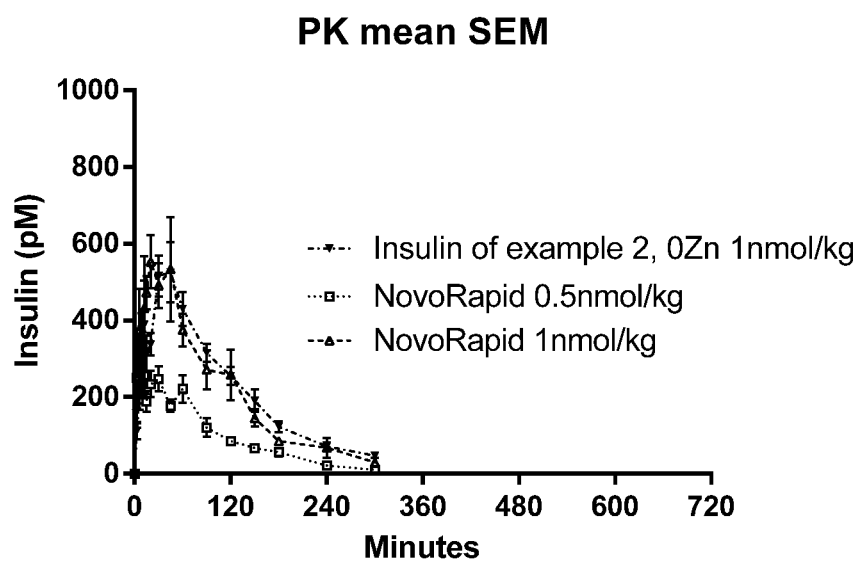
FIGS. 4a and 4b show the PK (pharmacokinetic) profile (insulin concentrations vs. time) of the insulin of Example 2 formulated with 0 zinc per 6 insulin molecules (1 nmol/kg) in comparison with the profile of NovoRapid®/NovoLog® (insulin aspart, commercial formulation, 3 zinc per 6 insulin molecules (0.5 and 1 nmol/kg), and the resulting changes in plasma glucose, respectively.
Figure 4B:
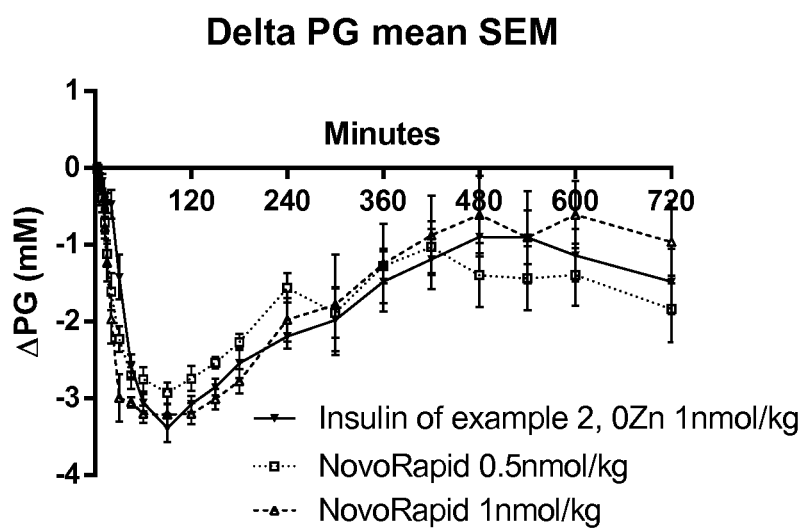
Figure 5A:
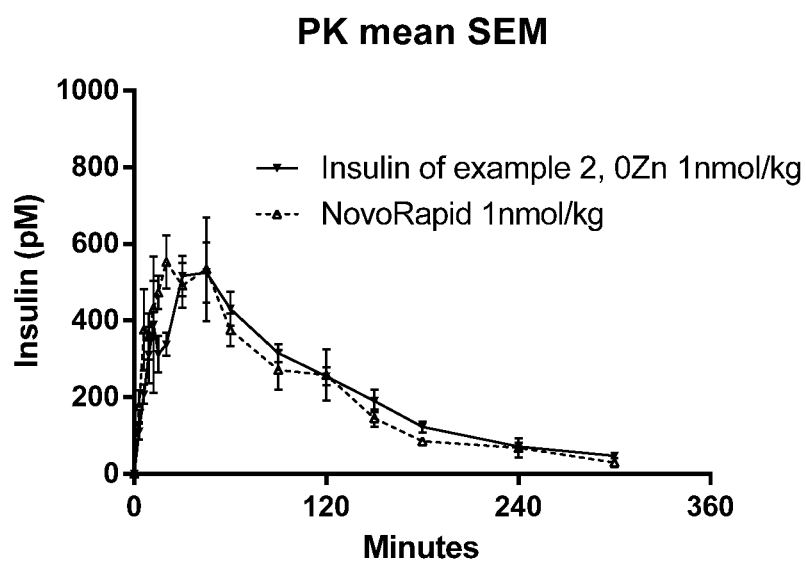
FIGS. 5a and 5b show the same data as in FIGS. 4a and 4b, but shows only the data for the insulin of Example 2 formulated with 0 zinc per 6 insulin molecules (1 nmol/kg) in comparison with the profile of NovoRapid®/NovoLog® (insulin aspart, commercial formulation, 3 zinc per 6 insulin molecules (1 nmol/kg), and the resulting changes in plasma glucose, respectively.
Figure 5B:
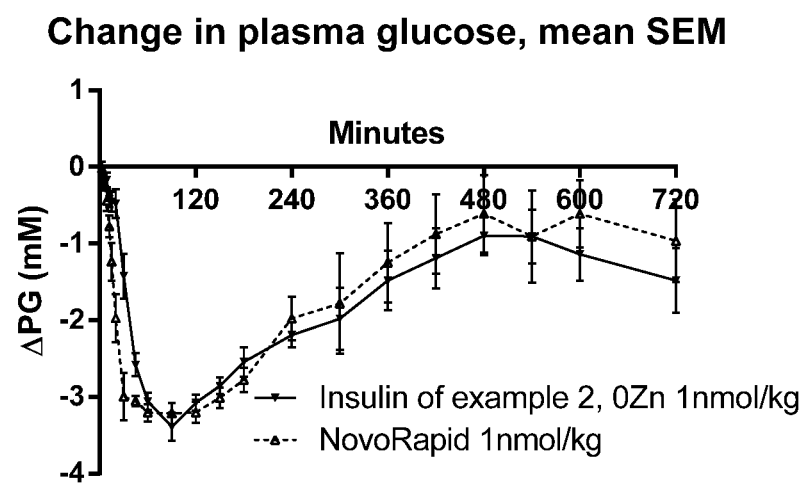

The results of these determinations are presented in the appended FIGS. 4-5 and in Table 12, below.

TABLE 12

Pharmacokinetic parameters (mean ± SD)

| Compound | | $T_{max}^a$ (min) | $C_{max}$/D pM/ (nmol/ kg) | AUC/D pM * min/ (pmol/ kg) | $\%_{extrap}$ | $T_{1/2}^b$ (min) | MRT (min) |
|---|---|---|---|---|---|---|---|
| Example 2 | Mean | 45 | 762 | 68 | 5 | 64 | 111 |
| 0 Zn/hexamer | SD | | 342 | 9 | | 15 | 21 |
| 1 nmol/kg | | | | | | | |
| (n = 7) | | | | | | | |
| NovoRapid | Mean | 30 | 923 | 60 | 2 | 53 | 92 |
| 0.5 nmol/kg | SD | | 510 | 8 | | 15 | 10 |
| (n = 7) | | | | | | | |
| NovoRapid | Mean | 25 | 771 | 64 | 1 | 53 | 98 |
| 1 nmol/kg | SD | | 254 | 16 | | 15 | 28 |
| (n = 6) | | | | | | | |

$^a T_{max}$ given as median
$^b T_{1/2}$ given as harmonic mean ± pseudo SD
$^c$Bioavailability calculated based on i.v. data (not shown)

Conclusion

It is concluded that insulin derivative of Example 2 in a formulation without zinc has a very similar PK/PD profile as insulin aspart. Further, the mean retention time of this insulin derivative was 111 minutes, not significantly different that of NovoRapid® (insulin aspart). It can be concluded that the insulin derivative of Example 2 is useful as a rapid acting (prandial) insulin.

Example 37; Subcutaneous PK/PD Profile of the Insulin Derivative of Example 11 in LYD Pigs Following the general procedure above, the following PK and PD profiles were obtained for the insulin derivative of Example 11.

Formulations Used

Insulin derivative of Example 11, pH=7.44; 689 µM; 1.6% (w/vol) glycerol; 30 mM phenol (0 Zn/hexamer).

The results of these determinations are presented in the appended FIGS. 6-7 and in Table 13, below.

Figure 6:
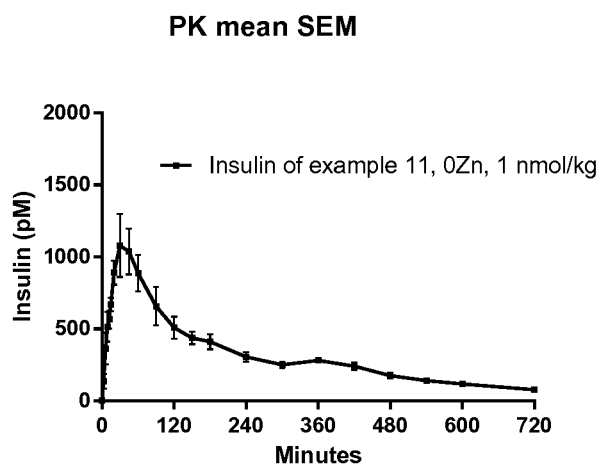
FIGS. 6 and 7 shows the PK (pharmacokinetic) profile (insulin concentrations vs. time) of the insulin of Example 11 formulated with 0 zinc per 6 insulin molecules (1 nmol/kg), and the resulting changes in plasma glucose, respectively.
Figure 7:
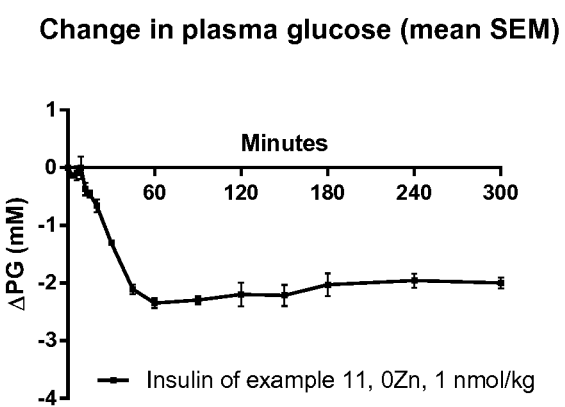

FIGS. 6 and 7 show the PK (pharmacokinetic) profile (insulin concentrations vs. time) of the insulin of Example 11 formulated with 0 zinc per 6 insulin molecules (1 nmol/kg), and the resulting changes in plasma glucose, respectively; 1 nmol/kg

TABLE 13

Pharmacokinetic parameters (mean ± SD)

| Compound | | $T_{max}^a$ (min) | Cmax/D pM/ (nmol/ kg) | AUC/D pM * min/ (pmol/kg) | $\%_{extrap}$ | $T_{1/2}^b$ (min) | MRT (min) |
|---|---|---|---|---|---|---|---|
| Example 11 | Mean | 38 | 1207 | 261 | 12 | 245 | 334 |
| 1 nmol/kg | SD | | 330 | 60 | | 32 | 46 |
| (n = 4) | | | | | | | |

$^a T_{max}$ given as median
$^b T_{1/2}$ given as harmonic mean ± pseudo SD

It is concluded that insulin derivative of Example 11 in a formulation without zinc has a PK profile qualifying as a prandial insulin. Further, the mean retention time of this insulin derivative was 334 minutes, significantly shorter than the profile obtained for the similar (also) 1,16-hexadecanedioic acid containing insulin derivative of the prior art, A22K(N(eps)-hexadecanedioyl-gGlu-2×OEG), B29R, desB30 human insulin (WO 2009/022013, Example 45, (MRT=1287 minutes), see below. It can be concluded that the insulin derivative of Example 11 is useful as a rapid acting (prandial) insulin.

Example 38; Subcutaneous PK/PD Profile of the Insulin Derivative of Example 4 in LYD Pigs Following the general procedure above, the following PK and PD profiles were obtained for the insulin derivative of Example 4.

Formulation Used

Insulin derivative of Example 4, pH=7.43; 621 µM; 1.8% (w/vol) glycerol; 16 mM phenol; 16 mM m-cresol; 10 mM sodium chloride (0 Zn/hexamer).

Figure 8:
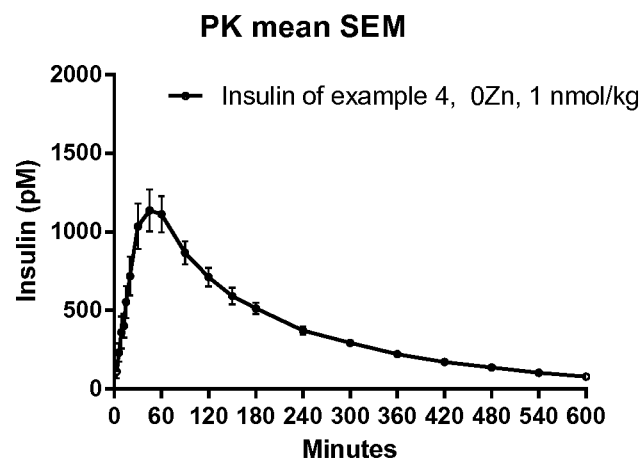
FIGS. 8 and 9 shows the PK (pharmacokinetic) profile (insulin concentrations vs. time) of the insulin of Example 44 formulated with 0 zinc per 6 insulin molecules (1 nmol/kg), and the resulting changes in plasma glucose, respectively (1 nmol/kg)
Figure 9:
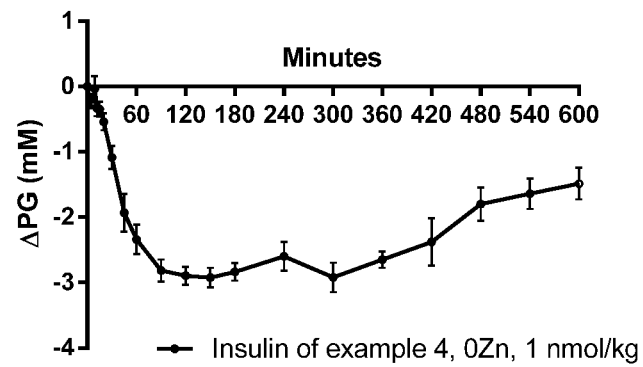

The results of these determinations are presented in the appended FIGS. 8-9 and in Table 14, below.

TABLE 14

Pharmacokinetic data

| Compound | $T_{max}{}^a$ (min) | $C_{max}$/D pM/ (nmol/ kg) | AUC/D pM * min/ (pmol/kg) | %$_{extrap}$ | $T_{1/2}{}^b$ (min) | MRT (min) |
|---|---|---|---|---|---|---|
| Example 4 0 zn/ hexamer 1 nmol/kg | Mean SD | 45 | 1272 394 | 255 41 | 8 | 160 26 | 235 34 |

$^a T_{max}$ given as median
$^b T_{1/2}$ given as harmonic mean ± pseudo SD

It is concluded that insulin derivative of Example 4 in a formulation without zinc has a PK profile qualifying as a prandial insulin. Further, the mean retention time of this insulin derivative was 160 minutes, significantly shorter than the profile obtained for the similar 1,16-hexadecanedioic acid containing insulin derivative of the prior art, A22K(N(eps)hexadecanedioyl-gGlu-2×OEG), B29R, desB30 human insulin (WO 2009/022013, Example 45, (MRT=1287 minutes), see below. It can be concluded that the insulin derivative of Example 4 is useful as a rapid acting (prandial) insulin.

Example 39; Subcutaneous PK/PD Profile of an Insulin Derivative of the Prior Art in LYD Pigs Following the general procedure above, the following PK and PD profiles were obtained for the insulin derivative of the prior art, A22K(N(eps)-hexadecanedioyl-gGlu-2×OEG), B29R, desB30 human insulin (WO 2009/022013, Example 45.

Formulations Used

The compound of WO 2009/022013, Example 45, 588 µM; 1.6% (w/vol) glycerol; 30 mM phenol; 7 mM tris, pH=7.4 (0 Zn/hexamer), 1 nmol/kg.

The results of these determinations are presented in the appended FIGS. 10 and 11, and in Table 15, below.

Figure 10:
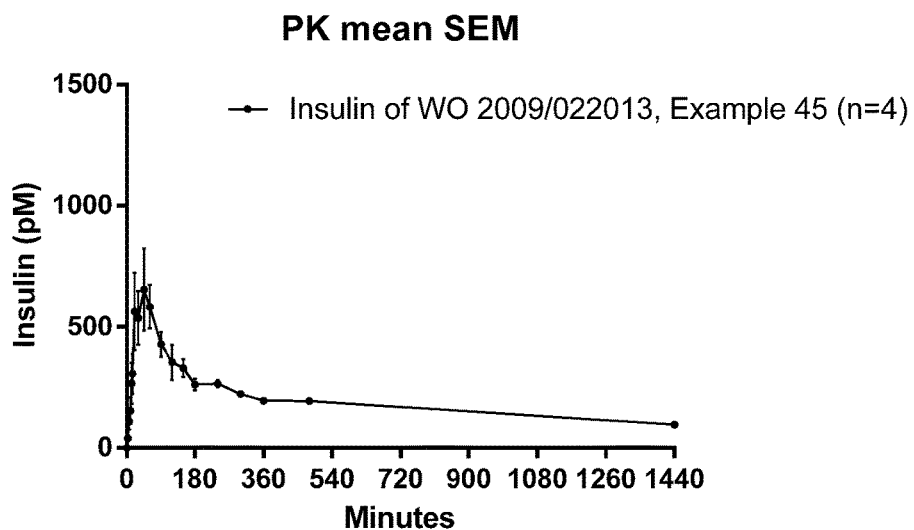
FIGS. 10 and 11 shows the PK (pharmacokinetic) profile (insulin concentrations vs. time) of an insulin of the prior art A22K(N(eps)-hexadecanedioyl-gGlu-2×OEG), B29R, desB30 human insulin (WO 2009/022013, Example 45) formulated with 0 zinc per 6 insulin molecules (1 nmol/kg), and the resulting changes in plasma glucose, respectively (1 nmol/kg)
Figure 11:
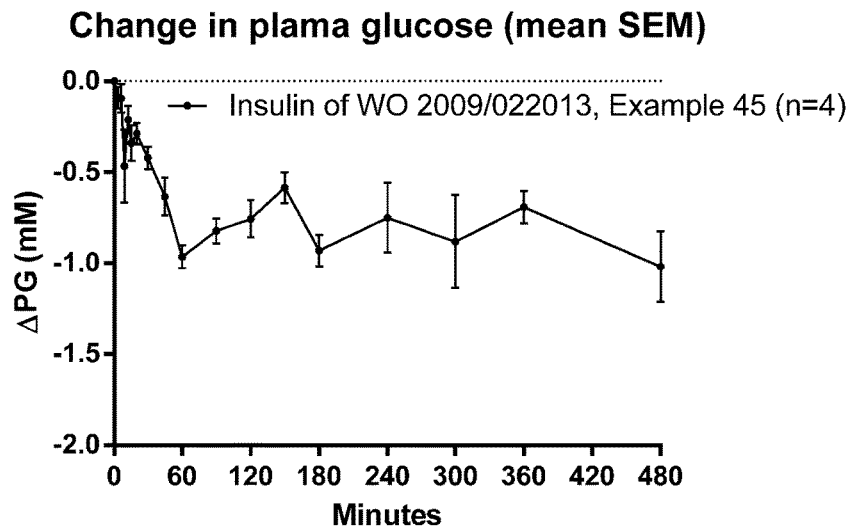

FIGS. 10 and 11 shows the PK (pharmacokinetic) profile (insulin concentrations vs. time) of an insulin derivative of the prior art, i.e. A22K(N(eps)-hexadecanedioyl-gGlu-2×OEG), B29R, desB30 human insulin (WO 2009/022013, Example 45), formulated with 0 zinc per 6 insulin molecules (1 nmol/kg), and the resulting changes in plasma glucose, respectively (1 nmol/kg).

TABLE 15

Pharmacokinetic parameters after sc. dosing of 1 nmol/kg of the compound of WO 2009/0022013, Example 45

| Compound | | AUC/D pM * min/ (pmol/kg) | $T_{max}{}^a$ (min) | $C_{max}$/D pM/ (nmol/kg) | MRT (min) | $T_{1/2}{}^b$ (min) |
|---|---|---|---|---|---|---|
| WO 2009/022013 Ex. 45 0 Zn/hexamer (n = 4) 1 nmol/kg | Mean SD | 422 51 | 45 17 | 736 344 | 1287 86 | 987 36 |

$^a T_{max}$ given as median ± SD
$^b T_{1/2}$ given as harmonic mean ± pseudo SD It is concluded that the insulin derivative of the prior art, WO 2009/022013, Example 45, in a formulation without zinc is associated with a protracted tailing, possibly originating from a delayed absorption of a part of the subcutaneous depot. The plasma concentration of this insulin at the 24 hour (1440 minutes) time point is 98 pM. Further, the blood glucose lowering effect is extended to last for at least 8 hours (480 minutes). Mean residence time was 1287 minutes, almost 1 day. This makes this insulin of the prior art inappropriate for prandial use.

Example 40; Subcutaneous PK/PD Profile of a Close Analogue of an Insulin Derivative of the Prior Art in LYD Pigs Following the general procedure above, the following PK and PD profiles were obtained for the C14 diacid analogue A22K(N(eps)-tetradecanedioyl-gGlu-2×OEG), B29R, desB30 human insulin representative of the prior art as described in WO 2009/022013 (see in particular Example 45 (A22K(N(eps)-hexadecanedioyl-gGlu-2×OEG), B29R, desB30 human insulin).

Formulations Used

A22K(N(eps)-tetradecanedioyl-gGlu-2×OEG), B29R, desB30 human insulin (the 1,14-tetradecanedioyl (C14 diacid) analogue of the 1,16-hexadecanedioyl (C16 diacid) analogue of WO 2009/022013, Example 45), 588 µM; 1.6% (w/vol) glycerol; 30 mM phenol; 7 mM tris, pH=7.4 (0 Zn/hexamer)

The results of these determinations are presented in the appended FIG. 9 and in Table 16, below.

Figure 12:
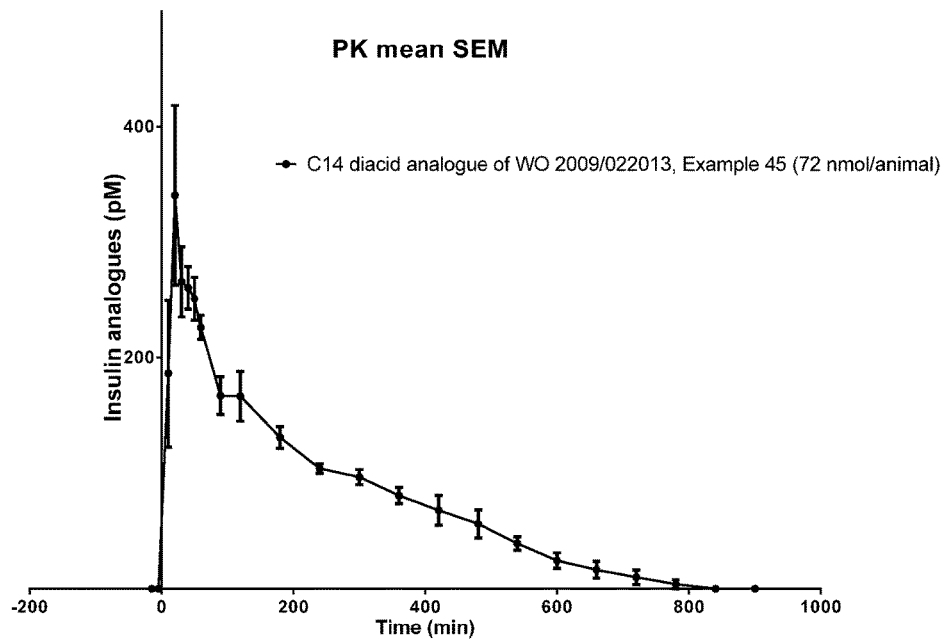
FIGS. 12 and 13 shows the PK (pharmacokinetic) profile (insulin concentrations vs. time) of a tetradecanedioic acid analogue representative of the prior art (WO 2009/022013, Example 45, shown in FIGS. 10 and 11, formulated with 0 zinc per 6 insulin molecules (72 nmol/animal), and the resulting changes in plasma glucose, respectively.
Figure 13:
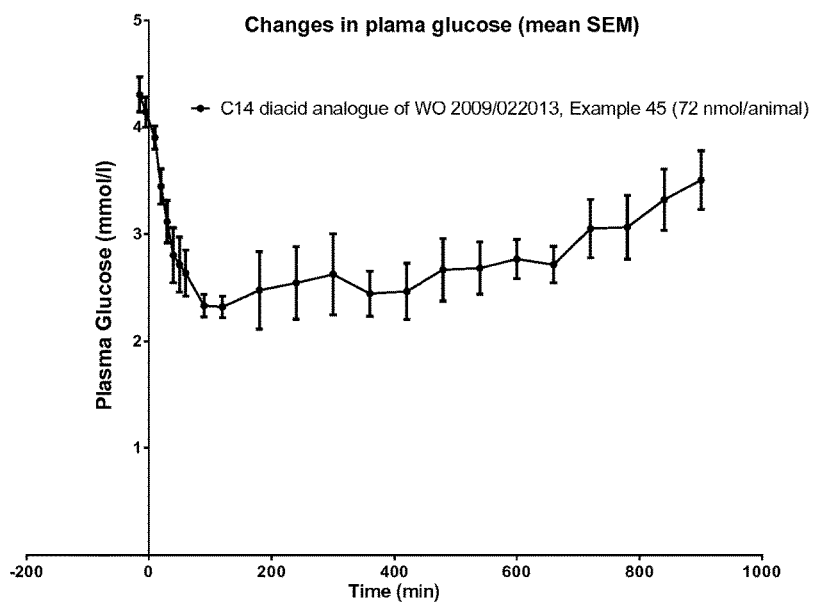

FIGS. 12 and 13 shows the PK (pharmacokinetic) profile (insulin concentrations vs. time) of C14 diacid analogue of an insulin derivative representative of the prior art, i.e. A22K(N(eps)-hexadecanedioyl-gGlu-2×OEG), B29R, desB30 human insulin (WO 2009/022013, Example 45), formulated with 0 zinc per 6 insulin molecules (1 nmol/kg), and the resulting changes in plasma glucose, respectively (72 nmol/animal).

TABLE 16

Pharmacokinetic parameters after sc. dosing of 1 nmol/kg of the C14 diacid analogue of the C16 diacid analogue of the prior art compound of WO 2009/0022013, Example 45 (72 nmol/animal)

| Animal no | Dose pmol/kg | $T_{max}$ min | $C_{max}$/D pM/(nmol/kg) | AUC/D pM * min/(pmol/kg) | %$_{extrap}$ % | $T_{1/2}$ Min | MRT min |
|---|---|---|---|---|---|---|---|
| 10107 | 713 | 50 | 450 | 128 | 6 | 182 | 310 |
| 10109 | 1714 | 20 | 241 | 40 | 9 | 148 | 226 |
| 10110 | 720 | 10 | 513 | 104 | 7 | 153 | 261 |
| 10111 | 706 | 50 | 363 | 81 | 8 | 158 | 255 |
| 10112 | 1735 | 20 | 344 | 41 | 10 | 219 | 305 |
| N | | 5 | 5 | 5 | 5 | 5 | 5 |
| Mean | | | 382 | 79 | 8 | | 271 |
| SD | | 19 | 104 | 39 | 1 | | 35 |
| Median | | 20 | | | | | |
| Harmonic Mean | | | | | | 168 | |
| Pseudo SD | | | | | | 25 | |

Conclusion

It is concluded that the C14 diacid version of the insulin derivative of the prior art, WO 2009/022013, Example 45, in a formulation without zinc is associated with a protracted tailing, possibly originating from a delayed absorption of a part of the subcutaneous depot. The plasma concentration of this insulin at the 10 hour (600 minutes) time point is 24 pM. The mean retention time (MRT) of this C14 diacid analogue of the prior art was found to be 271 minutes. The corresponding results obtained with the C14 diacid analogues of Examples 1 and 2 of the present invention were 165 and 111 minutes, respectively. Further, the blood glucose lowering effect is extended to last for at least 11 hours (660 minutes).

This makes this insulin of the prior art inappropriate for prandial use.

Example 41; Subcutaneous PK/PD Profile of the Insulin Derivative of Example 2 in Obese Zucker Rats, Comparison of Profiles with and without 170 mM Nicotinamide in the Formulation Following the general procedure above, the following PK and PD profiles were obtained for the insulin derivative of Example 2.

Formulation Used

Insulin derivative of Example 2, pH=7.43; 621 µM; 1.8% (w/vol) glycerol; 16 mM phenol; 16 mM m-cresol, 10 mM sodium chloride (0 Zn/hexamer), with and without 170 mM nicotinamide.

The rats were dosed 40 nmol/kg

Figure 15:
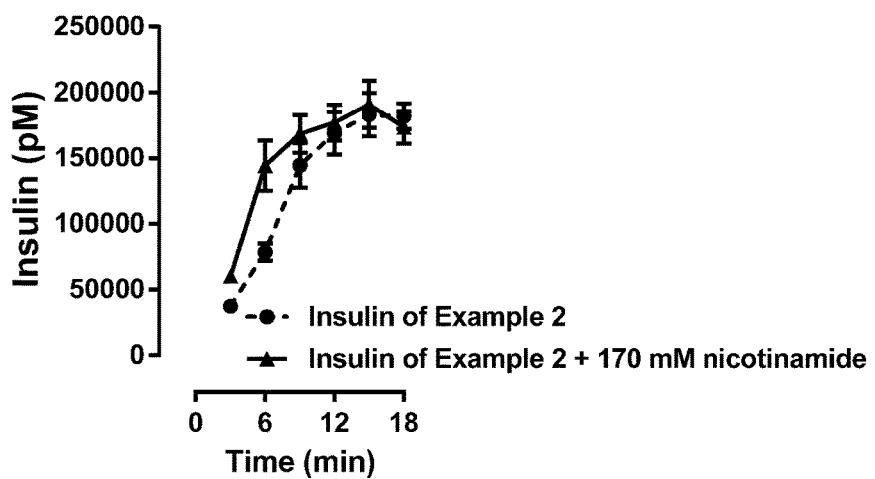
FIG. 15 shows the PK/PD profile of the insulin derivative of Example 2 following subcutaneous injection in obese Zucker rats in absence/presence of 170 mM nicotinamide.

The results of these determinations are presented in the appended FIG. 15.

It is concluded that inclusion of 170 mM nicotinamide in the zinc-free formulation of the insulin of Example 2, dosed subcutaneously to Zucker rats, results in a PK profile that is even more rapid-acting, with an earlier $T_{max}$. It is thus shown that inclusion of nicotinamide to the insulin formulation of Example 2 of the invention results in an insulin formulation that is even more suited for prandial use.

Example 42; Subcutaneous PK/PD Profile of the Insulin Derivative of Example 7 in Obese Zucker Rats, Comparison of Profiles with and without 170 mM Nicotinamide in the Formulation Following the general procedure above, the following PK and PD profiles were obtained for the insulin derivative of Example 7.

Formulations Used:

Insulin derivative of Example 7, pH=7.39; 604 µM; 1.6% (w/vol) glycerol; 16 mM phenol; 16 mM m-cresol, 7 mM sodium phosphate, 10 mM sodium chloride (0 Zn/hexamer), 170 mM nicotinamide.

Insulin derivative of Example 7, pH=7.39; 599 µM; 1.6% (w/vol) glycerol; 16 mM phenol; 16 mM m-cresol; 7 mM sodium phosphate; 10 mM sodium chloride (0 Zn/hexamer).

The rats were dosed 40 nmol/kg

Figure 16:
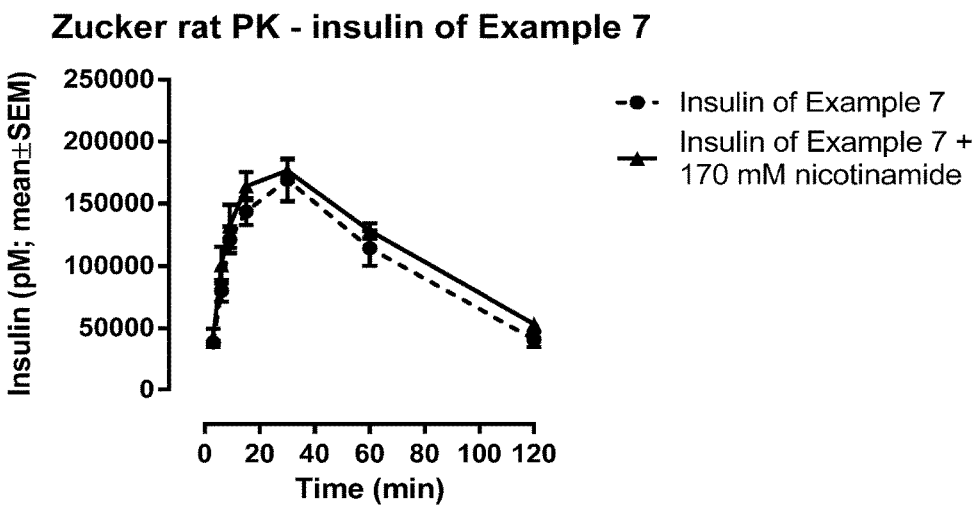
FIGS. 16-17 show the PK/PD profile of the insulin derivative of Example 7 following subcutaneous injection in obese Zucker rats in absence/presence of 170 mM nicotinamide.
Figure 17:
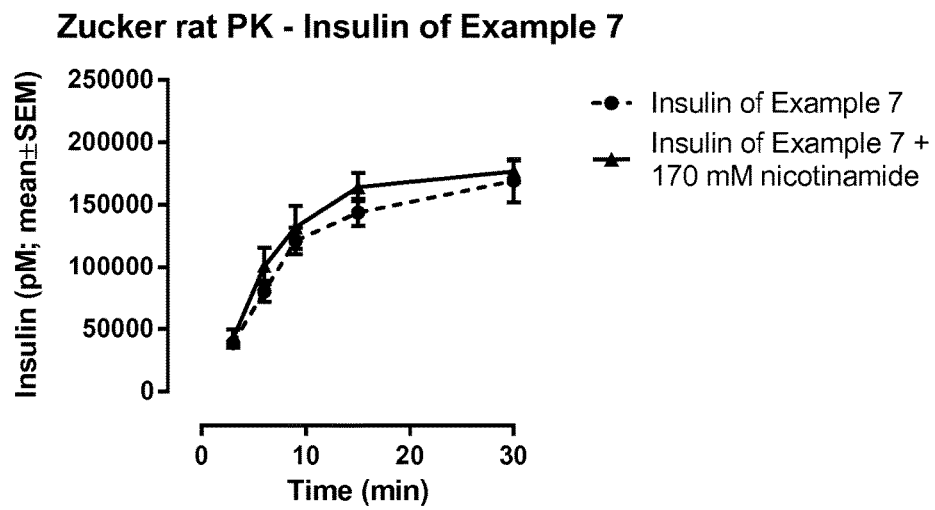

The results of these determinations are presented in the appended FIGS. 16-17.

It is concluded that inclusion of 170 mM nicotinamide in the zinc-free formulation of the insulin of Example 7, dosed subcutaneously to Zucker rats, results in a PK profile that is even more rapid-acting, with an earlier $T_{max}$. It is thus shown that inclusion of nicotinamide to the insulin formulation of Example 7 of the invention results in an insulin formulation that is even more suited for prandial use.

Example 43; Subcutaneous PK/PD Profile of the Insulin Derivative of Example 16 in Obese Zucker Rats, Comparison of Profiles with and without 170 mM Nicotinamide in the Formulation Following the general procedure above, the following PK and PD profiles were obtained for the insulin derivative of Example 16.

Formulations Used

Insulin derivative of Example 16, pH=7.44; 599 µM; 1.6% (w/vol) glycerol; 16 mM phenol; 16 mM m-cresol; 7 mM sodium phosphate; 10 mM sodium chloride (0 Zn/hexamer); 170 mM nicotinamide.

Insulin derivative of Example 16, pH=7.40; 581 µM; 1.6% (w/vol) glycerol; 16 mM phenol; 16 mM m-cresol; 7 mM sodium phosphate; 10 mM sodium chloride (0 Zn/hexamer).

The rats were dosed 40 nmol/kg

Figure 18:
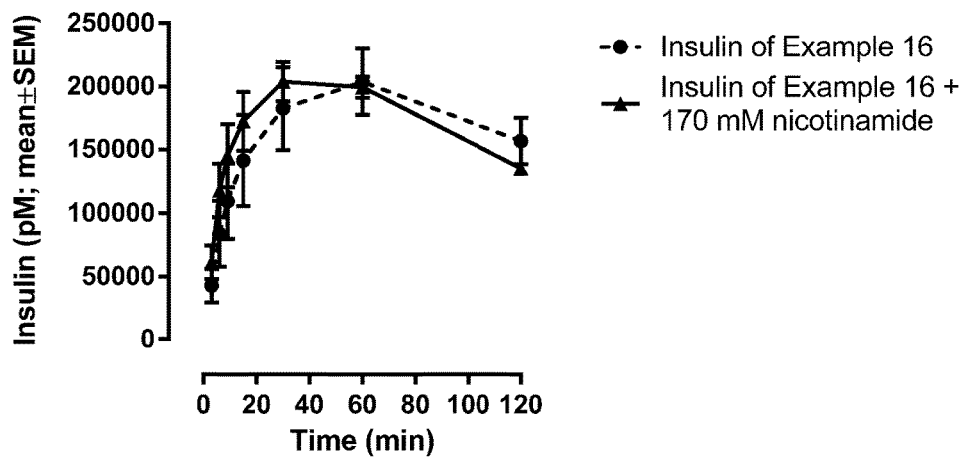
FIGS. 18-19 show the PK/PD profile of the insulin derivative of Example 7 following subcutaneous injection in obese Zucker rats in absence/presence of 170 mM nicotinamide.
Figure 19:
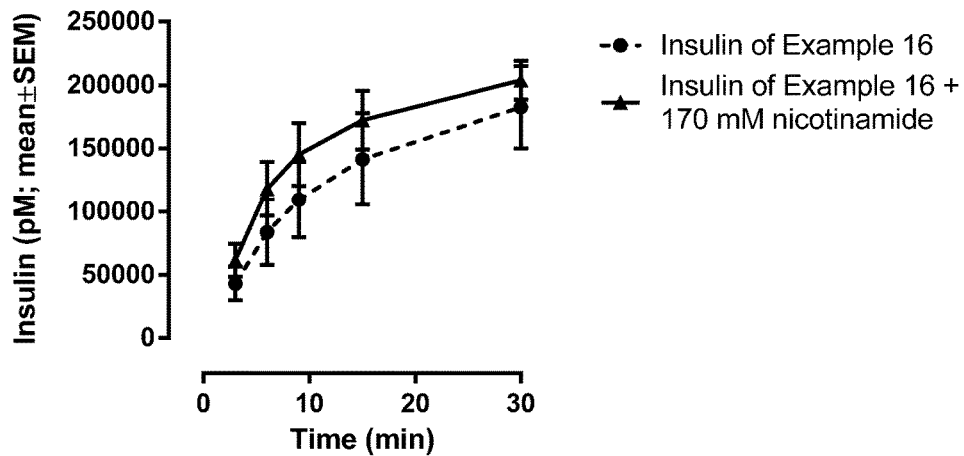

The results of these determinations are presented in the appended FIGS. 18-19.

It is concluded that inclusion of 170 mM nicotinamide in the zinc-free formulation of the insulin of Example 16, dosed subcutaneously to Zucker rats, results in a PK profile that is even more rapid-acting, with an earlier $T_{max}$. It is thus shown that inclusion of nicotinamide to the insulin formulation of Example 16 of the invention results in an insulin formulation that is even more suited for prandial use.

Example 44; Subcutaneous PK/PD Profile of the Insulin Derivative of Example 4 in LYD Pigs, Comparison of Profiles with and without 170 μM Nicotinamide in the Formulation Following the general procedure above, the following PK and PD profiles were obtained for the insulin derivative of Example 4.

Formulation Used

Insulin derivative of Example 4, pH=7.42; 0.604 mM insulin derivative; 16 mM phenol; 16 mM m-cresol; 2% (w/vol) glycerol; 7 mM phosphate (0 Zn/hexamer).

Insulin derivative of Example 4, pH=7.43; 0.605 mM insulin derivative; 170 mM nicotinamide; 16 mM phenol; 16 mM m-cresol; 0.6% (w/vol) glycerol; 7 mM phosphate The pigs were dosed 1 nmol/kg.

Figure 20:
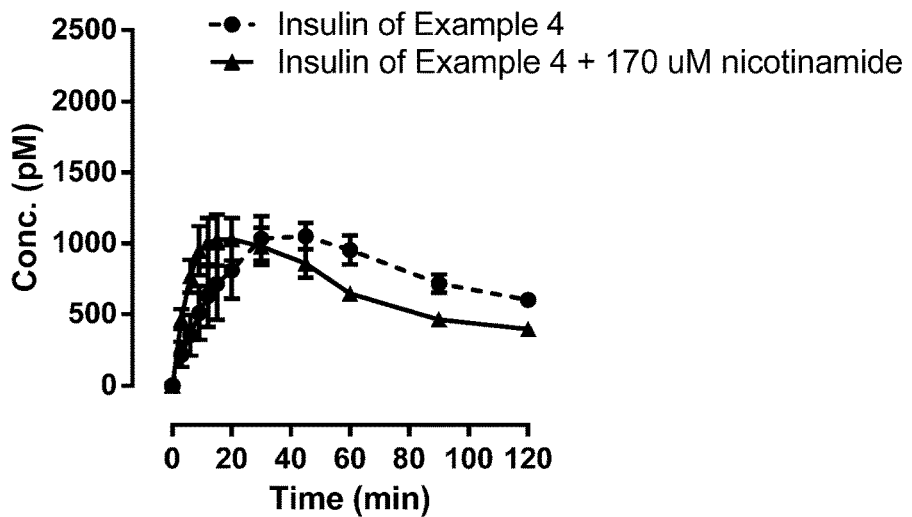
FIGS. 20-21 show the PK/PD profile of the insulin derivative of Example 4 following subcutaneous injection in obese Zucker rats in absence/presence of 170 mM nicotinamide.

The results of these determinations are presented in the appended FIG. 20.

It is concluded that inclusion of 170 μM nicotinamide in the zinc-free formulation of the insulin of Example 4, dosed subcutaneously to pigs, results in a PK profile that is even more rapid-acting, with an earlier $T_{max}$. It is thus shown that inclusion of nicotinamide to the insulin formulation of Example 4 of the invention results in an insulin formulation that is even more suited for prandial use.

Example 45; Subcutaneous PK/PD Profile of the Insulin Derivative of Example 2 in LYD Pigs, Comparison of Profiles with and without 170 μM Nicotinamide in the Formulation Following the general procedure above, the following PK and PD profiles were obtained for the insulin derivative of Example 2.

Formulation Used

Insulin derivative of Example 2, pH=7.4; 608 μM; 2% (w/vol) glycerol; 16 mM phenol; 16 mM m-cresol, 7 mM sodium phosphate (0 Zn/hexamer).

Insulin derivative of Example 2, pH=7.4; 614 μM; 170 μM nicotinamide, 0.6% (w/vol) glycerol; 16 mM phenol; 16 mM m-cresol, 7 mM sodium phosphate (0 Zn/hexamer).

The pigs were dosed 1 nmol/kg.

Figure 21:
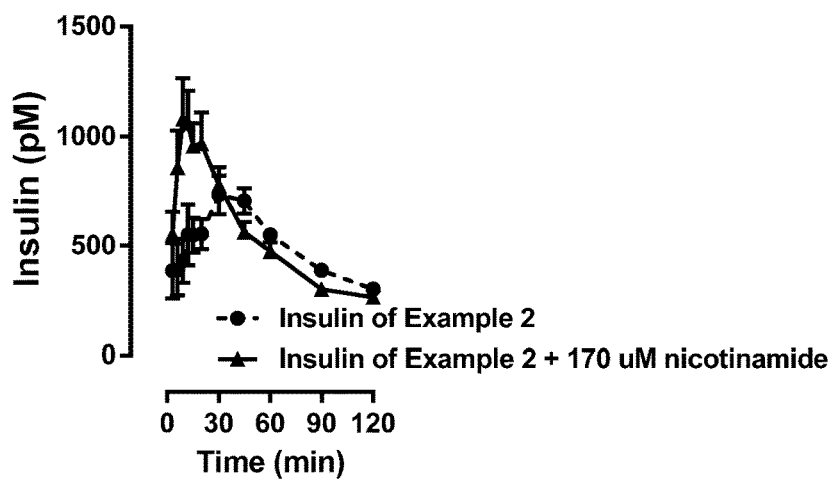

The results of these determinations are presented in the appended FIG. 21.

It is concluded that inclusion of 170 μM nicotinamide in the zinc-free formulation of the insulin of Example 2, dosed subcutaneously to pigs, results in a PK profile that is even more rapid-acting, with an earlier $T_{max}$. It is thus shown that inclusion of nicotinamide to the insulin formulation of Example 2 of the invention results in an insulin formulation that is even more suited for prandial use.

The invention claimed is:

1. An insulin derivative, which insulin derivative is an acylated analogue of human insulin, which analogue is [A22K, desB27, B29R, desB30] relative to human insulin;
and which insulin analogue is derivatized by acylation of the epsilon amino group of the lysine residue at the A22 position with a group of Formula II:

[Acyl]-[Linker]- wherein the Linker group is an amino acid chain composed of from 1 to 10 amino acid residues selected from -gGlu- and -OEG-; wherein
gGlu represents a gamma glutamic acid residue;
OEG represents the residue of 8-amino-3,6-dioxaoctanoic acid (i.e. a group of the formula —NH—(CH$_2$)$_2$—O—(CH$_2$)$_2$—O—CH$_2$—CO—);
which amino acid residues may be present in any order; and which amino acid chain comprises at least one gGlu residue; and wherein the Acyl group is a residue of an α,ω-di-carboxylic acid selected from
1,14-tetradecanedioic acid;
1,15-pentadecanedioic acid; and
1,16-hexadecanedioic acid;
which acylated analogue, may only comprise additional substitution of A14E, and/or B3E or B3Q.

2. The insulin derivative according to claim 1, which analogue is [A14E, A22K, B3E, desB27, B29R, desB30], [A14E, A22K, desB27, B29R, desB30], [A22K, B3E, desB27, B29R, desB30], [A22K, B3Q, desB27, B29R, desB30], or [A22K, desB27, B29R, desB30] relative to human insulin, and which insulin analogue is acylated at the epsilon amino group of the lysine residue at the A22 position.

3. The insulin derivative according to claim 1, wherein the Linker group is selected from -gGlu-; -2×gGlu-; -3×gGlu-; -4×gGlu-; -gGlu-2×OEG-; -gGlu-3×(OEG-gGlu)-; -4×gGlu-2×OEG-; -2×OEG-; and -2×OEG-gGlu-.

4. The insulin derivative according to claim 3, wherein the Linker group is selected from -gGlu-; -2×gGlu-; -4×gGlu-; -gGlu-2×OEG-; -gGlu-3×(OEG-gGlu)-; -2×OEG-; and -2×OEG-gGlu-.

5. The insulin derivative according to claim 4, wherein the Linker group is -4×gGlu-.

6. The insulin derivative according to claim 1, wherein the Acyl group is a di-acid group derived from 1,14-tetradecanedioic acid; 1,15-pentadecanedioic acid; or 1,16-hexadecanedioic acid.

7. The insulin derivative according to claim 6, wherein the Acyl group is a 1,14-tetradecanedioic acid.

8. The insulin derivative according to claim 1, wherein the group of Formula II (i.e. [Acyl]-[Linker]-) is tetradecanedioyl-gGlu-; tetradecanedioyl-2×gGlu-; tetradecanedioyl-3×gGlu-; tetradecanedioyl-4×gGlu-; tetradecanedioyl-gGlu-2×OEG-; tetradecanedioyl-4×gGlu-2×OEG-; tetradecanedioyl-2×OEG-; pentadecanedioyl-4×gGlu; hexadecanedioyl-4×gGlu-; hexadecanedioyl-gGlu-2×OEG-; or hexadecanedioyl-3×(gGlu-OEG)-gGlu-.

9. The insulin derivative according to claim 8, wherein the group of Formula II (i.e. [Acyl]-[Linker]-) is tetradecanedioyl-4×gGlu-.

10. A pharmaceutical composition comprising an insulin derivative according to claim 1, and one or more pharmaceutically acceptable carriers or diluents.

11. The pharmaceutical composition according to claim 10, formulated as a low-zinc composition, with no added zinc ions.

12. The pharmaceutical composition according to claim 11, formulated as a low-zinc composition, comprising less than 0.2 $Zn^{2+}$ ions per 6 insulin molecules.

13. The low-zinc pharmaceutical composition according to claim 11, wherein no surfactant has been added.

14. The low-zinc pharmaceutical composition according to claim 11, comprising a nicotinic compound, and in particular nicotinamide.

15. The pharmaceutical composition according to claim 10, formulated as a low-zinc composition, with no added zinc ions, and comprising an acylated analogue of human insulin selected from:
   A22K(N(eps)-tetradecanedioyl-4×gGlu), B3E, desB27, B29R, desB30 human insulin;
   A22K(N(eps)-hexadecanedioyl-4×gGlu), B3E, desB27, B29R, desB30 human insulin;
   A22K(N(eps)-hexadecanedioyl-gGlu-2×OEG), B3E, desB27, B29R, desB30 human insulin;
   A22K(N(eps)-hexadecanedioyl-3×(gGlu-OEG)-gGlu), B3E, desB27, B29R, desB30 human insulin;
   A22K(N(eps)-tetradecanedioyl-gGlu-2×OEG), B3E, desB27, B29R, desB30 human insulin;
   A22K(N(eps)-pentadecanedioyl-4×gGlu), B3E, desB27, B29R, desB30 human insulin;
   A22K(N(eps)-tetradecanedioyl-4×gGlu), B3Q, desB27, B29R, desB30 human insulin;
   A22K(N(eps)-hexadecanedioyl-gGlu-2×OEG), B3Q, desB27, B29R, desB30 human insulin;
   A22K(N(eps)-hexadecanedioyl-3×(gGlu-OEG)-gGlu), B3Q, desB27, B29R, desB30 human insulin;
   A22K(N(eps)-tetradecanedioyl-gGlu-2×OEG), B3Q, desB27, B29R, desB30 human insulin;
   A22K(N(eps)-hexadecanedioyl-4×gGlu), B3Q, desB27, B29R, desB30 human insulin;
   A22K(N(eps)-tetradecanedioyl-4×gGlu-2×OEG), desB27, B29R, desB30 human insulin;
   A22K(N(eps)-tetradecanedioyl-4×gGlu-2×OEG), B3E, desB27, B29R, desB30 human insulin;
   A14E, A22K(N(eps)-tetradecanedioyl-gGlu-2×OEG), B3E, desB27, B29R, desB30 human insulin;
   A14E, A22K(N(eps)-tetradecanedioyl-4×gGlu), B3E, desB27, B29R, desB30 human insulin;
   A22K(N(eps)-tetradecanedioyl-2×gGlu), B3E, desB27, B29R, desB30 human insulin;
   A22K(N(eps)-tetradecanedioyl-gGlu), B3E, desB27, B29R, desB30 human insulin; and
   A22K(N(eps)-tetradecanedioyl-3×gGlu), B3E, desB27, B29R, desB30 human insulin.

16. A method for the treatment or alleviation of a disease, disorder or condition relating to diabetes, Type 1 diabetes, Type 2 diabetes, impaired glucose tolerance, hyperglycemia, dyslipidemia, obesity, metabolic syndrome (metabolic syndrome X, insulin resistance syndrome), hypertension, cognitive disorders, atherosclerosis, myocardial infarction, stroke, cardiovascular disorders, coronary heart disease, inflammatory bowel syndrome, dyspepsia, or gastric ulcers, which method comprises administration to a subject in need thereof a therapeutically effective amount of the insulin derivative according to claim 1.

17. The insulin derivative according to claim 1, which acylated analogue additionally comprises the A14E substitution.

18. The insulin derivative according to claim 1, which acylated analogue additionally comprises the A14E and B3E substitutions.

19. The insulin derivative according to claim 1, which acylated analogue additionally comprises the B3E substitution.

20. The insulin derivative according to claim 1, which acylated analogue additionally comprises the B3Q substitution.

21. The insulin derivative according to claim 1, which analogue is [A14E, A22K, desB27, B29R, desB30], [A22K, B3E, desB27, B29R, desB30], [A22K, B3Q, desB27, B29R, desB30], or [A22K, desB27, B29R, desB30] relative to human insulin, and which insulin analogue is acylated at the epsilon amino group of the lysine residue at the A22 position.

22. The insulin derivative according to claim 21, which analogue is [A22K, B3E, desB27, B29R, desB30] relative to human insulin, and which insulin analogue is acylated at the epsilon amino group of the lysine residue at the A22 position.

23. The insulin derivative according to claim 1, which is A22K(N(eps)-tetradecanedioyl-4×gGlu), desB27, B29R, desB30 human insulin.

24. The insulin derivative according to claim 1, which is A22K(N(eps)-tetradecanedioyl-4×gGlu), B3E, desB27, B29R, desB30 human insulin.

25. The insulin derivative according to claim 1, which is A14E, A22K(N(eps)-tetradecanedioyl-4×gGlu), desB27, B29R, desB30 human insulin.

26. The insulin derivative according to claim 1, which is A22K(N(eps)-hexadecanedioyl-4×gGlu), B3E, desB27, B29R, desB30 human insulin.

27. The insulin derivative according to claim 1, which is A22K(N(eps)-hexadecanedioyl-gGlu-2×OEG), B3E, desB27, B29R, desB30 human insulin.

28. The insulin derivative according to claim 1, which is A22K(N(eps)-hexadecanedioyl-3×(gGlu-OEG)-gGlu), B3E, desB27, B29R, desB30 human insulin.

29. The insulin derivative according to claim 1, which is A22K(N(eps)-tetradecanedioyl-4×gGlu), B3Q, desB27, B29R, desB30 human insulin.

30. The insulin derivative according to claim 1, which is A22K(N(eps)-hexadecanedioyl-gGlu-2×OEG), B3Q, desB27, B29R, desB30 human insulin.

31. The insulin derivative according to claim 1, which is A22K(N(eps)-hexadecanedioyl-3×(gGlu-OEG)-gGlu), B3Q, desB27, B29R, desB30 human insulin.

32. The insulin derivative according to claim 1, which is A22K(N(eps)-tetradecanedioyl-2×gGlu), desB27, B29R, desB30 human insulin.

33. The insulin derivative according to claim 1, which is A22K(N(eps)-hexadecanedioyl-4×gGlu), desB27, B29R, desB30 human insulin.

34. The insulin derivative according to claim 1, which is A22K(N(eps)-hexadecanedioyl-gGlu-2×OEG), desB27, B29R, desB30 human insulin.

35. The insulin derivative according to claim 1, which is A22K(N(eps)-hexadecanedioyl-3×(gGlu-OEG)-gGlu), desB27, B29R, desB30 human insulin.

36. The insulin derivative according to claim 1, which is A22K(N(eps)-tetradecanedioyl-gGlu), desB27, B29R, desB30 human insulin.

37. The insulin derivative according to claim 1, which is A22K(N(eps)-tetradecanedioyl-gGlu-2×OEG), B3E, desB27, B29R, desB30 human insulin.

38. The insulin derivative according to claim 1, which is A22K(N(eps)-tetradecanedioyl-gGlu-2×OEG), B3Q, desB27, B29R, desB30 human insulin.

39. The insulin derivative according to claim 1, which is A22K(N(eps)-tetradecanedioyl-2×OEG), desB27, B29R, desB30 human insulin.

40. The insulin derivative according to claim 1, which is A22K(N(eps)-hexadecanedioyl-4×gGlu), B3Q, desB27, B29R, desB30 human insulin.

41. The insulin derivative according to claim 1, which is A22K(N(eps)-pentadecanedioyl-4×gGlu), B3E, desB27, B29R, desB30 human insulin.

42. The insulin derivative according to claim 1, which is A22K(N(eps)-tetradecanedioyl-4×gGlu-2×OEG), desB27, B29R, desB30 human insulin.

43. The insulin derivative according to claim 1, which is A22K(N(eps)-tetradecanedioyl-4×gGlu-2×OEG), B3E, desB27, B29R, desB30 human insulin.

44. The insulin derivative according to claim 1, which is A14E, A22K(N(eps)-tetradecanedioyl-gGlu-2×OEG), B3E, desB27, B29R, desB30 human insulin.

45. The insulin derivative according to claim 1, which is A14E, A22K(N(eps)-tetradecanedioyl-4×gGlu), B3E, desB27, B29R, desB30 human insulin.

46. The insulin derivative according to claim 1, which is A22K(N(eps)-tetradecanedioyl-2×gGlu), B3E, desB27, B29R, desB30 human insulin.

47. The insulin derivative according to claim 1, which is A22K(N(eps)-tetradecanedioyl-gGlu), B3E, desB27, B29R, desB30 human insulin.

48. The insulin derivative according to claim 1, which is A22K(N(eps)-tetradecanedioyl-3×gGlu), B3E, desB27, B29R, desB30 human insulin.

\* \* \* \* \*

SEQUENCE LISTING

```
<160> NUMBER OF SEQ ID NOS: 5

<210> SEQ ID NO 1
<211> LENGTH: 22
<212> TYPE: PRT
<213> ORGANISM: Artificial Sequence
<220> FEATURE:
<223> OTHER INFORMATION: A chain of analogue of Human insulin
<220> FEATURE:
<221> NAME/KEY: CHAIN
<222> LOCATION: (1)..(22)
<220> FEATURE:
<221> NAME/KEY: MOD_RES
<222> LOCATION: (22)..(22)
<223> OTHER INFORMATION: ACETYLATION; (N(eps)-tetradecanedioyl-4xgGlu);
      (N(eps)-hexadecanedioyl-4xgGlu);
      (N(eps)-hexadecanedioyl-gGlu-2xOEG);
      (N(eps)-hexadecanedioyl-3x(gGlu-OEG)-gGlu);

<400> SEQUENCE: 1

Gly Ile Val Glu Gln Cys Cys Thr Ser Ile Cys Ser Leu Tyr Gln Leu
1               5                   10                  15

Glu Asn Tyr Cys Asn Lys
            20

<210> SEQ ID NO 2
<211> LENGTH: 22
<212> TYPE: PRT
<213> ORGANISM: Artificial Sequence
<220> FEATURE:
<223> OTHER INFORMATION: A chain of analogue of Human insulin
<220> FEATURE:
<221> NAME/KEY: CHAIN
<222> LOCATION: (1)..(22)
<220> FEATURE:
<221> NAME/KEY: MOD_RES
<222> LOCATION: (22)..(22)
<223> OTHER INFORMATION: ACETYLATION; (N(eps)tetradecanedioyl-4xgGlu);
      (N(eps)-tetradecanedioyl-4xgGlu);
      (N(eps)-tetradecanedioyl-gGlu-2xOEG).

<400> SEQUENCE: 2
```

```
Gly Ile Val Glu Gln Cys Cys Thr Ser Ile Cys Ser Leu Glu Gln Leu
1               5                   10                  15

Glu Asn Tyr Cys Asn Lys
                20

<210> SEQ ID NO 3
<211> LENGTH: 28
<212> TYPE: PRT
<213> ORGANISM: Artificial Sequence
<220> FEATURE:
<223> OTHER INFORMATION: B chain of analogue of Human insulin

<400> SEQUENCE: 3

Phe Val Asn Gln His Leu Cys Gly Ser His Leu Val Glu Ala Leu Tyr
1               5                   10                  15

Leu Val Cys Gly Glu Arg Gly Phe Phe Tyr Pro Arg
                20                  25

<210> SEQ ID NO 4
<211> LENGTH: 28
<212> TYPE: PRT
<213> ORGANISM: Artificial Sequence
<220> FEATURE:
<223> OTHER INFORMATION: B chain of analogue of Human insulin

<400> SEQUENCE: 4

Phe Val Glu Gln His Leu Cys Gly Ser His Leu Val Glu Ala Leu Tyr
1               5                   10                  15

Leu Val Cys Gly Glu Arg Gly Phe Phe Tyr Pro Arg
                20                  25

<210> SEQ ID NO 5
<211> LENGTH: 28
<212> TYPE: PRT
<213> ORGANISM: Artificial Sequence
<220> FEATURE:
<223> OTHER INFORMATION: B chain of analogue of Human insulin

<400> SEQUENCE: 5

Phe Val Gln Gln His Leu Cys Gly Ser His Leu Val Glu Ala Leu Tyr
1               5                   10                  15

Leu Val Cys Gly Glu Arg Gly Phe Phe Tyr Pro Arg
                20                  25
```